US010648036B2

(12) United States Patent
Sugiyama

(10) Patent No.: US 10,648,036 B2
(45) Date of Patent: **\*May 12, 2020**

(54) RECEPTOR GENE FOR PEPTIDE CANCER ANTIGEN-SPECIFIC T CELL

(71) Applicant: International Institute of Cancer Immunology, Inc., Osaka (JP)

(72) Inventor: Haruo Sugiyama, Osaka (JP)

(73) Assignee: International Institute of Cancer Immunology, Inc., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/687,569

(22) Filed: Apr. 15, 2015

(65) Prior Publication Data

US 2015/0292034 A1    Oct. 15, 2015

Related U.S. Application Data

(62) Division of application No. 14/129,695, filed as application No. PCT/JP2012/065707 on Jun. 20, 2012, now Pat. No. 9,803,246.

(30) Foreign Application Priority Data

Jun. 28, 2011 (JP) ................................ 2011-143273

(51) Int. Cl.

| C12Q 1/6886 | (2018.01) |
|---|---|
| C07K 14/725 | (2006.01) |
| G01N 33/574 | (2006.01) |
| C07K 16/28 | (2006.01) |
| C07K 16/30 | (2006.01) |
| C12Q 1/686 | (2018.01) |
| C12Q 1/6881 | (2018.01) |
| G01N 33/569 | (2006.01) |

(52) U.S. Cl.
CPC ........ *C12Q 1/6886* (2013.01); *C07K 14/7051* (2013.01); *C07K 16/2809* (2013.01); *C07K 16/30* (2013.01); *C12Q 1/686* (2013.01); *C12Q 1/6881* (2013.01); *G01N 33/56977* (2013.01); *G01N 33/574* (2013.01); *C07K 2317/34* (2013.01); *C07K 2317/565* (2013.01); *C12Q 2600/106* (2013.01); *C12Q 2600/158* (2013.01); *G01N 2333/7051* (2013.01)

(58) Field of Classification Search
None
See application file for complete search history.

(56) References Cited

U.S. PATENT DOCUMENTS

| 4,923,799 | A | 5/1990 | Mak |
| 5,512,478 | A | 4/1996 | Orser et al. |
| 6,013,444 | A | 1/2000 | Dau et al. |
| 6,225,051 | B1 | 5/2001 | Sugiyama et al. |
| 6,582,908 | B2 | 6/2003 | Fodor et al. |
| 9,803,246 | B2 * | 10/2017 | Sugiyama .......... C07K 14/7051 |
| 2002/0131960 | A1 | 9/2002 | Sadelain et al. |
| 2003/0072767 | A1 | 4/2003 | Gaiger et al. |
| 2003/0082196 | A1 | 5/2003 | Gaiger et al. |
| 2004/0097703 | A1 | 5/2004 | Sugiyama |
| 2004/0247609 | A1 | 12/2004 | Sugiyama |
| 2005/0002951 | A1 | 1/2005 | Sugiyama et al. |
| 2005/0260222 | A1 | 11/2005 | Gupta et al. |
| 2005/0266014 | A1 | 12/2005 | Sugiyama et al. |
| 2006/0035291 | A1 | 2/2006 | Itoh et al. |
| 2007/0036808 | A1 | 2/2007 | Sugiyama |
| 2007/0082860 | A1 | 4/2007 | Sugiyama et al. |
| 2007/0128207 | A1 | 6/2007 | Sugiyama |
| 2007/0238099 | A1 | 10/2007 | Cohen et al. |
| 2008/0070835 | A1 | 3/2008 | Sugiyama |
| 2008/0152631 | A1 | 6/2008 | Sugiyama |
| 2009/0099090 | A1 | 4/2009 | Sugiyama et al. |
| 2009/0263409 | A1 | 10/2009 | Sugiyama |
| 2010/0190163 | A1 | 7/2010 | Sugiyama |
| 2014/0315735 | A1 | 10/2014 | Sugiyama |
| 2014/0315758 | A1 | 10/2014 | Sugiyama |

FOREIGN PATENT DOCUMENTS

| CN | 101668853 A | 3/2010 |
| EP | 1 410 804 A1 | 4/2004 |
| EP | 1 447 091 A1 | 8/2004 |
| EP | 1 473 564 A1 | 11/2004 |
| EP | 1 536 009 A1 | 6/2005 |
| EP | 1 550 453 A1 | 7/2005 |
| EP | 1 640 458 A1 | 3/2006 |
| EP | 2 116 596 A1 | 11/2009 |
| JP | 2001-517958 A | 10/2001 |

(Continued)

OTHER PUBLICATIONS

Extended European Search Report dated Mar. 18, 2015 in Patent Application No. 14192034.8.
Extended European Search Report dated May 12, 2015 in Patent Application No. 12803980.7.
Office Action dated Jun. 4, 2015 in Australian Patent Application No. 2013270605.
Office Action with Search Statement dated Jun. 4, 2015 in Australian Patent Application No. 2013206501.
Office Action dated May 15, 2015 in co-pending U.S. Appl. No. 14/129,695.
Extended European Search Report dated Oct. 31, 2011 in Patent Application No. 11154327.8.
Extended European Search Report dated Jul. 1, 2011 in Patent Application No. 11154325.2.

(Continued)

*Primary Examiner* — Nancy J Leith
(74) *Attorney, Agent, or Firm* — Oblon, McClelland, Maier & Neustadt, L.L.P.

(57) ABSTRACT

The invention provides the nucleotide sequence and amino acid sequence of the CDR3 domain of the T cell receptor (TCR) gene of a WT1-specific cytotoxic T cell (CTL) against WT1 protein. Also provided are a method for testing for and treating cancer using the nucleotide sequence and amino acid sequence, and a chip, primer set, kit, and device for testing for cancer comprising the nucleotide sequence and amino acid sequence.

8 Claims, 22 Drawing Sheets

Specification includes a Sequence Listing.

(56) References Cited

FOREIGN PATENT DOCUMENTS

| | | |
|---|---|---|
| JP | 2002-515243 A | 5/2002 |
| JP | 2002-525099 A | 8/2002 |
| JP | 2003-500004 A | 1/2003 |
| JP | 2009-278927 A | 12/2009 |
| KR | 2002-0013503 A | 2/2002 |
| KR | 10-1292971 B1 | 8/2013 |
| WO | WO 93/04695 A1 | 3/1993 |
| WO | 98/54223 A2 | 12/1998 |
| WO | 99/14371 A1 | 3/1999 |
| WO | 99/27957 A1 | 6/1999 |
| WO | 99/60119 A2 | 11/1999 |
| WO | WO 99/60119 A2 | 11/1999 |
| WO | WO 00/18795 A2 | 4/2000 |
| WO | WO 00/26249 A1 | 5/2000 |
| WO | WO 02/28414 A1 | 4/2002 |
| WO | WO 02/079253 A1 | 10/2002 |
| WO | WO 03/002142 A1 | 1/2003 |
| WO | WO 03/025569 A1 | 3/2003 |
| WO | WO 03/028757 A1 | 4/2003 |
| WO | WO 03/037060 A2 | 5/2003 |
| WO | 03/059155 A2 | 7/2003 |
| WO | WO 03/106682 A1 | 12/2003 |
| WO | 20041063706 A2 | 7/2004 |
| WO | WO 2005/053603 A2 | 6/2005 |
| WO | 2005/116074 A2 | 12/2005 |
| WO | WO 2006/064176 A1 | 6/2006 |
| WO | WO 2008/026927 A2 | 3/2008 |
| WO | 2008 108257 | 9/2008 |

OTHER PUBLICATIONS

"T-cell receptor beta chain variable region, partial [*Homo sapiens*]" http://www.ncbi.nlm.nih.gov/protein/AAM92197, GenBank Accession No. AAM92197 Aug. 10, 2002, 1 page.

Ton N. M. Schumacher, "T-Cell-Receptor Gene Therapy" Nature Reviews, vol. 2, Jul. 2002, pp. 512-519.

Klaus Willenbrock, et al., "Analysis of T-Cell Subpopulations in T-Cell Non-Hodgkin's Lymphoma of Angioimmunoblastic Lymphadenopathy with Dysproteinemia Type by Single Target Gene Amplification of T Cell Receptor-β Gene Rearrangements" American Journal of Pathology, vol. 158, No. 5, 2001, pp. 1851-1857.

J. Pinilla-Ibarz, et al., "Improved human T-cell responses against synthetic HLA-0201 analog peptides derived from the WT1 oncoprotein" Leukemia, vol. 20, 2006, pp. 2025-2033.

Akihiro Tsuboi, et al., "Enhanced induction of human WT1-specific cytotoxic T lymphocytes with a 9-mer WT1 peptide modified at HLA-A*2402-binding residues" Cancer Immunology Immunotherapy, vol. 51, XP03016309, 2002, pp. 614-620 and CAPLUS-abstract.

Yoshihiro Oka, et al., "Cancer Immunotherapy Targeting Wilms' Tumor Gene WT1 Product" The Journal of Immunology, XP000890067, 2000, pp. 1873-1880.

Katayoun Rezvani, et al., "Functional leukemia-associated antigen-specific memory CD8+ T cells exist in healthy individuals and in patients with chronic myelogenous leukemia before and after stem cell transplantation" Blood, vol. 102. No. 8, XP002474847, 2003, 37 pages.

P. Möller, et al., "Vaccination with IL-7 gene-modified autologous melanoma cells can enhance the anti-melanoma lytic activity in peripheral blood of patients with a good clinical performances status: a clinical phase I study" British Journal of Cancer, vol. 77, No. 11, 1998, pp. 1907-1916.

A. L. Menke, et al., "The Wilms' Tumor 1 Gene: Oncogene or Tumor Suppressor Gene?" International Review of Cytology, vol. 181, 1998, pp. 151-212.

John D. Altman, et al., "Phenotypic Analysis of Antigen-Specific T Lymphocytes" Science, vol. 274, 1996, pp. 94-96.

Niels Kruse, et al., "Quantification of cytokine mRNA expression by RT PCR in samples of previously frozen blood" Journal of Immunological Methods, vol. 210, 1997, pp. 195-203.

Cecil Czerkinsky, et al., "Reverse ELISPOT assay for clonal analysis of cytokine production, I. Enumeration of gamma-interferon-secreting cells" Journal of Immunological Methods, vol. 110, 1988, pp. 29-36.

Haruo Sugiyama, "Cancer Immunotherapy Targeting WT1 Protein" International Journal of Hematology, vol. 76, 2002, pp. 127-132.

Manfred Gessler, et al., "Homozygous deletion in Wilms tumours of a zinc-finger gene identified by chromosome jumping" Nature, vol. 343, 1990, pp. 774-778.

Katherine M. Call, et al., "Isolation and Characterization of a Zinc Finger Polypeptide Gene at the Human Chromosome 11 Wilms' Tumor Locus" Cell, vol. 60, 1990, pp. 509-520.

Y. Maeda, et al., "Detection of peptide-specific CTL-precursors in peripheral blood lymphocytes of cancer patients" British Journal of Cancer, vol. 87, XP002475150, 2002, pp. 796-804.

Hideki Ohminami, et al., "HLA class I-restricted lysis of leukemia cells by a CD8+ cytotoxic T-lymphocyte clone specific for WT1 peptide" Blood, vol. 95, No. 1, 2000, pp. 286-293.

Masahiro Nagai, et al., "Increased Activated Human T cell Lymphotropic Virus Type I (HTLV-1) Tax11-19-Specific Memory and Effector CD8+ Cells in Patients with HTLV-I-Associated Myelopathy/Tropical Spastic Paraparesis: Correlation with HTLV-1 Provirus Load" The Journal of Infectious Disease, vol. 183, 2001, pp. 197-205.

Haruo Sugiyama, et al., "Wilms' Tumor Gene WT1: Its Oncogenic Function and Clinical Application" International Journal of Hematology, vol. 73, 2001, pp. 177-187.

Wolfgang Herr, et al., "Frequency analysis of tumor-reactive cytotoxic T lymphocytes in peripheral blood of a melanoma patient vaccinated with autologous tumor cells" Cancer Immunology Immunotherapy, vol. 39, 1994, pp. 93-99.

Theresa L. Whiteside, "Monitoring of Antigen-Specific Cytolytic T Lymphocytes in Cancer Patients Receiving Immunotherapy" Clinical and Vaccine Immunology, vol. 7, No. 3, 2000, 7 pages.

Y. Oka, et al., "WT1 as a Novel Target Antigen for Cancer Immunotherapy" Current Cancer Drug Targets, vol. 2, XP008089881, 2002, pp. 45-54.

Ivan M. Barrello, et al., "Cancer Vaccines for Hematologic Malignancies" Cancer Control, vol. 9, No. 2, XP002475149, Mar. 2002, pp. 138-151.

Akihiro Tsuboi, et al., "WT1 Peptide-Based Immunotherapy for Patients with Lung Cancer: Report of Two Cases" Microbiology and Immunology, vol. 48, No. 3, XP002391404, 2004, pp. 175-184.

Masaki Yasukawa, "Immunogenetherapy for Leukemia by T-cell receptor gene transfer" Hematology & Oncology, vol. 51, No. 3, 2005, 11 pages (with partial English language translation).

Daniel Oertli, et al., "Rapid Induction of Specific Cytotoxic T Lymphocytes Against Melanoma-Associated Antigens by a Recombinant Vaccinia Virus Vector Expressing Multiple Immunodominant Epitopes and Costimulatory Molecules in Vivo" Human Gene Therapy, vol. 13, 2002, pp. 569-575.

Roy Lau, et al., "Phase I Trial of Intravenous Peptide-Pulsed Dendritic Cells in Patients With Metastatic Melanoma" Journal of Immunotherapy, vol. 24, No. 1, 2001, pp. 66-78.

Combined Office Action and Search Report dated Jul. 16, 2015 in Chinese Patent Application No. 201280042412.0 (with English language translation).

Oleg Y. Borbulevych, et al., "Structures of native and affinity-enhanced WT1 epitomes bound to HLA-A*0201: implications for WT1-based cancer therapeutics" Mol Immunol, vol. 47, No. 15, Sep. 2010, pp. 1-13.

Office Action dated Aug. 20, 2015, in co-pending U.S. Appl. No. 14/184,816.

V. Kasprowicz et al., "A Highly Restricted T-Cell Receptor Dominates the CD8+ T-Cell Response to Parvovirus B19 Infection in HLA-A*2402-Positive Individuals", Journal of Virology, vol. 80, No. 13, Jul. 2006, pp. 6697-6701.

Office Action dated Nov. 16, 2015 in co-pending U.S. Appl. No. 14/687,628.

Office Action dated Dec. 2, 2015 in co-pending U.S. Appl. No. 10/562,486.

(56) References Cited

OTHER PUBLICATIONS

Masashi Gotoh, et al., "Development of HLA-A2402/K$^b$ Transgenic Mice" International Journal of Cancer, vol. 100, No. 5, 2002, pp. 565-570.
Final Office Action in U.S. Appl. No. 14/129,695, dated Jan. 7, 2016.
Kruger et al., "Lessons to be learned from primary renal cell carcinomas: novel tumor antigens and HLA ligands for immunotherapy" 54 Cancer Immunology and Immunotherapy 826-836 (2005).
Robinson et al., "IMGT/HLA Database—a sequence database for the human majore histocompatibility complex" 55 Tissue Antigens 280-287 (2000).
Office Action dated Feb. 14, 2016 in Chinese Patent Application No. 201280042412.0 (with English language translation).
Japanese Office Action dated Apr. 26, 2016 in Patent Application No. 2013-522787 (with English language translation).
Summons to attend oral proceedings pursuant to Rule 115(1) EPC issued on May 2, 2016 in European Patent Application No. 08720964.9.
Office Action dated May 12, 2016 in co-pending U.S. Appl. No. 14/684,628.
Office Action dated Jul. 12, 2016 in Japanese Patent Application No. 2015-151065 (with Partial English language translation).
Kato,T., et al., "Analysis of Accumulated T Cell Clonotypes in Patients with Systemic Lupus Erythematosus", Arthritis & Rheumatism, vol. 43, No. 12, pp. 2712-2721, (Dec. 2000).
Valmori, D., et al., "Vaccination with a Melan-A Peptide Selects an Oligoclonal T Cell Population with Increased Functional Avidity and Tumor Reactivity", The Journal of Immunology, vol. 168, pp. 4231-4240, (2002).
Dietrich, P., et al., "Melanoma Patients Respond to a Cytotoxic T Lymphocyte-defined Self-Peptide with Diverse and Nonoverlapping T-Cell Receptor Repertoires", Cancer Research, vol. 61, pp. 2047-2054, (Mar. 1, 2001).
Coulie, P. G., et al., "A monoclonal cytolytic T-lymphocyte response observed in a melanoma patient vaccinated with a tumor-specific antigenic peptide encoded by gene MAGE-3", vol. 98, No. 18, pp. 10290-10295, (Aug. 28, 2001).
Godelaine, D., et al., "Polyclonal CTL Responses Observed in Melanoma Patients Vaccinated with Dendritic Cells Pulsed with a MAGE-3.A1 Peptide", The Journal of Immunology, vol. 171, pp. 4893-4897, (2003).
Mandruzzato, S., et al., "Large and Dissimilar Repertoire of Melan-A/MART-1-Specific CTL in Metastatic Lesions and Blood of a Melanoma Patient", The Journal of Immunology, vol. 169, pp. 4017-4024, (2002).
International Search Report dated Aug. 7, 2012 in PCT/JP12/065707 Filed Jun. 20, 2012.
Office Action dated May 6, 2014 in European Appln. No. 08720964.9.
International Report on Patentability issued in corresponding PCT/JP2012/065707 dated Jan. 7, 2014 (w/English translation).
Office Action issued in U.S. Appl. No. 12/529,701 dated Feb. 1, 2012.
Hirschhorn et al. "A comprehensive review of genetic association studies", Genetics in Medicine, Mar./Apr. 2002, vol. 4, No. 2, pp. 45-61.
Ioannidis et al. "Replication validity of genetic association studies", Nature Genetics, vol. 29, Nov. 2001, pp. 306-309.
Office Action issued in U.S. Appl. No. 12/529,701 dated Aug. 8, 2012.
Office Action issued in U.S. Appl. No. 12/529,701 dated Aug. 22, 2013.
Office Action issued in U.S. Appl. No. 12/529,701 dated Feb. 14, 2014.
O'Keefe et al. "Molecular Analysis of TCR Clonotypes in LGL: A Clonal Model for Polyclonal Responses", The Journal of Immunology, 2004, vol. 172, No. 3, pp. 1960-1969.

Farina et al. "Conserved TCR usage by HLA-Cw*1601-restricted T cell clones recognizing melanoma antigens", International Immunology, 1996, vol. 8, No. 9, pp. 1463-1466.
Oka et al. "Wilms Tumor Gene Peptide-Based Immunotherapy for Patients with Overt Leukemia from Myelodysplastic Syndrome (MDS) or MDS with Myelofibrosis", International Journal of Hematology, 2003, vol. 78, No. 1, pp. 56-61.
Oka et al. "Induction of WT1 (Wilms' tumor gene)-specific cytotoxic T lymphocytes by WT1 peptide vaccine and the resultant cancer regression", Proc. The National Academy of Sciences of the USA, Sep. 21, 2004, vol. 101, No. 38, pages.
Extended European Search Report issued in corresponding EP application No. 08720964.9 dated Mar. 5, 2010.
Coppage et al. "In vitro generation of tumor specific T cells that recognize a shared antigen of AML: Molecular characterization of TCR genes", Leukemia Research 31, 2007, pp. 195-202.
Zhou et al. Database Genbank, 2003, XP-002569162.
Rezvani et al. "T-Cell Responses Directed against Multiple HLA-A*0201-Restricted Epitopes Derived from Wilms' Tumor 1 Protein in Patients with Leukemia and Healthy Donors: Identification, Quantification, and Characterization", Clinical Cancer Research Dec. 15, 2005, vol. 11, No. 24, pp. 8799-8807.
Ohminami et al. "HLA class I-restricted lysis of leukemia cells by a CD8+ cytotoxic T-lymphocyte clone specific for TW1 peptide", Blood, Jan. 1, 2000, vol. 95, No. 1 XP 002190642, pp. 286-293.
Halapi et al. "T cell receptor usage in malignant diseases", Springer Seminars in Immunopathology (1999), vol. 21, No. 1, pp. 19-35 XO-002568655.
Office Action issued in European patent application No. 08720964.9 dated May 10, 2011.
Correspondence dated Nov. 15, 2012 forwarding and describing the Office Action issued in Mexican patent application No. MX/A/2009/009589.
Office Action issued in European patent application No. 08720964.9 dated Oct. 15, 2012.
Office Action issued in Australian patent application No. 2008222061 dated Nov. 27, 2012.
Xue et al. "Elimination of human leukemia cells in NOD/SCID mice by WT1-TCR gene-transduced human T cells", Blood, 2005, 106, pp. 3062-3067.
Armstrong et al. "Conformational changes and flexibility in T-cell receptor recognition of peptide-MHC complexes", Biochem J., 2008, 415, pp. 183-196.
Office Action issued in Japanese patent application No. 2009-502541 dated Apr. 16, 2013 and partial English translation.
Office Action issued in Australian patent application No. 2008222061 dated May 31, 2013.
Office Action issued in Australian patent application No. 2008222061 dated Oct. 23, 2013.
T cell receptor beta chain variable region [*Homo sapiens*], GenBank: ABF14434.1, 2006.
T cell receptor beta chain [Homo sapiens], GenBank: BAC01035.1, 2002.
"AICAR transformylase PurH [Helicobacter hepaticus ATCC 51449", GenBank: AAP77080.1, Mar. 11 2010.
"*Homo sapiens* T cell receptor beta chain (BV16S1) mRNA, partial cds", GenBank: AF317601.1, 2001.
"T-cell receptor beta-chain [*Homo sapiens*]", GenBank CAC06601.1, 2001.
"T cell receptor beta chain [*Homo sapiens*]", GenBank: AAG15764.1, 2000.
"T cell receptor beta chain, partial [*Homo sapiens*]", GenBank: AAC52008.1, 1998.
Office Action issued in Australian patent application No. 2008222061 dated Dec. 20, 2013.
Abbey et al., "Expression of T-cell receptor genes during early T-cell development", Immunology and Cell Biology, 2008, 86, pp. 166-174.
Office Action issued in Japanese patent application No. 2009-502541 dated Feb. 4, 2014 with partial English translation.
Combined Chinese Office Action and Search Report dated Nov. 4, 2014 in Patent Application No. 201280042412.0 (with English language translation).

(56) References Cited

OTHER PUBLICATIONS

Partial Supplementary European Search Report dated Nov. 27, 2014 in Patent Application No. 12803980.7.
Partial Supplementary European Search Report dated Jan. 5, 2015 in Patent Application No. 12803980.7.
Sebastian Ochsenreither, ""Wilms Tumor Protein 1" (WT1) Peptide Vaccination-induced Complete Remission in a Patient With Acute Myeloid Leukemia Is Accompanied by the Emergence of a Predominant T-cell Clone Both in Blood and Bone Marrow" Journal of Immunotherapy, vol. 34, No. 1, XP009181179, Jan. 2011, pp. 85-91.
Sebastian Ochsenreither, "Wilms' tumor protein 1 (WT1) peptide vaccination in AML patients: predominant TCR CDR3β sequence associated with remission in one patient is detectable in other vaccinated patients" Cancer Immunol Immunother, vol. 61, XP35018866, 2012, pp. 313-322.
Non-Final Office Action dated Nov. 2, 2016 issued in related U.S. Appl. No. 14/184,816.
Final Office Action dated Dec. 2, 2016 issued in U.S. Appl. No. 14/687,628 filed Apr. 15, 2015.
Office Action dated Dec. 5, 2016 issued in European Patent Application No. 12803980.7, which is related to U.S. Appl. No. 14/129,695.
Final Office Action dated Jan. 20, 2017 issued in related U.S. Appl. No. 14/129,695.
Final Office Action dated Feb. 9, 2017 issued in related U.S. Appl. No. 14/184,979.
Sommer et al.—"Minimal homology requirements for PCR primers", Nucleic Acids Research, vol. 17, No. 16, 1989.
Office Action dated Feb. 9, 2017 issued in corresponding Chinese patent application No. 201280042412.0 (with English translation).
Final Office Action dated May 9, 2017 issued in related U.S. Appl. No. 14/184,816.
Final Office Action dated May 10, 2017 issued in related U.S. Appl. No. 12/529,701.
Office Action dated Jul. 18, 2017 issued in corresponding Japanese patent application No. 2015-151065 (with English translation).
Office Action dated Aug. 22, 2017 issued in corresponding Japanese patent application No. 2016-193222 (with English translation).
Office Action dated Nov. 1, 2017 issued in corresponding Chinese patent application No. 201310258589.0 (with English translation).
Yangqui Li et al.—"The feature of CDR3 sequence of TCR VB 21 oligoclonal T cells in CML" Immunological Journal vol. 16, No. 3, May 2000, pp. 189-192.
Non-Final Office Action dated Aug. 24, 2017 issued in related U.S. Appl. No. 14/687,628.
Office Action dated May 29, 2018 in Japanese Patent Application No. 2016-193222 with partial English translation.

Kawakami, Y. "Recent progress in the development of immunotherapy for melanoma", Skin Cancer, vol. 19, No. 1, 2004, pp. 25-33 (with English Abstract).
Combined Canadian Office Action and Search Report dated Mar. 29, 2018 in Canadian Patent Application No. 2,679,045, 6 pages.
Kurokawa, T., et al., "Induction and Clonal Expansion of Tumor-Specific Cytotoxic T Lymphocytes from Renal Cell Carcinoma Patients after Stimulation with Autologous Dendritic Cells Loaded with Tumor Cells", International Journal of Cancer, vol. 91, 2001, pp. 749-756 with cover page.
Hodges, E., et al.. "Diagnostic Role of Tests for T Cell Receptor (TRC) Genes", J Clin. Pathol., vol. 56, 2003, pp. 1-11.
Non-Final Office Action dated Jun. 20, 2018 issued in corresponding U.S. Appl. No. 10/562,486.
Brenchley et al.—"Expansion of activated human naïve T-cells precedes effector function", Clin Exp Immunol 2002, 130, pp. 431-440.
Pittet et al.—"Melan-A/MMART-1-specific CD8 T cells: from thymus to tumor", TRENDS in Immunology, vol. 23, No. 7, Jul. 2002, pp. 325-328.
Powell Jr. et al.—"Phenotypic and Functional Maturation of Tumor Antigen-Reactive CD8+ T Lymphocytes in Patients Undergoing Multiple Course Peptide Vaccination" J Immunother, vol. 27, No. 1, Jan./Feb. 2004, pp. 36-47.
P. Lee et al.—"Characterization of circulating T cells specific for tumor-associates antigens in melanoma patients", Nature Medicine, vol. 5, No. 6, Jun. 1999, pp. 677-685.
Yu et al.—"Cancer vaccines: progress reveals new complexities", The Journal of Clinical. Investigation. Aug. 2002, vol. 110, No. 3, pp. 289-294.
Meidenbauer et al.—"Direct visualization of antigen-specific T cells using peptide-MHC-class I tetrameric complexes", Methods 31 (2003), pp. 160-171.
Andersen et al.—"Poor correspondence between predicted and experimental binding of peptides to class I MHC molecules", Tissue Antigens, 2000, 55. pages 519-531.
Partial Search Report dated Jan. 24, 2019 issued in corresponding European patent application No. 18193944.8.
Extended European Search Report dated May 16, 2019 issued in corresponding European patent application No. 19150097.4.
Decision on Rejection dated Jan. 17, 2020 issued in corresponding Chinese patent application No. 201710368609.8 (with English translation).
Frontier of Tumor Study, vol. 1, pp. 22-25 (with English translation).

\* cited by examiner

| name | Cell# | TRBV | TRBJ | TRBD | CDR3 | CDR3 amino acids |
|------|-------|------|------|------|------|------------------|
| HD-1 | 28 | TRBV10-3*01 | TRBJ1-6*01 | TRBD1*01 | tgt gcc atc agg gag gac agg cgg agt tca ccc ctc cac ttt | CAIREDRRSSPLHF |
| HD-1 | 3 | TRBV4-1*01 | TRBJ1-5*01 | TRBD1*01 | tgc gcc agc agc caa gat cag cag ggg gtg atg gtt tta gcg cag ccc cag cat ttt | CASSQDQQGVMVLAQPQHF |
| HD-1 | 13 | TRBV27*01 | TRBJ1-4*01 | TRBD1*01 | tgc gcc agc ggg gac agg gag aat gaa aaa ctg ttt ttt | CASGDRENEKLFF |
| HD-1 | 44 | TRBV9*01 | TRBJ1-7*01 | TRBD1*01 | tgc gcc agc gga cag ggg gcc tac gag cag tac | CASQGAYEQYF |
| HD-1 | 14—1 | TRBV19*01 | TRBJ2-3*01 | TRBD2*02 | tgc gcc agt atg ggt ttc ggg agt gcg aca gat acg cag tat ttt | CASMGFGSATDTQYF |
| HD-1 | 16 | TRBV2*01 | TRBJ1-1*01 | TRBD1*01 | tgc gcc agc aga acg gac ggg tcg gag acc cag ttc | CASRGEGLEAFF |
| HD-1 | 25—1 | TRBV28*01 | TRBJ2-5*01 | TRBD1*01 | tgt gcc agc agc acg gac agc gag acc cag tac ttc | CASRTDGSETQYF |
| HD-1 | 2—2 | TRBV13*01 | TRBJ2-7*01 | TRBD1*01 | tgt gcc agc agc gcg gga cag ccg gga agc tac gag cag tac ttc | CASSAGGPGSYEQYF |
| HD-1 | 37 | TRBV2*01 | TRBJ2-6*01 | TRBD2*01 | tgt gcc agc agt gaa gcg ctt atg aca ttc tac gag cag tac ttc | CASSEALMTFYEQYF |
| HD-1 | 11 | TRBV6-1*01 | TRBJ1-2*01 | TRBD1*01 | tgt gcc agc agt gaa gag gca ggg gcc gca tct ggc tac acc ttc | CASSEEAGGASGYTF |
| HD-1 | 39 | TRBV5-1*01 | TRBJ1-1*01 | TRBD2*02 | tgc agc agc agc ttt agc ggg agt ggt aac att ggg cag ttc ttc | CASSFSGSGNIEQFF |
| HD-1 | 11' | TRBV27*01 | TRBJ2-7*01 | TRBD1*01 | tgt gcc agc agt ttc act ctc ggg aca ggg ggg aac gag cag tac ttc | CASSFTLGTGNEQYF |
| HD-1 | 31-1' | TRBV19*01 | TRBJ2-3*01 | TRBD2*02 | tgt gcc agt agt ata ggg aca ggg ggt ttc ttc gcg aat acg cag tat ttt | CASSIGTGFFANTQYF |
| HD-1 | 5 | TRBV3-1*01 | TRBJ1-7*01 | TRBD2*02 | tgt gcc agc agc tta gcg cag ggg gga ggg atc tcc tac gag cag tac ttc | CASSLAGGISYEQYF |
| HD-1 | 34 | TRBV7-9*01 | TRBJ2-3*01 | TRBD1*01 | tgt gcc agc agc tta gcg cag ggg gga gac aca gat acg cag tat ttt | CASSLAQGGDTDTQYF |
| HD-1 | 24' | TRBV5-1*01 | TRBJ2-1*01 | TRBD2*01 | tgc gcc agc agc ttg ggc cct tct ctt cta gcg gag gtg ggc aat gag cag ttc ttc | CASSLGPSLLAEVGNEQFF |
| HD-1 | 41 | TRBV7-9*01 | TRBJ1-4*01 | TRBD1*01 | tgt gcc agc agc ttg ggg cag ggg gga gaa aaa ctg ttt ttt | CASSLGQGEEKLFF |
| HD-1 | 1—1 | TRBV19*01 | TRBJ1-1*01 | TRBD2*01 | tgt gcc agt agt ctc ggg acg gtg aac act gaa gct ttc ttt | CASSLGTVNTEAFF |
| HD-1 | 52 | TRBV7-9*01 | TRBJ2-1*01 | TRBD2*01 | tgt gcc agt agt tta aga gcg aac aat cgg tac gag cag tac ttc | CASSLRANNEQFF |
| HD-1 | 6 | TRBV19*01 | TRBJ2-7*01 | TRBD2*01 | tgt gcc agt agt ctt tca gaa att cgg tac gag cag tac ttc | CASSLSEIRYEQYF |
| HD-1 | 46 | TRBV9*01 | TRBJ2-3*01 | TRBD2*01 | tgc gcc agc tta tcc ggg gcc cct aga tca gat acg cag tat ttt | CASSLSGAPRSDTQYF |
| HD-1 | 8 | TRBV7-3*01 | TRBJ1-6*01 | TRBD1*01 | tgc gcc agc tta tct ttg gga ggg gag agt tca ccc ctc cac ttt | CASSLSLGGESSPLHF |
| HD-1 | 47 | TRBV6-2*01 | TRBJ2-1*01 | TRBD2*02 | tgt gcc agc agc ccc gat agc ggg aag aac acc ggg gag ctg ttt ttt | CASSPDSGKNTGELFF |
| HD-1 | 43 | TRBV2*01 | TRBJ1-5*01 | TRBD1*01 | tgt gcc agc ccg ggg gta agt cag ccc cag cat ttt | CASSPGVSQPQHF |
| HD-1 | 48 | TRBV3-1*01 | TRBJ1-4*01 | TRBD2*01 | tgt gcc agc agc ccc cca ccc cca gga gga gac tgg aat gag ctg ttt ttt | CASSPPPGGEKLFF |
| HD-1 | 51 | TRBV7-2*02 | TRBJ2-1*01 | TRBD2*02 | tgt gcc agc agc ccc cag gga gac tgg aat gag cag ttc ttc | CASSPQDWNEQFF |
| HD-1 | 45 | TRBV4-1*01 | TRBJ2-7*01 | TRBD2*01 | tgt gcc agc agc ccc cag cta gcg gag cgc tcc tac gag cag tac ttc | CASSPQLAERSYEQYF |
| HD-1 | 32 | TRBV3-1*01 | TRBJ2-2*01 | TRBD1*01 | tgt gcc agc agc ccg aga gga ggg ggc ggc gag ctg ttt ttt | CASSPRAGAGGELFF * |
| HD-1 | 49 | TRBV3-1*01 | TRBJ2-2*01 | TRBD2*01 | tgt gcc agc agc ccg aga gga ggg ggc ggc gag ctg ttt ttt | CASSPRAGAGGELFF * |
| HD-1 | 40—1 | TRBV3-1*01 | TRBJ2-2*01 | TRBD2*01 | tgt gcc agc agc ccg cga tcc ccc ggg act cgg gga gac gag cag tac ttc | CASSPRSPGTSGDEQYF |
| HD-1 | 4 | TRBV5-5*01 | TRBJ2-7*01 | TRBD2*01 | tgt gcc agc agc cct cga ggg acc ccc agg gcc ggg gag ctg ttt ttt | CASSPTPRPGELFF |
| HD-1 | 23 | TRBV4-3*01 | TRBJ1-2*01 | TRBD1*01 | tgc gcc agc agc ccg cca tgg aca ggg tcc gag cag tac ttc | CASSPWGTGSEQYF |
| HD-1 | 20 | TRBV9*01 | TRBJ2-6*01 | TRBD1*01 | tgt gcc agc agc gta gac tat cgg ggg aac gtc ctg act ttc | CASSVDYRGNGQPQHF |
| HD-1 | 29' | TRBV4-1*01 | TRBJ2-1*01 | TRBD1*01 | tgc gcc agc agc cag ggg gca gct ggg gcc aac tac gag cag ttc ttc | CASSQGAAGANVLTF |
| HD-1 | 25—2 | TRBV23-1*01 | TRBJ2-1*01 | TRBD2*02 | tgc gcc agc agt cag gga ggg gag gtg gat gag cag ttc ttc | CASSQGGEVDEQFF |
| HD-1 | 12 | TRBV23-1*01 | TRBJ2-1*01 | TRBD2*01 | tgc gcc agc agt caa tct gcc ccc ggg ttg gtt gac aat gag cag ttc ttc | CASSQSAPGLVDNEQFF |
| HD-1 | 9—2 | TRBV4-2*01 | TRBJ2-5*01 | TRBD2*01 | tgc gcc agc agt caa atg acc agc gcc gag acc cag tac ttc | CASSQSMTSAETQYF |
| HD-1 | 50 | TRBV4-1*01 | TRBJ2-1*01 | TRBD2*02 | tgc gcc agc agt tat agg gac gtc gcc tac gag cag ttc | CASSSSGTTGELFF |
| HD-1 | 27 | TRBV6-1*01 | TRBJ1-1*01 | TRBD2*01 | tgt gcc agc agc acc gag ccc cct gac agg gcc act gaa gct ttc ttt | CASTEPPDRATEAFF |
| HD-1 | 22—1 | TRBV5-8*01 | TRBJ2-7*01 | TRBD2*02 | tgt gcc agc acc ctg gac tct aat aat gag cag ttc ttc | CASTLDGSNNEQFF |
| HD-1 | 2' | TRBV27*01 | TRBJ2-2*01 | TRBD1*01 | tgc gcc agc act acc tca tta gac gag cag ggg cgc acc ggg cgc ctg ttt | CATSDEGGGARTGELFF |
| HD-1 | 38 | TRBV15*01 | TRBJ1-1*01 | TRBD1*01 | tgc gcc tgg agt ccc ccc gga gct cta acc tac gag cag tac ttc | CAWSPPGTLTYEQYF |
| HD-1 | 29 | TRBV20-1*01 | TRBJ2-3*01 | TRBD2*02 | tgc agt gct ccc ggg act agc ggg agc ggg gga ata gat acg cag tat ttt | CSAPGTSGSGGIDTQYF |
| HD-1 | 31 | TRBV20-1*01 | TRBJ2-1*01 | TRBD1*01 | tgc agt gct aga ttc cag tac aat gag cag ttc ttc | CSARFQYNEQFF |
| HD-1 | 33 | TRBV20-1*01 | TRBJ1-1*01 | TRBD1*01 | tgc agt gct agg ttg aca ggg ggt gag acc gaa gct ttc ttt | CSARTGGETEAFF |
| HD-1 | 26 | TRBV20-1*01 | TRBJ2-2*01 | TRBD1*01 | tgc agt gcc aga cca gga cag gca tac aat gag cag ttc ttc | CSARPGGAYNEQFF |
| HD-2 | 50 | TRBV10-3*01 | TRBJ1-1*01 | TRBD1*01 | tgt gcc atc agg gcc ggg ggc gcg gtg ggg act gaa gct ttc ttt | CAIRAGTGGAVGTEAFF |
| HD-2 | 33 | TRBV27*01 | TRBJ2-3*01 | TRBD2*02 | tgt gcc agc ctc tcc cgg agg gct ccc tta gat acg cag tat ttt | CASLSREAPLDTQYF |
| HD-2 | 30 | TRBV19*01 | TRBJ2-1*01 | TRBD1*01 | tgc agt gcc agt agg gga cag ggg gcg cgt aat gag cag ttc ttc | CASRGGARNEQFF |
| HD-2 | 47 | TRBV28*01 | TRBJ2-1*01 | TRBD1*01 | tgt gcc aga cca gga cag gca tac aat gag cag ttc ttc | CASRPGGAYNEQFF |

Fig. 2B

| | | TRBV | TRBJ | TRBD | CDR3 nucleotide | CDR3 amino acid |
|---|---|---|---|---|---|---|
| HD-2 | 25 | TRBV27*01 | TRBJ2-7*01 | TRBD2*02 | tgt gcc agc cgc ccc agt tgg cgg gaa gga agc gag cag tac ttc | CASRPSWREGEQYF |
| HD-2 | 24 | TRBV5-4*01 | TRBJ2-3*01 | TRBD1*01 | tgc gcc agc aga caa aca ggt ctc ctc aca gat acg cag tat ttt | CASRQTGLLTDTQYF |
| HD-2 | 14 | TRBV27*01 | TRBJ2-3*01 | TRBD2*02 | tgt gcc agc cgt agc ggg acg ggc aca gat acg cag tat ttt | CASRSGTGTDTQYF |
| HD-2 | 35 | TRBV9*01 | TRBJ2-5*01 | TRBD2*01 | tgt gcc agc agc gcc ccg tac ggg ggg gag acc cag tac ttc | CASSAPYGGETQYF |
| HD-2 | 23 | TRBV2*01 | TRBJ2-5*01 | TRBD2*01 | tgt gcc agc agt gca aga ctc aat gtg gag acc cag tac ttc | CASSARLNVETQYF |
| HD-2 | 40 | TRBV19*01 | TRBJ2-1*01 | TRBD2*01 | tgt gcc agt agt gct agc gga gcg agc tcc tac aat gag cag ttc ttc | CASSASGASSYNEQFF |
| HD-2 | 29 | TRBV2*01 | TRBJ2-1*01 | TRBD2*01 | tgt gcc agc agt gac gcc gcg gct acc aat tac gag cag tac ttc | CASSDAAATNYEQYF |
| HD-2 | 45 | TRBV2*01 | TRBJ2-5*01 | TRBD2*01 | tgt gcc agc agt gaa gat cgg cag agg acg gat gag acc cag tac ttc | CASSEDRQRTDETQYF |
| HD-2 | 22 | TRBV6-1*01 | TRBJ2-1*01 | TRBD1*01 | tgt gcc agc agt gaa gaa ggg act agc gcc tac aat gag cag ttc ttc | CASSEEGGTSAYNEQFF |
| HD-2 | 1 | TRBV27*01 | TRBJ2-5*01 | TRBD1*01 | tgt gcc agc agc gaa ttt gta cag gag acc cag tac ttc | CASSEFVQETQYF |
| HD-2 | 39 | TRBV10-2*01 | TRBJ1-5*01 | TRBD1*01 | tgt gcc agc agt gag tct atg ggg ggg agt cag ccc cag cat ttt | CASSESMGGSQPQHF |
| HD-2 | 54 | TRBV5-1*01 | TRBJ2-1*01 | TRBD2*02 | tgc gcc agc agc ttt att gag ggg gag cag ttc ttc | CASSFIEGEQFF |
| HD-2 | 37 | TRBV5-1*01 | TRBJ2-1*01 | TRBD2*01 | tgc gcc agc agc ggc ctc tct ggg gat gag cag ttc ttc | CASSGGLSGDEQFF |
| HD-2 | 21 | TRBV19*01 | TRBJ2-1*01 | TRBD2*02 | tgt gcc agt agt ata ggt ggc ggg agg tgg aac aat gag cag ttc ttc | CASSIGGGRWNNEQFF |
| HD-2 | 6 | TRBV19*01 | TRBJ2-1*01 | TRBD2*01 | tgt gcc agc agt ata cgg ggc tac ctc tcc tac aat gag cag ttc ttc | CASSIRGYLSYNEQFF |
| HD-2 | 5 | TRBV7-9*01 | TRBJ2-5*01 | TRBD2*01 | tgt gcc agc agc ttg gct agc ggg caa gag acc cag tac ttc | CASSLASGQETQYF |
| HD-2 | 61 | TRBV27*01 | TRBJ1-1*01 | TRBD1*01 | tgt gcc agc agt tta ttt ggc cag gtc ggg ttt act gaa gct ttc | CASSLFGQVGFTEAFF |
| HD-2 | 9 | TRBV5-6*01 | TRBJ2-7*01 | TRBD1*01 | tgt gcc agc agc ttg ggg gcg agt cgc tac cag tac ttc | CASSLGASRYEQYF |
| HD-2 | 2 | TRBV27*01 | TRBJ2-2*01 | - | tgt gcc agc agt ttg cat acc ggg gag ctg ttt ttt | CAIRLHTGELFF |
| HD-2 | 17 | TRBV27*01 | TRBJ2-1*01 | TRBD1*01 | tgt gcc agc agt tta atc gga cag att gag cag ttc ttc | CASSLIGQIEQFF |
| HD-2 | 59 | TRBV11-2*01 | TRBJ2-3*01 | TRBD2*02 | tgt gcc agc agc ttg ttg cta gcg gga ggg cct agc aca gat acg cag tat ttt | CASSLLLAGGPSTDTQYF |
| HD-2 | 38 | TRBV27*01 | TRBJ2-1*01 | TRBD2*01 | tgt gcc agc agt tta cta cct cgg cag gcc ccg ggg aat gag cag ttc ttc | CASSLLPRQAPGNEQYF |
| HD-2 | 49 | TRBV4-1*01 | TRBJ2-7*01 | TRBD1*01 | tgc gcc agc agc ctg act cag gcg gga cag agc cca gcc tac gag cag tac ttc | CASSLTQAGQSPAYEQYF |
| HD-2 | 7 | TRBV11-2*01 | TRBJ1-1*01 | TRBD1*01 | tgt gcc agc agc tta gta cta gga tac act gaa gct ttc ttt | CASSLVLGYTEAFF* |
| HD-2 | 42 | TRBV11-2*01 | TRBJ1-1*01 | TRBD1*01 | tgt gcc agc agc tta gta cta gga tac act gaa gct ttc ttt | CASSLVLGYTEAFF* |
| HD-2 | 31 | TRBV28*01 | TRBJ1-1*01 | TRBD2*01 | tgt gcc agc agt tta gtt cca ggg agg aac act gaa gct ttc ttt | CASSLVPGRNTEAFF |
| HD-2 | 18 | TRBV7-9*01 | TRBJ2-7*01 | TRBD2*01 | tgt gcc agc agc tta tgg gac gac cag tac ttc | CASSLWDDEQYF |
| HD-2 | 41 | TRBV18*01 | TRBJ2-1*01 | TRBD1*01 | tgt gcc agc tca cct gag ggg ggc ccc acg cag tat ttt | CASSPEGGPTQYF* |
| HD-2 | 53 | TRBV27*01 | TRBJ2-3*01 | TRBD2*01 | tgt gcc agc tca cct gag ggg ggc ccc acg cag tat ttt | CASSPEGGPTQYF* |
| HD-2 | 43 | TRBV5-5*01 | TRBJ2-5*01 | TRBD2*02 | tgt gcc agc cct gaa tta gcg gga ggt ctt ttg gag acc cag tac ttc | CASSPELAGGLLETQYF** |
| HD-2 | 52 | TRBV5-5*01 | TRBJ2-5*01 | TRBD2*02 | tgt gcc agc cct gaa tta gcg gga ggt ctt ttg gag acc cag tac ttc | CASSPELAGGLLETQYF** |
| HD-2 | 55 | TRBV6-6*01 | TRBJ2-7*01 | TRBD1*01 | tgt gcc agc agc ccc tcc ggg aac atc gag cag tac ttc | CASSPSGNIEQYF |
| HD-2 | 57 | TRBV28*01 | TRBJ1-2*01 | TRBD1*01 | tgt gcc agc agt cca tcc cct gca ggg gcc tat ggc tac acc ttc | CASSPSPAGAYGYTF |
| HD-2 | 26 | TRBV3-1*01 | TRBJ2-2*01 | TRBD2*02 | tgt gcc agc agc cag agt tca cta gcg gga ggg ccc agc ggg gag ctg ttt ttt | CASSQSSLAGGPSGELFF |
| HD-2 | 48 | TRBV3-1*01 | TRBJ2-3*01 | TRBD1*01 | tgt gcc agc agc caa acc ggg tca cct caa atc aca gat acg cag tat ttt | CASSQTGSPQITDTQYF |
| HD-2 | 51 | TRBV28*01 | TRBJ2-7*01 | TRBD2*01 | tgt gcc agc agt tct ctg ggg gag cag tac ttc | CASSSLGEQYF |
| HD-2 | 38-2 | TRBV11-1*01 | TRBJ2-7*01 | TRBD1*01 | tgt gcc agc agt tcc ccc ggg gaa ata cag gtg acc tac gag cag tac ttc | CASSSPGEIQVTYEQYF |
| HD-2 | 20 | TRBV28*01 | TRBJ2-7*01 | TRBD2*01 | tgt gcc agc agt tcc cag gac tcc tac gag cag tac ttc | CASSSQDSSYEQYF |
| HD-2 | 19 | TRBV9*01 | TRBJ2-1*01 | - | tgt gcc agc agc gta gct tcc ccc ggg gag ctg ttt ttt | CASSVASPGELFF |
| HD-2 | 4 | TRBV9*01 | TRBJ2-2*01 | TRBD2*01 | tgt gcc agc agc gta gtt tcg gga acc ggg gag ctg ttt ttt | CASSVVSGTGELFF |
| HD-2 | 56 | TRBV27*01 | TRBJ2-7*01 | TRBD1*01 | tgt gcc agt tgg ggg ggg ggg ggt tct atc tac gag cag tac ttc | CASSWGGGGSIYEQYF* |
| HD-2 | 60 | TRBV27*01 | TRBJ2-7*01 | TRBD1*01 | tgt gcc agt tgg ggg ggg ggg ggt tct atc tac gag cag tac ttc | CASSWGGGGSIYEQYF* |
| HD-2 | 16 | TRBV6-6*01 | TRBJ2-7*01 | TRBD1*01 | tgt gcc agc tgc cac gag cag tac ttc | CASSYGHEQYF |
| HD-2 | 11 | TRBV28*01 | TRBJ1-6*01 | TRBD1*01 | tgt gcc agt tac ctg gat gca gga aat tca ccc ctc cac ttt | CASSYLDAGNSPLHF* |
| HD-2 | 28 | TRBV28*01 | TRBJ1-6*01 | TRBD1*01 | tgt gcc agt tac ctg gat gca gga aat tca ccc ctc cac ttt | CASSYLDAGNSPLHF* |
| HD-2 | 58 | TRBV6-5*01 | TRBJ2-7*01 | TRBD1*01 | tgt gcc agc agt tac ctg gac agg ggg ctg ggg gag cag tac ttc | CASSYLDRGLGEQYF |
| HD-2 | 10 | TRBV7-9*01 | TRBJ2-7*01 | TRBD2*01 | tgt gcc agc acc ccg aca ggg aca cgg ctc gtt gag gta acc tac gag cag tac ttc | CASTPTGTRLVEVTYEQYF |
| HD-2 | 15 | TRBV7-9*01 | TRBJ2-1*01 | TRBD2*01 | tgt gcc agc acg cct tgg gcg gac tcc tac aat gag cag ttc ttc | CASTPWADSYNEQFF |
| HD-2 | 13 | TRBV30*01 | TRBJ2-1*01 | TRBD2*02 | tgt gcc tgg agt gta ggt ttc tta gcg gga tac gag cag tac ttc | CAWSVGFLAGYEQYF |
| HD-2 | 36 | TRBV30*01 | TRBJ1-1*01 | - | tgt gcc tgg agt gta ctg tcg gat gag cag ttc ttc | CAWSVLSDEQFF |
| HD-2 | 8 | TRBV20-1*01 | TRBJ2-1*01 | TRBD2*02 | tgt gcc agt gct aga gac ctt agc ggg agc gga gac aat gag cag ttc ttc | CSARDLSGSEDNEQFF |
| HD-2 | 27 | TRBV29-1*01 | TRBJ1-1*01 | TRBD1*01 | tgc agc gtt gaa tt acg gac act gaa gct ttc ttt | CSVEEFTDTEAFF |
| HD-2 | 46 | TRBV29-1*01 | TRBJ1-2*01 | TRBD1*01 | tgc agc gtt gag cag gac aca tat ggc tac acc ttc | CSVEQDTYGYTF |
| HD-3 | 18-1 | TRBV10-3*01 | TRBJ2-1*01 | TRBD1*01 | tgt gcc atc gga gat atg act cgc aat gag cag ttc ttc | CAIRDMTRNEQFF |
| HD-3 | 67' | TRBV19*01 | TRBJ1-2*01 | TRBD1*01 | tgt gcc agc gga ccg cct aac tat ggc tac acc ttc | CASGPPNYGYTF |
| HD-3 | 44' | TRBV27*01 | TRBJ1-5*01 | TRBD1*01 | tgt gcc agc att tta tcc acg gga aac aat cac ccc cag ctt ttt | CASILSTGNNHPQLF |
| HD-3 | 36' | TRBV2*01 | TRBJ2-1*01 | TRBD2*01 | tgt gcc agc aca ggg acc acc agg aac aat gag cag ttc ttc | CASKPQTTRNNEQFF |
| HD-3 | 77' | TRBV6-5*01 | TRBJ2-5*01 | TRBD2*01 | tgt gcc tcc ctt ggg agc ggg caa gag acc cag tac ttc | CASLGSGQETQYF |

Fig. 2C

| | | | | | | |
|---|---|---|---|---|---|---|
| HD-3 | 19' | TRBV19*01 | TRBJ1-6*01 | TRBD1*01 | tgt gcc agt aga gga gcg ggc gcc ctc ttt | CASRGAGALHF |
| HD-3 | 79' | TRBV6-6*01 | TRBJ2-7*01 | TRBD2*01 | tgt gcc agc aga tat ccc cag gac ccc ggg cag tac ttc | CASRYPQDPGQYF |
| HD-3 | 40' | TRBV19*01 | TRBJ1-3*01 | TRBD1*01 | tgt gcc agt agt gcc cgg gga cac tct gga aac acc ata tat ttt | CASSARGHSGNTIYF |
| HD-3 | 25' | TRBV7-9*01 | TRBJ2-5*01 | TRBD2*02 | tgt gcc agc agc ttc ccc ctg agt tcc cta gag acc cag tac ttc | CASSFPLSSLETQYF |
| HD-3 | 89' | TRBV5-4*01 | TRBJ1-2*01 | TRBD1*01 | tgt gcc agc agc ttt tca ggg ggc cat cct atg ggc tac acc ttc | CASSFSGGHPMGYTF |
| HD-3 | 29 | TRBV9*01 | TRBJ2-7*01 | TRBD2*01 | tgt gcc agc agc ggt gag gga cta aac tac gag cag tac ttc | CASSGEGLNYEQYF |
| HD-3 | 48' | TRBV9*01 | TRBJ1-2*01 | TRBD1*01 | t gcc agc agt cac gga cag gcc gct tgg tat ggc tac acc ttc | CASSHGAAWYGYTF |
| HD-3 | 34—1' | TRBV7-2*02 | TRBJ2-1*01 | TRBD2*01 | tgt gcc agc agc cac ggg gtg att tgg agc cct gac acc ggg gag ctg ttt | CASSHGVIWSPDTGELFF |
| HD-3 | 13' | TRBV19*01 | TRBJ2-1*01 | TRBD1*01 | tgt gcc agt agt ata cag gca agc tcc tac aat gag cag ttc ttc | CASSIQASSYNEQFF |
| HD-3 | 7 | TRBV19*01 | TRBJ2-1*01 | TRBD2*01 | tgt gcc agt agt att cgg gcg gac ccc gcc tac aat gag cag ttc ttc | CASSIRADPAYNEQFF |
| HD-3 | 5 | TRBV5-6*01 | TRBJ2-7*01 | TRBD1*01 | tgt gcc agc agc ttg gcg gag ctg ggc cgg gga cgc ctc cat tac gag cag tac ttc | CASSLAELGRGGRLHYEQYF |
| HD-3 | 21' | TRBV7-9*01 | TRBJ2-7*01 | TRBD2*02 | tgt gcc agc agc tta gcg gtt agc ggg agt tcc gac gag cag tac ttc | CASSLAVSGSSDEQYF |
| HD-3 | 91—2' | TRBV11-2*01 | TRBJ2-3*01 | | tgt gcc agc agc tta gat ttc gca gat acg cag tat ttt | CASSLDFADTQYF |
| HD-3 | 2 | TRBV5-1*01 | TRBJ1-3*01 | TRBD1*01 | tgt gcc agc agc ttg gat agg gaa acg ctc tct gga aac acc ata tat ttt | CASSLDRETLSGNTIYF |
| HD-3 | 69 | TRBV12-3*01 | TRBJ1-1*01 | TRBD1*01 | tgt gcc agc agt tta gag ggg gag atg gtt gaa gct ttc ttt | CASSLEGKMVEAFF |
| HD-3 | 53' | TRBV27*01 | TRBJ1-1*01 | TRBD1*01 | tgt gcc agc agt ttg ttc cag gga ggt ccc act gaa gct ttc ttt | CASSLFQGGPTEAFF |
| HD-3 | 22' | TRBV7-9*01 | TRBJ2-1*01 | TRBD2*02 | tgt gcc agc agc tta ggt tto ggg cta gcg gga gac gag cag ttc ttc | CASSLGFGLAGDEQF |
| HD-3 | 78' | TRBV7-9*01 | TRBJ2-6*01 | TRBD1*01 | tgt gcc agc agt tta ggg ttt ggc agg gag gcc aac gtc ctg act ttc | CASSLGFGREANVLTF |
| HD-3 | 30' | TRBV7-9*01 | TRBJ2-5*01 | TRBD2*01 | tgt gcc agc agc ctt gga ttc ggt cgg gag acc cag tac ttc | CASSLGFGRETQYF |
| HD-3 | 65' | TRBV27*01 | TRBJ2-1*01 | TRBD2*01 | tgt gcc agc agt tta ggc ggt ggg tgg aat gag cag ttc ttc | CASSLGGGWNEQFF |
| HD-3 | 56 | TRBV5-4*01 | TRBJ2-7*01 | TRBD2*02 | tgt gcc agc agc ttg ggg cta gcg gga aaa aac gag cag tac ttc | CASSLGLAGKNEQYF |
| HD-3 | 74' | TRBV7-9*01 | TRBJ1-5*01 | TRBD1*01 | tgt gcc agc agc tta ggt ctc ggg ccg caa aac ccc cag cat ttt | CASSLGLGPQNPQHF |
| HD-3 | 63' | TRBV7-9*01 | TRBJ1-4*01 | TRBD2*01 | tgt gcc agc agc tta ggg gtg ggg acg gga ggg gaa aaa ctg ttt ttt | CASSLGVGTEGEKLFF |
| HD-3 | 6 | TRBV5-6*01 | TRBJ2-3*01 | TRBD1*01 | tgt gcc agc agc ttg ctc tcc cgg cca gat acg cag tat ttt | CASSLLSRPDTQYF |
| HD-3 | 9' | TRBV12-3*01 | TRBJ1-2*01 | TRBD2*02 | tgt gcc agc agt tta caa ggg aac acc ggg gag ctg ttt ttt | CASSLQGNTGELFF |
| HD-3 | 33' | TRBV11-1*01 | TRBJ2-7*01 | TRBD1*01 | tgt gcc agc agt tta gtt gga acg tcc gag cag tac ttc | CASSLVGTSYEQYF |
| HD-3 | 49 | TRBV27*01 | TRBJ2-1*01 | TRBD2*02 | tgt gcc agt ccc gac cgg agc tcc tac aat gag cag ttc ttc | CASSPDRSSYNEQFF |
| HD-3 | 57 | TRBV7-3*01 | TRBJ1-1*01 | TRBD1*01 | tgt gcc agc agc ccg ggg ggc atg gac act gaa gct ttc ttt | CASSPGGMDTEAFF |
| HD-3 | 60 | TRBV7-3*01 | TRBJ2-1*01 | TRBD2*01 | tgt gcc agc agc ccg ggc ggg aat gag cag ttc ttc | CASSPGGNEQFF |
| HD-3 | 35' | TRBV27*01 | TRBJ2-1*01 | TRBD2*01 | tgt gcc agc agc ccg ggg ccc aac aat gag cag ttc ttc | CASSPGPNNEQFF |
| HD-3 | 1 | TRBV7-9*01 | TRBJ2-7*01 | TRBD1*01 | tgt gcc agc agc ccc ggc ccc tac gag cag tac ttc | CASSPGPYEQYF |
| HD-3 | 23 | TRBV27*01 | TRBJ2-1*01 | TRBD2*02 | tgt gcc agc agt ccc cca ggg ata gcg gga gtt aat gag cag ttc ttc | CASSPPGIAGVNEQFF |
| HD-3 | 20 | TRBV7-8*01 | TRBJ2-2*01 | TRBD2*01 | tgt gcc agc agt ccc cct aat cgg cat ccc acc ggg gag ctg ttt ttt | CASSPPNREHGTGELFF * |
| HD-3 | 52 | TRBV7-8*01 | TRBJ2-2*01 | TRBD2*02 | tgt gcc agc agt ccc cca aat cgg cat ccc acc ggg gag ctg ttt ttt | CASSPPNREHGTGELFF * |
| HD-3 | 32 | TRBV7-2*01 | TRBJ2-3*01 | TRBD2*01 | tgt gcc agc agt ccc cca aat cgg gag cag cat cca caa aca gat acg cag tat ttt | CASSPPWRPQTDTQYF |
| HD-3 | 92' | TRBV18*01 | TRBJ2-7*01 | TRBD1*01 | tgc cca ccc gag gac ctc ctc tac tac gag cag tac ttc | CASSPQDLLYYEQYF |
| HD-3 | 26' | TRBV7-7*01 | TRBJ1-4*01 | TRBD2*01 | tgt gct agc agc ccg agt ctc ggt gaa aaa ctg ttt ttt | CASSPSLGEKLFF |
| HD-3 | 47 | TRBV4-1*01 | TRBJ2-7*01 | TRBD1*01 | tgc cag agc agc caa gca ctt tcc tac gag cag tac ttc | CASSQALSYEQYF |
| HD-3 | 54—1' | TRBV4-2*01 | TRBJ1-2*01 | TRBD1*01 | tgt gcc agc agt tat ccg gat ccg gcc tac tat ggc tac acc ttc | CASSQDPAYYGYTF |
| HD-3 | 55' | TRBV3-1*01 | TRBJ2-2*01 | TRBD2*01 | tgt gcc agc caa ctc gac ctc gac cgg acg aac acc ggg gag ctg ttt ttt | CASSQLDRTNTGELFF |
| HD-3 | 58' | TRBV3-1*01 | TRBJ1-1*01 | TRBD1*01 | tgt gcc agc cag tgg gtc ggg ggc act gaa gct ttc ttt | CASSQWVGGTEAFF |
| HD-3 | 75 | TRBV12-3*01 | TRBJ2-3*01 | TRBD1*01 | tgt gcc agc agc cgg aca ggg ggg tac agc agt gat acg cag tat ttt | CASSRSSSSTDTQYF |
| HD-3 | 71' | TRBV11-1*01 | TRBJ1-2*01 | TRBD1*01 | tgt gcc agc agc cgg aca gga ggc tac ggc tac acc ttc | CASSRTGGYTEAFF |
| HD-3 | 85 | TRBV5-1*01 | TRBJ2-7*01 | TRBD2*01 | tgt gcc agc agt tcg gac tcg gac ggc tat ggc tac acc ttc | CASSSDGSGYGYTF |
| HD-3 | 80' | TRBV6-2*01 | TRBJ2-3*01 | TRBD1*01 | tgt gcc agc agt tcg gga cta gca aca gat acg cag tat ttt | CASSSGLATDTQYF |
| HD-3 | 68' | TRBV28*01 | TRBJ2-7*01 | | tgt gcc agc agc ttg acc ctg acc tac gag cag tac ttc | CASSSLTYEQYF |
| HD-3 | 87 | TRBV7-9*01 | TRBJ2-1*01 | TRBD2*01 | tgt gcc agc agc tct cga agg gga ctt gaa gac gag aat gag cag ttc ttc | CASSSRRGLEDNEQFF |
| HD-3 | 4' | TRBV7-9*01 | TRBJ1-3*01 | TRBD1*01 | tgt gcc agc agc tct agg tgg gat gcc tct gga aac acc ctc cac ttt | CASSSRWDASGNTIYF |
| HD-3 | 86' | TRBV27*01 | TRBJ2-7*01 | TRBD1*01 | tgt gcc agc agt acg gcc tac gag cag tac ttc | CASSTAYEQYF |
| HD-3 | 28' | TRBV28*01 | TRBJ1-1*01 | TRBD2*01 | tgt gcc agc agc ctg gtt ggg ggc gct gaa gct ttc ttt | CASSTLVGAAEAFF |
| HD-3 | 12 | TRBV28*01 | TRBJ2-1*01 | TRBD1*01 | tgt gcc agc tcg acc tac aat gag cag ttc ttc | CASSTYNEQFF * |
| HD-3 | 27' | TRBV28*01 | TRBJ2-1*01 | TRBD1*01 | tgt gcc agc tcg acc tac aat gag cag ttc ttc | CASSTYNEQFF * |
| HD-3 | 37' | TRBV6-5*01 | TRBJ1-1*01 | TRBD1*01 | tgt gcc agc agt tgg gga cag gtc att act gaa gct ttc ttt | CASSWGQVITEAFF |
| HD-3 | 17' | TRBV6-5*01 | TRBJ1-6*01 | TRBD1*01 | tgt gcc agc agt tat gga gag aat tca ccc ctc cac ttt | CASSYGEENSPLHF |
| HD-3 | 62 | TRBV6-5*01 | TRBJ2-5*01 | TRBD2*01 | tgt gcc agc agt tac ggg ttg ggt caa gag acc cag tac ttc | CASSYGLGQETQYF |
| HD-3 | 50 | TRBV6-5*01 | TRBJ1-3*01 | TRBD1*01 | tgt gcc agc agt tac ggg tgg gca gcc tct gga aac acc ata tat ttt | CASSYGWAASGNTIYF |
| HD-3 | 43' | TRBV6-2*01 | TRBJ1-4*01 | TRBD1*01 | tgt gcc agc agt tac ctg ggt gca act aat gaa aaa ctg ttt ttt | CASSYLGATNEKLFF |
| HD-3 | 84' | TRBV12-3*01 | TRBJ1-1*01 | TRBD1*01 | tgt gcc agc gac acc gac tct cct gaa aaa ctg ttt ttt | CASTDSPEKLFF |

Fig. 2D

| | | | | | | |
|---|---|---|---|---|---|---|
| HD-3 | 42' | TRBV19*01 | TRBJ1-6*01 | TRBD1*01 | tgt gcc agt acc cag ggg agc tcc aat tca ccc ctc cac ttt | CASTQGSSYNSPLHF |
| HD-3 | 70 | TRBV19*01 | TRBJ2-1*01 | TRBD1*01 | tgt gcc acg gaa gga cag ggt tig ggt gag cag ttc ttc | CATEGGQLGEQFF |
| HD-3 | 72' | TRBV2*01 | TRBJ2-3*01 | TRBD2*02 | tgc acc acc ggt tgg gga gat tct agc aca gat acg cag tat ttt | CATGWGDSSTDTQYF |
| HD-3 | 16 | TRBV24-1*01 | TRBJ1-5*01 | | tgt gcc acc agt gat gcc aac agc aat cag ccc cag cat ttt | CATSDANSNQPQHF |
| HD-3 | 15 | TRBV15*01 | TRBJ2-1*01 | TRBD2*02 | tgt gcc acc agc gag ggc ctc gcg ttg ggt gag cag ttc ttc | CATSEGLALGEQFF |
| HD-3 | 73 | TRBV15*01 | TRBJ2-1*01 | TRBD1*01 | tgt gcc acc agc aga gat agc ata ggg ggc act gag ttc ttc | CATSRDSIGGTEQFF |
| HD-3 | 76 | TRBV28*01 | TRBJ2-2*01 | TRBD2*02 | tgt gcc gtc cag ggc ggg agt agc gga ggg agc ctg ttt ttt | CAVQGGSGTGELFF |
| HD-3 | 81' | TRBV20-1*01 | TRBJ2-3*01 | TRBD2*01 | tgc agt gct ttc cgg ggg gca ggg gac aca gat acg cag tat ttt | CSAFRGAGDTDTQYF |
| HD-3 | 46' | TRBV20-1*01 | TRBJ2-1*01 | TRBD2*02 | tgc agt gcc ttt gtt ggc ggg agg gac tac aat gag cag ttc ttc | CSAFVGGRDYNEQFF |
| HD-3 | 45 | TRBV20-1*01 | TRBJ1-4*01 | TRBD1*01 | tgc agt gcc ccc gag acg gga gct gaa aaa ctg ttt ttt | CSAPTETGAEKLFF |
| HD-3 | 83' | TRBV20-1*01 | TRBJ2-7*01 | TRBD2*01 | tgc agt gct aga gat ttc gga tcg agc tcc tac gag cag ttc ttc | CSARDFGSSSYEQYF |
| HD-3 | 88' | TRBV20-1*01 | TRBJ1-5*01 | TRBD1*01 | tgc agt gct aga gag gac agg gag tat cag ccc cag cat ttt | CSAREDREYQPQHF |
| HD-3 | 59 | TRBV20-1*01 | TRBJ2-7*01 | TRBD2*01 | tgc agt gcg aga gaa ctt ttg ggg gac tcc tac gag cag tac ttc | CSARELLGDSYEQYF |
| HD-3 | 61 | TRBV20-1*01 | TRBJ2-3*01 | TRBD1*01 | tgc agt gac gcg aca ggg gag tca gat acg cag tat ttt | CSDATGESDTQYF |
| HD-4 | 73 | TRBV19*01 | TRBJ2-2*01 | TRBD2*01 | tgt gcc gcg aag atg ggg gtc acc ggg gag ctg ttt ttt | CAAKMGVTGELFF |
| HD-4 | 55 | TRBV27*01 | TRBJ1-1*01 | TRBD1*01 | tgt gcc aac acc ttt gat ccc ccg gga cag ggg aat cct gaa gct ttc ttt | CANTFDPPGQGNPEAFF |
| HD-4 | 90 | TRBV12-3*01 | TRBJ2-2*01 | TRBD1*01 | tgt gcc agc ata gaa atg gca cag ggg ccg aac acc ggg gag ctg ttt ttt | CASIEMIGQGPNTGELFF |
| HD-4 | 58 | TRBV6-6*01 | TRBJ2-1*01 | TRBD2*01 | tgt gcc agc agc agc ggg gcc ccc atc gag cag ttc ttc | CASNSGGPPIEQFF |
| HD-4 | 59 | TRBV6-5*01 | TRBJ2-7*01 | TRBD1*01 | tgt gcc agc agt ggg aca ggt tac gag cag tac ttc | CASRGTGYEQYF |
| HD-4 | 83 | TRBV6-5*01 | TRBJ1-5*01 | TRBD1*01 | tgt gcc agc agg ggg aca ggt tac gag cag tac ttc | CASRGTGYEQYF * |
| HD-4 | 32 | TRBV6-5*01 | TRBJ2-3*01 | TRBD2*01 | tgt gcc agc aga aag gga cag cct cca gat acg cag tat ttt | CASRKGQPPDTQYF |
| HD-4 | 24 | TRBV28*01 | TRBJ2-3*01 | TRBD2*01 | tgt gcc agc agt acc gac ccc tgg ggt gtg agg agc aca gat acg cag tat ttt | CASRNTDPWGVRSTDTQYF |
| HD-4 | 64 | TRBV19*01 | TRBJ2-7*01 | TRBD2*02 | tgt gcc agt aga tct agc ggg agg gcc ctc gag cag tac ttc | CASRSSGRALEQYF |
| HD-4 | 76 | TRBV9*01 | TRBJ2-3*01 | TRBD2*01 | tgt gcc agc agc gac cct aac cgg gca gat acg cag tat ttt | CASSDPNRADTQYF |
| HD-4 | 30 | TRBV27*01 | TRBJ2-1*01 | TRBD2*01 | tgt gcc agt ttc ggg agg ggc cca atc gag cag ttc ttc | CASSFGGRALNEQFF |
| HD-4 | 40 | TRBV5-1*01 | TRBJ2-1*01 | TRBD2*02 | tgt gcc agc agc ttc atg tcg ggc tcc ctg ggg aat gag cag ttc ttc | CASSFMSGSLGNEQFF |
| HD-4 | 51 | TRBV28*01 | TRBJ2-1*01 | TRBD2*02 | tgt gcc agc agc aga ctg gcg gga ggt gag cag ttc ttc | CASSGLAGGEQFF |
| HD-4 | 5 | TRBV19*01 | TRBJ1-5*01 | TRBD2*01 | tgt gcc agt agt att atg gga cag ggt ggc cag ccc cag cat ttt | CASSIMGQGGPQPHF |
| HD-4 | 88 | TRBV19*01 | TRBJ2-3*01 | TRBD2*01 | tgt gcc agt agt atc gtc agt agc cga tac aca gat acg cag tat ttt | CASSIVSSRYTDTQYF |
| HD-4 | 65 | TRBV10-1*01 | TRBJ2-7*01 | TRBD1*01 | tgc gcc agc agt aag gac agc agc agc tcc tac gag cag tac ttc | CASSKDSSSYEQYF |
| HD-4 | 85 | TRBV7-9*01 | TRBJ2-1*01 | TRBD2*01 | tgt gcc agc agc tta gct ttc ggg gac aat gag cag ttc ttc | CASSLAFGDNEQFF |
| HD-4 | 19 | TRBV5-1*01 | TRBJ2-7*01 | TRBD2*01 | tgc gcc agc agc ttg ggc caa gtc ggc gga gag tac ttc | CASSLAGQVGEQYF |
| HD-4 | 22 | TRBV5-8*01 | TRBJ2-7*01 | TRBD2*01 | tgc agc agc tta gct tac cgc cat agg acg gcc tac gag cag tac ttc | CASSLAYRHRTAYYEQYF |
| HD-4 | 14 | TRBV11-3*01 | TRBJ2-3*01 | TRBD1*01 | tgc agc agc ttg gat gga aca ttt ctt cgc aca gat acg cag tat ttt | CASSLDGTFLRTDTQYF |
| HD-4 | 87 | TRBV7-3*01 | TRBJ2-7*01 | TRBD2*01 | tgt gcc agc agc tta gac gtc tcc tac gag cag tac ttc | CASSLDVSYEQYF |
| HD-4 | 71' | TRBV13*01 | TRBJ2-2*01 | TRBD2*01 | tgt gcc agc agc tta gaa gga cta tcg aac acc ggg gag ctg ttt ttt | CASSLEGLSNTGELFF |
| HD-4 | 42 | TRBV11-2*01 | TRBJ2-1*01 | TRBD1*01 | tgc agc agc tta gaa tat ccg ggg aca ggg att gag cag tac ttc | CASSLEYPGTGIEQYF |
| HD-4 | 68 | TRBV11-2*01 | TRBJ2-7*01 | TRBD2*02 | tgc agc agc tta ggt tgg gga gcg gga gcc aaa aac att gag tac ttc | CASSLGAGGIYEQYF |
| HD-4 | 62 | TRBV5-6*01 | TRBJ2-7*01 | TRBD2*01 | tgc agc agc ttg ggg gcg gtg gtc ctc tac gag cag tac ttc | CASSLGAVLYEQYF |
| HD-4 | 7 | TRBV5-6*01 | TRBJ2-7*01 | TRBD1*01 | tgc agc agc tta ggg ggc ttg atc tac gag cag tac ttc | CASSLGLIYEQYF |
| HD-4 | 43 | TRBV5-4*01 | TRBJ1-1*01 | TRBD2*01 | tgt gcc agc agc ttg gga gga cag cgt gaa gct ttc ttt | CASSLGGQREAFF |
| HD-4 | 93 | TRBV11-3*01 | TRBJ2-7*01 | TRBD1*01 | tgt gcc agc agc ttg ggc caa ggc tac gag cag tac ttc | CASSLGQQYEQYF |
| HD-4 | 39 | TRBV7-9*01 | TRBJ1-4*01 | TRBD2*01 | tgc agc agc tta ggt tgg gga gcc aaa aac att cag tac ttc | CASSLGWGAKNIQYF |
| HD-4 | 36 | TRBV11-2*01 | TRBJ1-5*01 | | tgc agc agc tta aat agc tat agc aat cag ccc cag cat ttt | CASSLNSYSNQPQHF |
| HD-4 | 13 | TRBV28*01 | TRBJ1-5*01 | TRBD1*01 | tgt gcc agt tta cgg gga cta gcg ggc tgg tcc gac aat gag cag ttc ttc | CASSLRGSNQPQHF |
| HD-4 | 86 | TRBV28*01 | TRBJ2-1*01 | TRBD2*01 | tgt gcc agc agt tta tcg gga cta gcg ggc tgg tcc gac aat gag cag ttc ttc | CASSLSLGAGWSDNEQFF |
| HD-4 | 15 | TRBV27*01 | TRBJ2-7*01 | TRBD1*01 | tgt gcc agt ccc cct gcg gga gtc tcc tac gag cag tac ttc | CASSLYSSYEQYF |
| HD-4 | 11 | TRBV12-3*01 | TRBJ2-3*01 | TRBD2*02 | tgt gcc agt ccc ggg gag ggt cgc aca gat acg cag tat ttt | CASSPGEGRTDTQYF |
| HD-4 | 78 | TRBV28*01 | TRBJ1-1*01 | TRBD1*01 | tgt gcc agc agt cct gga cct gaa gct ttc ttt | CASSPGPEAFF |
| HD-4 | 77 | TRBV3-1*01 | TRBJ2-2*01 | TRBD1*01 | tgc agc agc ccg ata aag ccc ggg ctg gag ctt ttt | CASSPIDKPGELFF |
| HD-4 | 52 | TRBV9*01 | TRBJ1-1*01 | TRBD2*01 | tgt gcc agc agc cca cta gct agg ggg aac act gaa gct ttc ttt | CASSPLARGNTEAFF |
| HD-4 | 31 | TRBV7-6*01 | TRBJ2-7*01 | TRBD2*01 | tgt gcc agc agt ccg atg agc acg gtt ttc tcc tac gag cag tac ttc | CASSPMSTVFSYEQY |
| HD-4 | 3 | TRBV12-3*01 | TRBJ1-1*01 | TRBD2*01 | tgt gcc agc agt ccc cct gcg ggc act gaa gct ttc ttt | CASSPPAGTEAFF |
| HD-4 | 23 | TRBV6-2*01 | TRBJ2-3*01 | TRBD2*02 | tgt gcc agc agt caa gcg gga gaa agc gat acg cag tat ttt | CASSQAGESDTQYF |
| HD-4 | 53 | TRBV4-3*01 | TRBJ2-7*01 | TRBD2*01 | tgc agc agc cag gat gga aca ggc tcc tac gag cag tac ttc | CASSQDGTGSYEQYF |
| HD-4 | 9 | TRBV4-2*01 | TRBJ1-6*01 | TRBD1*01 | tgt gcc agc agc caa ggc tgg cag gca agg gga tca ccc ctc cac ttt | CASSQGWQARGSPLHF |
| HD-4 | 37 | TRBV3-1*01 | TRBJ1-4*01 | TRBD1*01 | tgc agc agc cag ctc gaa acc acc agg aaa tg ttt ttt | CASSQLETTRKGKLFF |
| HD-4 | 79 | TRBV19*01 | TRBJ1-1*01 | TRBD1*01 | tgt gcc agt agt agg gct cca gag ggg aac act gag gct ttc ttt | CASSRAPEGNTEAFF |

Fig. 2E

| | | | | | | |
|---|---|---|---|---|---|---|
| HD-4 | 1 | TRBV12-3*01 | TRBJ1-2*01 | TRBD1*01 | tgt gcc agc agt cgc aac cgg gac agg gaa aac tat ggc tac acc ttc | CASSRNRDRENYGYTF |
| HD-4 | 56 | TRBV13*01 | TRBJ2-7*01 | TRBD2*01 | tgt gcc agc agc tcc cac gga act caa ggc tcc tac gag tac ttc | CASSHGTQGSYEQYF |
| HD-4 | 63 | TRBV7-9*01 | TRBJ1-5*01 | TRBD1*01 | tgt gcc agc agc tca acg gac agg ggg cct cgg gat cag ccc cag cat ttt | CASSSTDRGPRDQPQHF |
| HD-4 | 84 | TRBV9*01 | TRBJ2-4*01 | TRBD2*02 | tgt gcc agc agc gta gac ggg agt caa tat cac aaa aac att cag tac ttc | CASSVDGSQYHKNIQYF |
| HD-4 | 54 | TRBV9*01 | TRBJ1-1*01 | | tgt gcc agc agc gta gaa gcc aaa act gaa gct ttc ttt | CASSVEAKTEAFF |
| HD-4 | 49 | TRBV9*01 | TRBJ2-1*01 | TRBD2*01 | tgt gcc agc agc gtt ggg gga cgc acg atc gag gac gag tac ttc | CASSVGGRTIEDEQYF |
| HD-4 | 18 | TRBV9*01 | TRBJ2-2*01 | TRBD2*02 | tgt gcc agc agc gta gga ggc agc acc ggg gag ctg ttt | CASSVGGSTGELFF |
| HD-4 | 35 | TRBV2*01 | TRBJ1-2*01 | TRBD1*01 | tgt gcc agc agt gtt cca gac ggg aca ggg ggc gac aat ggc tac acc ttc | CASSVPDGTGDNGYTF |
| HD-4 | 28 | TRBV6-2*01 | TRBJ2-3*01 | TRBD2*01 | tgt gcc agc agt tgg tcg gtc ctt gac aca gat acg cag tat ttt | CASSWSVLSTDTQYF |
| HD-4 | 69 | TRBV11-2*01 | TRBJ1-1*01 | TRBD1*01 | tgt gcc agc agc tac ttt gac agc gtg aac act gaa gct ttc ttt | CASSYFDSVNTEAFF |
| HD-4 | 6 | TRBV19*01 | TRBJ2-2*01 | TRBD2*01 | tgt gcc agt acc tat agt gat acc ggg gag ctg ttt ttt | CASTYSDTGELFF * |
| HD-4 | 10 | TRBV19*01 | TRBJ2-2*01 | TRBD2*01 | tgt gcc agt acc tat agt gat acc ggg gag ctg ttt ttt | CASTYSDTGELFF |
| HD-4 | 44 | TRBV19*01 | TRBJ2-2*01 | TRBD2*01 | tgt gcc agt acc tat agt gat acc ggg gag ctg ttt ttt | CASTYSDTGELFF * |
| HD-4 | 82 | TRBV19*01 | TRBJ2-2*01 | TRBD2*01 | tgt gcc agt acc tat agt gat acc ggg gag ctg ttt ttt | CASTYSDTGELFF * |
| HD-4 | 50 | TRBV24-1*01 | TRBJ2-1*01 | TRBD1*01 | tgt gcc tgg caa aca aga gcc agg ggc acg aac gag tac ttc | CATSDPMTGGTNEQYF |
| HD-4 | 38 | TRBV30*01 | TRBJ1-6*01 | TRBD1*01 | tgt gcc agt cgg aca aga gcc agg ggc agg aat tca ccc ctc cac ttt | CAWQTRARGRNSPLHF |
| HD-4 | 47 | TRBV30*01 | TRBJ1-3*01 | TRBD1*01 | tgt gcc tgg aga ccc ccg gga cag ggg ccc gga aac acc ata tat ttt | CAWRPPGQGPGNTIYF |
| HD-4 | 8 | TRBV20-1*01 | TRBJ2-3*01 | TRBD1*01 | tgc agt gct aga tcc gga gca cag ggg gat acg cag tat ttt | CSADSLTGQGAGDTQYF |
| HD-4 | 12 | TRBV20-1*01 | TRBJ1-1*01 | TRBD1*01 | tgc agt gcg gga cca ggg gat ttg aac act gaa gct ttc ttt | CSAGPGDLNTEAFF |
| HD-4 | 57 | TRBV20-1*01 | TRBJ2-1*01 | TRBD2*01 | tgc agt gcg ggt acg tcg gac ctt aat gag cag tac ttc | CSAGTSDLNEQFF |
| HD-4 | 34 | TRBV20-1*01 | TRBJ2-2*01 | TRBD2*02 | tgc agt gct aga gat ggg ggg ggc acc ggg gag ctg ttt ttt | CSARDGGRDTGELFF |
| HD-4 | 46 | TRBV20-1*01 | TRBJ2-2*01 | TRBD1*01 | tgc agt gct aga gat gtg ggg gca ggg gag ctg ttt ttt | CSARDVGAGTGELFF |
| HD-4 | 61 | TRBV20-1*01 | TRBJ1-6*02 | TRBD1*01 | tgc agt gct aga gaa gga cac gaa agt tca ccc ctc cac ttt | CSAREGHESSPLHF |
| HD-4 | 25 | TRBV20-1*01 | TRBJ2-1*01 | TRBD1*01 | tgc agt gct agg gag gga cta ggg cac ctc gag cag tac ttc | CSAREGLGHLEQYF |
| HD-4 | 70 | TRBV20-1*01 | TRBJ2-7*01 | TRBD2*02 | tgc agt gct aga gag gtt ccg agc tcc tac gag cag tac ttc | CSAREGPSSYEQYF |
| HD-4 | 66 | TRBV20-1*01 | TRBJ2-1*01 | TRBD1*01 | tgc agt gct aga ggg ttc cgg gcg ggg gag cag tac ttc | CSARGFRAGEQFF |
| HD-4 | 41 | TRBV20-1*01 | TRBJ2-7*01 | TRBD2*01 | tgc agt gct aga gga ttt agc ggg cca aat tac gag cag tac ttc | CSARGFSGPNYEQYF |
| HD-4 | 81 | TRBV20-1*01 | TRBJ2-7*01 | TRBD2*01 | tgc agt gct aga tcc cct tcg aca gac tac gag cag tac ttc | CSARSPSTDYEQYF |
| HD-4 | 45 | TRBV20-1*01 | TRBJ2-5*01 | TRBD2*02 | tgc agt gct gct agt aat atc gcg gga gga cgc ggg acc cag ttc | CSASNIAGGRETQYF * |
| HD-4 | 48 | TRBV20-1*01 | TRBJ2-5*01 | TRBD2*02 | tgc agt gct agt aat atc gcg gga gga cgc gga acc cag tac ttc | CSASNIAGGRETQYF * |
| HD-4 | 21 | TRBV20-1*01 | TRBJ2-7*01 | | tgc agt gct acg tca acc gtc tac gag cag tac ttc | CSATSTVYEQYF |
| HD-4 | 92 | TRBV20-1*01 | TRBJ1-1*01 | TRBD1*01 | tgc agt gct caa gag gac gtc tct gga aac acc ata tat ttt | CSAYQEDVSGNTIYF |
| HD-4 | 26 | TRBV29-1*01 | TRBJ2-1*01 | TRBD2*01 | tgt gtt gaa gac gaa cta ggg ggg cat gag gag cac ttc | CSVEDELAGGHEQFF |
| HD-4 | 33 | TRBV29-1*01 | TRBJ2-1*01 | TRBD2*01 | tgc agc gtt gaa gtc cca ttg gtg ttg gac tac aat gag cag ttc | CSVEVPLVLDYNEQFF |
| HD-4 | 74 | TRBV29-1*01 | TRBJ2-1*01 | TRBD2*01 | tgc agc gtt gag gtc aga ctc aat gag cag ttc ttc | CSVEVRLNEQFF |
| HD-5 | 23 | TRBV27*01 | TRBJ2-5*01 | TRBD1*01 | tgc atc ctc aat tct ccg gga cag tat cgg acc cag tac ttc | CAILNSPGQYRTQYF |
| HD-5 | 107 | TRBV10-3*01 | TRBJ2-7*01 | TRBD2*01 | tgt atc agt gag ccc gac agg ggt gtc tac gag cag tac ttc | CAISEPDRGVYEQYF |
| HD-5 | 63 | TRBV10-3*01 | TRBJ1-2*01 | TRBD1*01 | tgt atc agt gag aga gga gga aca ggg gcc tac gag cag tac ttc | CAISERGGTGAYEQYF |
| HD-5 | 13 | TRBV27*01 | TRBJ2-4*01 | | tgt gcc agc gcc ttt ggg gaa gca gca gga acc ttc | CASAFFGEAGYGTF |
| HD-5 | 114 | TRBV2*01 | TRBJ2-1*01 | | tgt gcc agc atg ggg tct gag cag ttc | CASMDGSEQFF |
| HD-5 | 102 | TRBV28*01 | TRBJ2-7*01 | TRBD2*02 | tgt gcc agc aac gga gag cgg gga tac gag cag tac ttc | CASNGEREGYEQYF |
| HD-5 | 9 | TRBV9*01 | TRBJ1-1*01 | TRBD1*01 | tgt gcc agc aga att ggg act tac act gaa gct ttc ttt | CASRIGTYTEAFF |
| HD-5 | 116 | TRBV7-9*01 | TRBJ2-3*01 | TRBD1*01 | tgt gcc agc agg cct atg ggg aca gat acg cag tat ttt | CASRPMGTDTQYF |
| HD-5 | 8 | TRBV3-1*01 | TRBJ2-1*01 | TRBD2*01 | tgt gcc agc agg tcc tta gcg ggg ggt gag cag ttc | CASRSLAGEQFF |
| HD-5 | 41 | TRBV28*01 | TRBJ2-3*01 | TRBD2*01 | tgt gcc agc aga act agc ggc aca gat acg cag tat ttt | CASRTSGTDTQYF |
| HD-5 | 93 | TRBV9*01 | TRBJ2-7*01 | TRBD1*01 | tgt gcc agc agt gaa gag ggg gcg ggc tac gag cag tac ttc | CASSEEGAGYEQYF |
| HD-5 | 72 | TRBV2*01 | TRBJ2-7*01 | TRBD2*01 | tgt gcc agc agt gag gga cat cca agt caa tac gag cag tac ttc | CASSEEGHPSQYEQYF |
| HD-5 | 48 | TRBV5-1*01 | TRBJ2-7*01 | TRBD2*02 | tgc gcc agc agc gag aat aag att gga gtt gcc gta tcc tac gag tac ttc | CASSENKIGVAVSYEQYF |
| HD-5 | 19 | TRBV11-2*01 | TRBJ2-7*01 | TRBD2*01 | tgc gcc agc agc ttt ggg gaa tac gag cag tac ttc | CASSEYYEQYF |
| HD-5 | 40 | TRBV28*01 | TRBJ1-5*01 | TRBD1*01 | tgt gcc agc agt ttt gac cgg gac agg ggc cct cag ccc cag cat ttt | CASSFDRDRGPQPQHF |
| HD-5 | 54 | TRBV12-3*01 | TRBJ2-5*01 | TRBD2*01 | tgt gcc agc agt ttc ggg gga gag gag gga gag acc cag tac ttc | CASSFGGEGETQYF |
| HD-5 | 111 | TRBV27*01 | TRBJ1-4*01 | | tgt gcc agc agt ttc tcc gga act aat gaa aaa ctg ttt ttt | CASSFSGTNEKLFF |
| HD-5 | 20 | TRBV28*01 | TRBJ1-3*01 | | tgt gcc agc agt ttt agt act agt gga aac acc ata tat ttt | CASSFSTSGNTIYF |
| HD-5 | 21 | TRBV27*01 | TRBJ2-3*01 | TRBD2*01 | tgt gcc agc agt ttc acg act ttc gga acc gat acg cag tat ttt | CASSFTTSGATDTQYF |
| HD-5 | 44 | TRBV9*01 | TRBJ2-5*01 | | tgt gcc agc agc ggc cat ttc caa gag acc cag tac ttc | CASSGHFQETQYF |
| HD-5 | 17 | TRBV9*01 | TRBJ2-1*01 | TRBD2*02 | tgt gcc agc agc gga cta gcg ggg tct ggg tac aat gag cag ttc ttc | CASSGLAGGSGYNEQFF |
| HD-5 | 35 | TRBV19*01 | TRBJ1-4*01 | TRBD1*01 | tgt gcc agt ata gaa cta cta aac aga gaa aaa ctg ttt ttt | CASSIELLNREKLFF |
| HD-5 | 52 | TRBV28*01 | TRBJ1-1*01 | | tgt gcc agc agt atc ctc act gaa gct ttc ttt | CASSILTEAFF |

Fig. 2F

| | | | | | | | |
|---|---|---|---|---|---|---|---|
| HD-5 | 74 | TRBV19*01 | | TRBJ2-2*01 | | tgt gcc agt agt ata ccc tgg acc ggg gag ctg ttt ttt | CASSIPWTGELFF |
| HD-5 | 3 | TRBV19*01 | | TRBJ2-7*01 | | tgt gcc agt agt atc act ttc tcc tac gag cag tac ttc | CASSITFSYEQYF |
| HD-5 | 51 | TRBV19*01 | | TRBJ1-5*01 | TRBD1*01 | tgt gcc agt agt aag ggt tat ggc aat cag ccc cag cat ttt | CASSKGYGNQPQHF |
| HD-5 | 4 | TRBV27*01 | | TRBJ2-1*01 | TRBD2*02 | tgt gcc agc agt cta gcg gga gac ggg tac aat gag acg cag ttc | CASSLAGDGYNEQFF |
| HD-5 | 32 | TRBV11-2*01 | | TRBJ2-3*01 | TRBD2*02 | tgt gcc agc agc ctt gat agc ggg agg gcc caa gat acg cag tat ttt | CASSLDSGRAQDTQYF |
| HD-5 | 66 | TRBV11-3*01 | | TRBJ2-7*01 | TRBD1*01 | tgt gcc agc agc tta gac agc tcc tac gag cag tac ttc | CASSLDSSYEQYF |
| HD-5 | 79 | TRBV7-3*01 | | TRBJ2-7*01 | TRBD2*02 | tgt gcc agc agc ctg ggt agg gcc agc tcc tac gag cag tac ttc | CASSLGGRASSYEQYF |
| HD-5 | 101 | TRBV5-4*01 | | TRBJ1-1*01 | TRBD2*01 | tgt gcc agc agc ttg ggt tcg gga ggt ccc ttc gat gag cag ttc ttc | CASSLGSGPFDEQFF |
| HD-5 | 85 | TRBV7-9*01 | | TRBJ2-5*01 | TRBD2*01 | tgt gcc agc agc ctg ggt tac ggc gaa gag acc cag tac ttc | CASSLGYGEETQYF |
| HD-5 | 110 | TRBV7-9*01 | | TRBJ2-5*01 | TRBD2*01 | tgt gcc agc agc ctg ggg tac ggg gag gag acc cag tac ttc | CASSLGYGEGETQYF |
| HD-5 | 6 | TRBV7-9*01 | | TRBJ2-3*01 | TRBD2*01 | tgt gcc agc agc tta ggg tac tgg agc aca gat acg cag tat ttt | CASSLGYGSTDTQYF |
| HD-5 | 15 | TRBV7-3*01 | | TRBJ2-3*01 | TRBD2*02 | tgt gcc agc agc tta atc ccc gag ggc gtc ggc aca gat acg cag tat ttt | CASSLIPEGVGTDTQYF |
| HD-5 | 62 | TRBV9*01 | | TRBJ1-1*01 | TRBD1*01 | tgt gcc agc agc ctc cgg ggg aac act gaa gct ttc ttt | CASSLRGNTEAFF |
| HD-5 | 49 | TRBV5-4*01 | | TRBJ2-7*01 | TRBD2*02 | tgt gcc agc agc tta act agc ggg agt ctc aac gag cag tac ttc | CASSLTSGSLNEQYF |
| HD-5 | 47 | TRBV11-2*01 | | TRBJ2-1*01 | TRBD1*01 | tgt gcc agc agc ttg gtc ccg aca gat ggg gac tat ggc tac acc ttc | CASSLVPTGEDYGYTF |
| HD-5 | 99—1 | TRBV19*01 | | TRBJ2-3*01 | TRBD2*02 | tgt gcc agt agt atg gga ggg cca gat acg cag tat ttt | CASSMGGPDTQYF |
| HD-5 | 106 | TRBV12-3*01 | | TRBJ1-1*01 | TRBD2*02 | tgt gcc agc agc ggg caa gtt tgg aac act gaa gct ttc ttt | CASSNGQVWNTEAFF |
| HD-5 | 73 | TRBV18*01 | | TRBJ2-7*01 | TRBD1*01 | tgt gcc agc tca cct gca ggg cga acc tac tcc tac gag cag tac ttc ttc | CASSPAGRTYSYEQYF |
| HD-5 | 109 | TRBV27*01 | | TRBJ2-7*01 | TRBD2*01 | tgt gcc agc agt cgg ggt cgc acc tac gag cag tac ttc | CASSPGRTYEQYF |
| HD-5 | 86 | TRBV7-2*02 | | TRBJ1-1*01 | TRBD1*01 | tgt gcc agc agc ccg ggg agc act gaa gct ttc ttt | CASSPGSTEAFF |
| HD-5 | 50 | TRBV7-8*01 | | TRBJ2-5*01 | TRBD2*02 | tgt gcc agc agc cat agc ccc gga cta gcg gga gtt tca caa gag acc cag tac ttc | CASSPHSPGLAGVSQETQYF |
| HD-5 | 68 | TRBV18*01 | | TRBJ2-1*01 | TRBD1*01 | tgt gcc agc tca cca caa tgg agg aca ggg gag tat gag cag ttc ttc | CASSPQWGTGEYEQFF |
| HD-5 | 65 | TRBV9*01 | | TRBJ1-1*01 | TRBD1*01 | tgt gcc agc agc ccc cgg aca gcc atg aac act gaa gct ttc ttt | CASSPRTAMNTEAFF |
| HD-5 | 14 | TRBV4-1*01 | | TRBJ2-7*01 | TRBD2*02 | tgc agc agc caa gat tgg cca ggg agc tcc tac gag cag tac ttc | CASSQDWPGSSYEQYF |
| HD-5 | 1 | TRBV4-1*01 | | TRBJ1-5*01 | TRBD1*01 | tgt gcc agc caa gag ggt ttt aat cag ccc cag cat ttt | CASSQEGFNQPQHF |
| HD-5 | 7 | TRBV3-1*01 | | TRBJ2-7*01 | TRBD2*01 | tgt gcc agc cag gag ctt tcc ccc cct tac gag cag tac ttc | CASSQELSPPYEQYF |
| HD-5 | 104 | TRBV9*01 | | TRBJ2-5*01 | TRBD2*02 | tgt gcc agc cag ggg gcc gag tac caa gag acc cag tac ttc | CASSQGAEYQETQYF |
| HD-5 | 84 | TRBV4-1*01 | | TRBJ1-4*01 | TRBD1*01 | tgc agc agc caa gga gaa ggg aga gag cag tac ttc | CASSQGREQYF |
| HD-5 | 59—2 | TRBV3-1*01 | | TRBJ2-1*01 | TRBD1*01 | tgt gcc agc caa tta ggg gat ttt ggc tac acc ttc | CASSQLGDFGYTF |
| HD-5 | 75 | TRBV13-01 | | TRBJ1-1*01 | TRBD1*01 | tgt gcc agc caa cta cag cag ggc ctc act gaa gct ttc ttt | CASSQLQQGLTEAFF |
| HD-5 | 120 | TRBV2-3*01 | | TRBJ2-7*01 | TRBD1*01 | tgt gcc agc caa cgt aga aca gat acg cag tat ttt | CASSQRRTDTQYF |
| HD-5 | 60 | TRBV12-3*01 | | TRBJ2-6*01 | TRBD1*01 | tgc agt agt cgg cag ggg gca gcg ccg gcc aac gtc ctg act ttc | CASSRQGAAPANVLTF |
| HD-5 | 90 | TRBV28*01 | | TRBJ2-7*01 | TRBD2*01 | tgt gcc agc agc cga ggg gcc tcc tac gag cag tac ttc | CASSRGASYEQYF |
| HD-5 | 113 | TRBV7-6*01 | | TRBJ2-1*01 | TRBD2*01 | tgt gcc agc agc agc gga tcc ggc gat gag cag ttc ttc | CASSSGDEQFF |
| HD-5 | 57 | TRBV11-4*01 | | TRBJ1-1*01 | TRBD1*01 | tgt gcc agc agc tcc aaa ggg cag gca tca aat gaa aaa ctg ttt ttt | CASSSKGPQASNEKLFF |
| HD-5 | 98 | TRBV5-5*01 | | TRBJ2-7*01 | TRBD1*01 | tgt gcc agc agc tta cag ggg gac gac gag cag tac ttc | CASSSLQGDDEQYF |
| HD-5 | 64 | TRBV5-6*01 | | TRBJ2-7*01 | TRBD2*02 | tgt gcc agc agc tcg cct ttc tca gga cta gcg gga acc tac tcc tac gag cag tac ttc | CASSSPFSGLAGTYSYEQYF |
| HD-5 | 112 | TRBV19*01 | | TRBJ2-2*01 | TRBD1*01 | tgt gcc agt agt tcc tcg gac agg gcg gta atc tgg acc ggg gag ctg ttt ttt | CASSSSDRAVWTGELFF |
| HD-5 | 67 | TRBV28*01 | | TRBJ2-7*01 | TRBD1*01 | tgt gcc agc agt tcc agc agc ggg acc gag cag tac ttc | CASSSSGTEQYF |
| HD-5 | 43 | TRBV28*01 | | TRBJ2-4*01 | TRBD2*01 | tgt gcc agc agc acc cgc ggg agt ggg ggt tcg gaa gct ttc | CASSVDPARDIGYF |
| HD-5 | 58 | TRBV28*01 | | TRBJ2-1*01 | TRBD2*02 | tgt gcc agt agt gta gac cca gct agg gac att cag tac ttc | CASSVGTSGRNEQFF |
| HD-5 | 10' | TRBV6-5*01 | | TRBJ2-5*01 | TRBD1*01 | tgt gcc acc agt gat tac cgg gag agc tcg tct ggg tgg cag ccg atg gac ttc | CASSYSSGWGPMDF |
| HD-5 | 70 | TRBV19*01 | | TRBJ2-1*01 | TRBD1*01 | tgt gcc acc agt atc ggg ggg acg ggg caa tat agc aat cag ccc cag cat ttt | CASTAIGGTGQYSNQPQHF |
| HD-5 | 18 | TRBV3-1*01 | | TRBJ1-1*01 | TRBD1*01 | tgt gcc acc agg ggg ggg agt ggg ggt tcg gaa gct ttc | CASTRGGGGSEAFF |
| HD-5 | 42 | TRBV12-3*01 | | TRBJ2-1*01 | TRBD2*02 | tgt gcc agc agt cta ggg act agc ggg agg aat gag cag ttc ttc | CASTSRTVSSYNEQFF |
| HD-5 | 25 | TRBV24-1*01 | | TRBJ2-1*01 | TRBD1*01 | tgc agc acc agt gat tac cgg gac agc agc aat gag cag ttc ttc | CATSDYRDSTYNEQFF |
| HD-5 | 33 | TRBV15*01 | | TRBJ1-5*01 | TRBD1*01 | tgt gcc acc agt ttt agt agg gac aga acc aat cag ccc cag cat ttt | CATSFSRDRGNQPQHF |
| HD-5 | 38 | TRBV15*01 | | TRBJ2-1*01 | TRBD1*01 | tgt gcc acc agc aga gac agg ggt ggg acc ggg gag ctg ttt ttt | CATSRDRGGTGELFF |
| HD-5 | 34 | TRBV12-3*01 | | TRBJ1-3*01 | TRBD2*01 | tgt gcc gta gcg cac aca gat acg cag tat ttt | CAVAHTDTQYF |
| HD-5 | 69 | TRBV1-1*01 | | TRBJ1-1*01 | | tgt gcc tgg agt gtc ggg aac act gaa gct ttc ttt | CAWSVGNTEAFF |
| HD-5 | 71 | TRBV2*01 | | TRBJ2-7*01 | TRBD2*01 | tgt gac ctg aat gaa acg ttc cgc cgg ccc tac gag cag tac ttc | CDLNETFRRPYEQYF |
| HD-5 | 56—2 | TRBV20-1*01 | | TRBJ2-1*01 | TRBD1*01 | tgt agt gcc gac cac agg ggg gat gag cag ttc ttc | CSADHRGDEQFF |
| HD-5 | 29 | TRBV29-1*01 | | TRBJ2-5*01 | | tgt agt gcc gcc gaa gag acc cag tac ttc | CSAHEETQYF |
| HD-5 | 2 | TRBV20-1*01 | | TRBJ2-7*01 | TRBD1*01 | tgc agt gcc aac cgg cga gtc gag cag tac ttc | CSANRERVEQYF |
| HD-5 | 39 | TRBV20-1*01 | | TRBJ2-7*01 | TRBD1*01 | tgc agt gct ccc tcg gga cag ggc tac gag cag tac ttc | CSAPSGQGYEQYF |
| HD-5 | 97 | TRBV20-1*01 | | TRBJ2-1*01 | TRBD2*02 | tgc agt agt aga gat agc ggg agc tcc tgg gat gag cag ttc ttc | CSARDSGSSWDEQFF |
| HD-5 | 5 | TRBV20-1*01 | | TRBJ2-5*01 | TRBD2*02 | tgc agt gct gga act acg tgg gag gcc gga caa gag acc cag tac ttc | CSGDTWEAGQETQYF |
| HD-5 | 11 | TRBV29-1*01 | | TRBJ1-2*01 | TRBD1*01 | tgc agc tct ata ggg gag ctc ctg gat ggc tac acc ttc | CSSIGELLDGYTF * |

Fig. 2G

| | | | | | | |
|---|---|---|---|---|---|---|
| HD-5 | 12 | TRBV29-1*01 | TRBJ1-2*01 | TRBD1*01 | tgc agc tct ata ggg gag ctc ctg gat ggc tac acc ttc | CSSIGELLDGYTF* |
| HD-5 | 31 | TRBV29-1*01 | TRBJ1-2*01 | TRBD1*01 | tgc agc tct ata ggg gag ctc ctg gat ggc tac acc ttc | CSSIGELLDGYTF* |
| HD-5 | 105 | TRBV29-1*01 | TRBJ1-2*01 | TRBD1*01 | tgc agc tct ata ggg gag ctc ctg gat ggc tac acc ttc | CSSIGELLDGYTF* |
| HD-5 | 115 | TRBV29-1*01 | TRBJ2-3*01 | TRBD2*01 | tgc agc gtt ggg gcg ccg ggg tca gat acg cag tat ttt | CSVGAPGSDTQYF |
| PT-1 | 3 | TRBV28*01 | TRBJ2-7*01 | TRBD2*01 | tgt gcc agc aga aat agc gcc gac tcc tac gag cag tac ttc | CASRNSADSYEQYF* |
| PT-1 | 61 | TRBV28*01 | TRBJ2-7*01 | TRBD2*01 | tgt gcc aga aat agc gcc gac tcc tac gag cag tac ttc | CASRNSADSYEQYF* |
| PT-1 | 15 | TRBV28*01 | TRBJ1-1*01 | | tgt gcc aga cgc atg acg gct ttc ttt | CASRRRMTEAFF |
| PT-1 | 44 | TRBV25-1*01 | TRBJ1-1*01 | TRBD1*01 | tgt gcc agc agt gag gag aca ggg ggc acg agc act gaa gct ttc ttt | CASSEETGGTSTEAFF |
| PT-1 | 38 | TRBV5-1*01 | TRBJ2-7*01 | TRBD1*01 | tgc gcc agc agc gag aga cag ggg aat ato tac tcc gag cag tac ttc | CASSERQGNIYSEQYF |
| PT-1 | 18 | TRBV9*01 | TRBJ2-1*01 | TRBD2*01 | tgc gcc agt gag agc ggg ggg gcc gac tac aat gag cag ttc ttc | CASSESGADYNEQFF |
| PT-1 | 6 | TRBV28*01 | TRBJ1-3*01 | TRBD1*01 | tgt gcc agc agt ttc ggg ttc tct gga aac acc ata tat ttt | CASSFGFSGNTIYF* |
| PT-1 | 8 | TRBV28*01 | TRBJ1-3*01 | TRBD1*01 | tgt gcc agc agt ttc ggg ttc tct gga aac acc ata tat ttt | CASSFGFSGNTIYF* |
| PT-1 | 23 | TRBV28*01 | TRBJ1-3*01 | TRBD1*01 | tgt gcc agc agt ttc ggg ttc tct gga aac acc ata tat ttt | CASSFGFSGNTIYF* |
| PT-1 | 49 | TRBV28*01 | TRBJ1-1*01 | TRBD1*01 | tgt gcc agc agt ttc ctg ggt tac act gaa gct ttc ttt | CASSFLGYTEAFF |
| PT-1 | 9 | TRBV28*01 | TRBJ2-3*01 | TRBD2*01 | tgt gcc agc agt ttc ctt agc ggg aca gat acg cag tat ttt | CASSFLSGTDTQYF |
| PT-1 | 30 | TRBV7-9*01 | TRBJ2-2*01 | TRBD1*01 | tgt gcc agc agc ttc agg cag ggg gca agc acc ggg gag ctg ttt | CASSFRQGASTGELFF |
| PT-1 | 31 | TRBV19*01 | TRBJ2-5*01 | TRBD1*01 | tgc gcc agt agt ata caa ttg gtt cca gtg gag acc cag tac ttc | CASSIQLVPVETQYF |
| PT-1 | 37 | TRBV13*01 | TRBJ2-3*01 | TRBD2*01 | tgt gcc agc agc ttg gac gtg ggt gag cag ttc ttc | CASSLDVGEQFF |
| PT-1 | 35 | TRBV7-2*02 | TRBJ1-6*02 | TRBD1*01 | tgt gcc agc agc tta gaa agt ggg cct gtt gtg ggt tca ccc ctc cac ttt | CASSLEGGPVVGSPLHF |
| PT-1 | 10 | TRBV5-5*01 | TRBJ2-3*01 | TRBD2*01 | tgt gcc agc agc ttg gaa cta gcg ggg gat acg cag tat ttt | CASSLELAGRDTQYF |
| PT-1 | 12 | TRBV28*01 | TRBJ2-1*01 | TRBD2*01 | tgt gcc agc agt tta gag tgg act ggg ggg gtt tat gag cag ttc ttc | CASSLEWTGGVYEQFF |
| PT-1 | 14 | TRBV13*01 | TRBJ1-5*01 | TRBD1*01 | tgt gcc agc agc tta gcc agg gga cta aat ccc cag cat ttt | CASSLGRGLNQPQHF |
| PT-1 | 32 | TRBV27*01 | TRBJ2-1*01 | TRBD2*02 | tgt gcc agc agt tta tct ttt ggg tct agc ggg agt acg gag cag ttc | CASSLSFGSSGIRREQF |
| PT-1 | 28 | TRBV27*01 | TRBJ2-3*01 | TRBD2*02 | tgt gcc agc agt tta tgg gct agc ggg agt acg gat acg cag tat ttt | CASSLWASGSTDTQYF |
| PT-1 | 20 | TRBV14*01 | TRBJ1-1*01 | TRBD1*01 | tgc gcc agc ccg gac agg ggc aat gag gag ttc ttc | CASSPDRGNEQFF |
| PT-1 | 29 | TRBV7-3*01 | TRBJ2-1*01 | TRBD2*02 | tgt gcc agc agc ccc agc agt ccc gcc aat gag cag ttc ttc | CASSPSGSPANEQFF |
| PT-1 | 13 | TRBV9*01 | TRBJ2-1*01 | TRBD1*01 | tgt gcc agc agc cca act ttt agc ggg agg aat gag cag ttc ttc | CASSPTFSGRNEQFF |
| PT-1 | 17 | TRBV4-1*01 | TRBJ2-1*01 | TRBD2*01 | tgc gcc agc agc caa gtt ttg agt agg tac ggt gag cag ttc ttc | CASSQVLSRGYGEQFF |
| PT-1 | 46 | TRBV27*01 | TRBJ2-3*01 | TRBD2*01 | tgt gcc agc agt cgg ttt tgg ggg ggt gct agc aca gat acg cag tat ttt | CASSRFWGGASTDTQYF |
| PT-1 | 2 | TRBV7-9*01 | TRBJ2-5*01 | TRBD1*01 | tgt gcc agc agc tca gga cag ggg gca cgt gag acc cag tac ttc | CASSSGQGARETQYF |
| PT-1 | 36 | TRBV11-2*01 | TRBJ2-1*01 | TRBD2*02 | tgc gcc agc agc tcg aat gtg gga gag gag aat gag cag ttc ttc | CASSSNVGEGNEQFF |
| PT-1 | 21 | TRBV11-2*01 | TRBJ2-7*01 | TRBD2*01 | tgt gcc agc agc tcc cct agc ggg ggc acc tac gag cag ttc ttc | CASSSPSGGTYEQYF |
| PT-1 | 26 | TRBV2*01 | TRBJ1-4*01 | TRBD1*01 | tgt gcc agc agc agt acg gga ctt cga gaa aaa ctg ttt ttt | CASSTGLREKLFF* |
| PT-1 | 42 | TRBV2*01 | TRBJ1-4*01 | TRBD1*01 | tgt gcc agc agc agt acg gga ctt cga gaa aaa ctg ttt ttt | CASSTGLREKLFF* |
| PT-1 | 1 | TRBV11-2*01 | TRBJ2-3*01 | TRBD2*01 | tgt gcc agc agc agt tgg ggg gat tct agc aca gat acg cag tat ttt | CASSWGDSSTDTQYF* * |
| PT-1 | 4 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 7 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 11 | TRBV11-2*01 | TRBJ2-3*01 | TRBD2*01 | tgt gcc agc agt tgg ggg gat tct agc acc aca gat acg cag tat ttt | CASSWGDSSTDTQYF* * |
| PT-1 | 16 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 19 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 24 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 25 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 27 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 39 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 40 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 41 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 43 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 48 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 50 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 51 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 52 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 53 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 54 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 55 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 58 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 59 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 60 | TRBV11-2*01 | TRBJ2-3*01 | TRBD2*01 | tgt gcc agc agt tgg ggg gat tct agc aca gat acg cag tat ttt | CASSWGDSSTDTQYF* * |
| PT-1 | 34 | TRBV5-1*01 | TRBJ1-1*01 | TRBD1*01 | tgc gcc agc agt tat aca gac tcg aac act gaa gct ttc ttt | CASSYTDSNTEAFF |

Fig. 2H

| | | | | | | |
|---|---|---|---|---|---|---|
| PT-1 | 47 | TRBV6-5*01 | TRBJ1-4*01 | TRBD1*01 | tgt gcc agc agt tac acg cag ggg cgg acg aat gaa aaa ctg ttt ttt | CASSYTQGRTNEKLFF |
| PT-1 | 22 | TRBV30*01 | TRBJ2-5*01 | TRBD1*01 | tgt gcc tgg agt aca ggc aat gaa gag acc cag tac ttc | CAWSTGNEETQYF |
| PT-1 | 5 | TRBV30*01 | TRBJ1-4*01 | TRBD1*01 | tgt gcc tgg acc ccg ggg agg ggg cgt gaa aaa ctg ttt ttt | CAWTPGRGREKLFF |
| PT-1 | 33 | TRBV20-1*01 | TRBJ1-2*01 | TRBD2*01 | tgc agt gga agg aag gca gat tcc tac gag cag tac ttc | CSGRKADSYEQYF |
| PT-1 | 56 | TRBV29-1*01 | TRBJ1-2*01 | TRBD1*01 | tgc agt gtg aat aca ggg aca gga cat ccc tcg gga cat gcc acc ttc | CSVNTGTGMPSGHGYTF |
| PT-2 | 49 | TRBV10-3*01 | TRBJ2-7*01 | TRBD2*02 | tgt gcc atc agt gag acc cct agc ggg aat ccc acc tac gag cag tac ttc | CAISETPSGNPTYEQYF |
| PT-2 | 73 | TRBV28*01 | TRBJ2-3*01 | TRBD2*02 | tgt gcc agc aaa agc ggg gat acg cag tat ttt | CASKSSGGDTQYF |
| PT-2 | 3 | TRBV12-3*01 | TRBJ2-5*01 | TRBD2*02 | tgt gcc agc ccc aca gta ggg tta cta gag acc cag tac ttc | CASPTVGLLETQYF * |
| PT-2 | 40 | TRBV12-3*01 | TRBJ2-5*01 | TRBD2*02 | tgt gcc agc ccc aca gta ggg tta cta gag acc cag tac ttc | CASPTVGLLETQYF * |
| PT-2 | 56 | TRBV12-3*01 | TRBJ2-5*01 | TRBD2*02 | tgt gcc agc ccc aca gta ggg tta cta gag acc cag tac ttc | CASPTVGLLETQYF * |
| PT-2 | 60 | TRBV12-3*01 | TRBJ2-5*01 | TRBD2*02 | tgt gcc agc ccc aca gta agg tta cta gag acc cag tac ttc | CASPTVGLLETQYF * |
| PT-2 | 62 | TRBV12-3*01 | TRBJ2-5*01 | TRBD1*01 | tgt gcc agc ccc aca gta agg tta cta gag acc cag tac ttc | CASPTVRLLETQYF |
| PT-2 | 41 | TRBV2*01 | TRBJ1-2*01 | TRBD1*01 | tgt gcc aga ggt caa cag aat ttc tat ggc tac acc ttc | CASRGQQNFYGYTF |
| PT-2 | 10 | TRBV6-1*01 | TRBJ2-5*01 | TRBD2*01 | tgt gcc agc agg agc tgg gga tat ccg gag acc cag tac ttc | CASRSWGYPETQYF * |
| PT-2 | 20 | TRBV6-1*01 | TRBJ2-5*01 | TRBD2*01 | tgt gcc agc agg agc tgg gga tat ccg gag acc cag tac ttc | CASRSWGYPETQYF * |
| PT-2 | 8 | TRBV9*01 | TRBJ2-7*01 | TRBD1*01 | tgt gcc agc agc gcc gao agt ggg gtt ttc ggg gag ctg ttt ttt | CASSADSGVTYEQYF |
| PT-2 | 38 | TRBV2*01 | TRBJ2-2*01 | TRBD1*01 | tgt gcc agc agt gcg gga cag gtt ttc ccc ggg gag ctg ttt ttt | CASSAGQVFPGELFF |
| PT-2 | 12 | TRBV2*01 | TRBJ2-5*01 | TRBD2*01 | tgt gcc agc agt gat gga ggg gcg caa gag acc cag tac ttc | CASSDGGAQETQYF * |
| PT-2 | 18 | TRBV2*01 | TRBJ2-5*01 | TRBD2*01 | tgt gcc agc agt gat gga ggg gcg caa gag acc cag tac ttc | CASSDGGAQETQYF * |
| PT-2 | 44 | TRBV2*01 | TRBJ2-5*01 | TRBD2*01 | tgt gcc agc agt gat gga ggg gcg caa gag acc cag tac ttc | CASSDGGAQETQYF * |
| PT-2 | 74 | TRBV2*01 | TRBJ2-5*01 | TRBD2*01 | tgt gcc agc agt gat ggg gga gcg caa gag acc cag tac ttc | CASSDGGGQETQYF * |
| PT-2 | 64 | TRBV2*01 | TRBJ2-5*01 | TRBD2*01 | tgt gcc agc agt gat ggg gga gcg agt gag acc cag tac ttc | CASSDGGASETQYF * * |
| PT-2 | 75 | TRBV2*01 | TRBJ2-5*01 | TRBD2*01 | tgt gcc agc agt gat ggg gga gcg agt gag acc cag tac ttc | CASSDGGASETQYF * * |
| PT-2 | 46 | TRBV5-6*01 | TRBJ1-5*01 | TRBD1*01 | tgt gcc agc agc gag gcc ggg aca ggg cga ggg acc cag tac ttc | CASSEAGTGRETQYF |
| PT-2 | 21 | TRBV2*01 | TRBJ2-5*01 | TRBD2*01 | tgt gcc agc agt gaa gga ggc caa gag acc cag tac ttc | CASSEGGAQETQYF |
| PT-2 | 6 | TRBV2*01 | TRBJ2-5*01 | TRBD2*01 | tgt gcc agc agt gaa gga ggc caa gag acc cag tac ttc | CASSEGGGQETQYF * |
| PT-2 | 13 | TRBV2*01 | TRBJ2-5*01 | TRBD2*01 | tgt gcc agc agt gaa gga ggg ggg cag gag acc cag tac ttc | CASSEGGGQETQYF * |
| PT-2 | 16 | TRBV2*01 | TRBJ2-5*01 | TRBD2*01 | tgt gcc agc agt gaa ggg ggt ggg caa gag acc cag tac ttc | CASSEGGGQETQYF * |
| PT-2 | 23 | TRBV2*01 | TRBJ2-5*01 | TRBD2*01 | tgt gcc agc agt gaa ggg ggt ggg caa gag acc cag tac ttc | CASSEGGGQETQYF * |
| PT-2 | 27 | TRBV2*01 | TRBJ2-5*01 | TRBD2*01 | tgt gcc agc agt gaa ggg ggt ggg caa gag acc cag tac ttc | CASSEGGGQETQYF * |
| PT-2 | 35 | TRBV2*01 | TRBJ2-5*01 | TRBD2*02 | tgt gcc agc agt gaa ggt ggg gga ggg caa gag acc cag tac ttc | CASSEGGGQETQYF * |
| PT-2 | 67 | TRBV2*01 | TRBJ2-5*01 | TRBD2*02 | tgt gcc agc agt gaa ggg ggt gga gag caa gag acc cag tac ttc | CASSEGGGQETQYF * |
| PT-2 | 70 | TRBV2*01 | TRBJ2-5*01 | TRBD2*01 | tgt gcc agc agt gaa ggc ggt gga ggg caa gag acc cag tac ttc | CASSEGGGQETQYF * |
| PT-2 | 29 | TRBV2*01 | TRBJ2-5*01 | TRBD2*01 | tgt gcc agc agt gaa ggg ggg ggc ctc gcc gcc gag acc cag tac ttc | CASSEGGGLAETQYF * * |
| PT-2 | 34 | TRBV2*01 | TRBJ2-5*01 | TRBD2*01 | tgt gcc agc agt gaa ggg ggg ggc ctc gcc gcc gag acc cag tac ttc | CASSEGGGLAETQYF * * |
| PT-2 | 76-2 | TRBV11-2*01 | TRBJ2-3*01 | TRBD1*01 | tgt gcc agc agt ttt aac agg gtc cga gac cag tat ttt | CASSFNRVRDTQYF |
| PT-2 | 1 | TRBV28*01 | TRBJ1-1*01 | TRBD1*01 | tgt gcc agc agt ttt tcg aca gac ggc act gaa gct ttc ttt | CASSFSTDGTEAFF |
| PT-2 | 54 | TRBV3-1*01 | TRBJ1-4*01 | TRBD1*01 | tgt gcc agc agc gga cga ccg ggt ggt gaa aaa ctg ttt ttt | CASSGRPGGEKLFF |
| PT-2 | 77 | TRBV23-1*01 | TRBJ1-3*01 | TRBD2*01 | tgc cag agt cac ctc cag ggt ta gga aac acc ata tat ttt | CASSHLQG.GNTIYF |
| PT-2 | 63 | TRBV9*01 | TRBJ2-2*01 | TRBD1*01 | tgt gcc agc agc ata gga cat tcc gcc ggg tcc ggg gag ctg ttt ttt | CASSIGHSAGSGELFF |
| PT-2 | 5 | TRBV7-3*01 | TRBJ2-3*01 | TRBD2*01 | tgt gcc agc agc ttg gca ggg ggc ttg gat acg cag tat ttt | CASSLAGGLDTQYF |
| PT-2 | 26 | TRBV5-6*01 | TRBJ2-4*01 | TRBD2*01 | tgt gcc agc agt tta ggc gtc cag cta acc gcc caa gac att cag tac ttc | CASSLAVQLAKNIQYF |
| PT-2 | 15 | TRBV28*01 | TRBJ2-1*01 | TRBD2*02 | tgt gcc agc agt tta ttt tgg gag acc gca caa cag acc cag tac ttc | CASSLFWETAQETQYF * |
| PT-2 | 33 | TRBV28*01 | TRBJ2-1*01 | TRBD2*02 | tgt gcc agc agt tta ttt tgg gag acc gca caa cag acc cag tac ttc | CASSLFWETAQETQYF * |
| PT-2 | 37 | TRBV28*01 | TRBJ2-1*01 | TRBD2*02 | tgt gcc agc agt tta ttt tgg gag acc gca caa gag acc cag tac ttc | CASSLFWETAQETQYF * |
| PT-2 | 50 | TRBV5-4*01 | TRBJ2-1*01 | TRBD1*01 | tgt gcc agc agc tta ggg gcg aga ggg tgg gcc aat gag cag ttc ttc | CASSLGARGWGNEQFF |
| PT-2 | 32 | TRBV28*01 | TRBJ2-7*01 | TRBD1*01 | tgt gcc agc agt tta ttg aca ggg agg act gaa gct ttc ttt | CASSLLTGRTEAFF |
| PT-2 | 76-1 | TRBV7-3*01 | TRBJ2-5*01 | TRBD2*01 | tgt gcc agc agc tta agc gca ggg tct gcc gag cag tac ttc | CASSLSAGSAEQYF |
| PT-2 | 2 | TRBV3-1*01 | TRBJ2-5*01 | TRBD2*01 | tgt gcc agc agc ccg ttt cgg ggg gag att gta gag acc cag tac ttc | CASSPFRGEIVETQYF * |
| PT-2 | 11 | TRBV3-1*01 | TRBJ2-5*01 | TRBD2*01 | tgt gcc agc agc ccg ttt cgg ggg gag att gta gag acc cag tac ttc | CASSPFRGEIVETQYF * |
| PT-2 | 28 | TRBV3-1*01 | TRBJ2-5*01 | TRBD2*01 | tgt gcc agc agc ccg ttt cgg ggg gag att gta gag acc cag tac ttc | CASSPFRGEIVETQYF * |
| PT-2 | 30 | TRBV3-1*01 | TRBJ2-5*01 | TRBD2*01 | tgt gcc agc agc ccg ttt cgg ggg gag att gta gag acc cag tac ttc | CASSPFRGEIVETQYF * |
| PT-2 | 36 | TRBV3-1*01 | TRBJ2-5*01 | TRBD2*01 | tgt gcc agc agc ccg ttt cgg ggg gag att gta gag acc cag tac ttc | CASSPFRGEIVETQYF * |
| PT-2 | 42 | TRBV3-1*01 | TRBJ2-5*01 | TRBD2*01 | tgt gcc agc agc ccg ttt cgg ggg gag att gta gag acc cag tac ttc | CASSPFRGEIVETQYF * |
| PT-2 | 47 | TRBV3-1*01 | TRBJ2-5*01 | TRBD2*01 | tgt gcc agc agc ccg ttt cgg ggg gag att gta gag acc cag tac ttc | CASSPFRGEIVETQYF * |
| PT-2 | 71 | TRBV3-1*01 | TRBJ2-5*01 | TRBD2*01 | tgt gcc agc agc ccg ttt cgg ggg gag att gta gag acc cag tac ttc | CASSPFRGEIVETQYF * |
| PT-2 | 25 | TRBV4-1*01 | TRBJ2-5*01 | TRBD1*01 | tgc gcc agc agt caa gag gcg gag gtc cag tac ttc | CASSQEANRGEVQYF |
| PT-2 | 69 | TRBV14*01 | TRBJ2-7*01 | TRBD2*02 | tgt gcc agc agc cag gga cag tta gcg gga ctc aac tac gag cag tac ttc | CASSQQLAGLNYEQYF |

| | | TRBV | TRBJ | TRBD | Nucleotide sequence | CDR3 |
|---|---|---|---|---|---|---|
| PT-3 | 12 | TRBV6-5*01 | TRBJ2-7*01 | TRBD1*01 | tgt gcc agc agt tcg ccc ggg aca ggg gag tac cag ttc | CASSSPGTGEYEQYF |
| PT-3 | 34 | TRBV18*01 | TRBJ2-1*01 | TRBD1*01 | tgt gcc agc tca tct tac ggg aca ggg ggc gat gag cag ttc | CASSSYGTGGDEQFF * |
| PT-3 | 46 | TRBV18*01 | TRBJ2-1*01 | TRBD1*01 | tgt gcc agc tca tct tac ggg aca ggg ggc gat gag cag ttc | CASSSYGTGGDEQFF * |
| PT-3 | 58 | TRBV6-1*01 | TRBJ1-4*01 | TRBD1*01 | tgt gcc agc aca ggg gcg acc ggg act aat gaa aaa ctg ttt | CASSTGATGTNEKLFF |
| PT-3 | 38 | TRBV9*01 | TRBJ2-3*01 | | tgt gcc agc agc gta gtt ccg aac aca gat acg cag tat ttt | CASSVVPNTDTQYF |
| PT-3 | 8 | TRBV11-3*01 | TRBJ2-1*01 | TRBD2*02 | tgt gcc agc agc tgg ggg tgg gag agc ggg agg gcg ttc gat gag cag ttc | CASSWGWESGRAFDEQFF |
| PT-3 | 28 | TRBV27*01 | TRBJ2-7*01 | TRBD1*01 | tgt gcc agc agt tgg aca ggg tac tcc tac gag cag ttc | CASSWTGTSYEQYF |
| PT-3 | 52 | TRBV6-5*01 | TRBJ1-1*01 | TRBD1*01 | tgt gcc agc agt tat ggg gaa acc gct ttc ttt | CASSYGETAFF |
| PT-3 | 36 | TRBV25-1*01 | TRBJ1-3*01 | TRBD1*01 | tgt gcc agc aca gcg ggg gac acc ata tat ttt | CASTAGDTIYF |
| PT-3 | 50 | TRBV25-1*01 | TRBJ1-3*01 | TRBD1*01 | tgt gcc agc aca gcg ggg gac acc ata tat ttt | CASTAGDTIYF * |
| PT-3 | 70 | TRBV28*01 | TRBJ2-2*01 | TRBD2*01 | tgt gcc acg aaa cag ggg gcc agg act agc gac acc ggg gag ctg ttt ttt | CATKQGARTSDTGELFF |
| PT-3 | 64-1 | TRBV15*01 | TRBJ2-7*01 | TRBD1*01 | tgt gcc aca caa gtc ggg ggc ggc tcc tac gag cag tac ttc | CATQVGGGSYEQYF |
| PT-3 | 66 | TRBV15*01 | TRBJ2-7*01 | TRBD2*02 | tgt gcc acc agc aga ggc cta gcg gga gcc tac gag cag tac ttc | CATSRGLAGAYEQYF |
| PT-3 | 45-2 | TRBV24-1*01 | TRBJ1-1*01 | TRBD1*01 | tgt gcc acc gtg ttg ggg aac act gaa gct ttc ttt | CATVLGNTEAFF |
| PT-3 | 9 | TRBV30*01 | TRBJ1-1*01 | TRBD1*01 | tgt gcc tgg agt cga gga gca gga acc ggg agt gct ttt | CAWSRGAGSNEAFF |
| PT-3 | 51 | TRBV30*01 | TRBJ1-1*01 | TRBD1*01 | tgt gcc tgg agt gtc ttc ggg ggc act gaa gct ttc ttt | CAWSVFGGTEAFF |
| PT-3 | 67 | TRBV29-1*01 | TRBJ2-2*01 | TRBD2*01 | tgc agc gct ggg act agc agt acc ggg gag ctg ttt ttt | CSAGTSSTGELFF |
| PT-3 | 32 | TRBV20-1*01 | TRBJ2-1*01 | TRBD2*02 | tgc agc aga ggg aga ggc cat ggg gag ttc ttc | CSARGAGRGHEQFF * |
| PT-3 | 57 | TRBV20-1*01 | TRBJ2-1*01 | TRBD2*02 | tgt agt gct aga gga gcc cat ggg cat gag cag ttc ttc | CSARGAGRGHEQFF * |
| PT-3 | 60 | TRBV20-1*01 | TRBJ2-1*01 | TRBD2*02 | tgc agt gct aga gga gcc agg cat gag cag ttc ttc | CSARGAGRGHEQFF * |
| PT-3 | 74 | TRBV20-1*01 | TRBJ2-1*01 | TRBD2*02 | tgc agt gct agg aga gca agg ggc cat gag cag ttc ttc | CSARGAGRGHEQFF * |
| PT-3 | 56 | TRBV20-1*01 | TRBJ2-1*01 | TRBD2*01 | tgc agt gct aga ggg ccg ttg cgg ttc tat gag cag ttc | CSARGPLRFYEQFF |
| PT-4 | 52 | TRBV10-3*01 | TRBJ2-5*01 | TRBD2*01 | tgt gcc atc agt gag tcg ggc ggt ggg tca gag acc cag tac ttc | CAISESGGGSETQYF |
| PT-4 | 10 | TRBV12-5*01 | TRBJ2-1*01 | TRBD2*02 | tgt gct agt ggt ttg tcc agg act agc ggg act atg tcc tac aat gag cag ttc | CASGLSRTSGTMSYNEQFF |
| PT-4 | 52 | TRBV9*01 | TRBJ2-1*01 | TRBD1*01 | tgc agc agt aac ccc aag ggc cag ggg cag gac acc ggg gag ctg ttt ttt | CASGNPKGQGQDTGELFF |
| PT-4 | 37-1 | TRBV28*01 | TRBJ2-3*01 | TRBD1*01 | tgc agc agt aaa act gta aac agg gga ttt ggg aca gat acg cag tat ttt | CASKTVNRGFGTDTQYF |
| PT-4 | 16 | TRBV2*01 | TRBJ2-1*01 | TRBD2*01 | tgc agc caa aac tta gcg ggc cct cag tac aat gag cag ttc ttc | CASQNLAGPQYNEQFF |
| PT-4 | 44 | TRBV27*01 | TRBJ2-1*01 | TRBD2*01 | tgc agc agc agg gga cta tac aat gag cag ttc | CASRGLYNEQFF |
| PT-4 | 25 | TRBV25-1*01 | TRBJ1-1*01 | TRBD2*01 | tgc agc agt ccg cgt cca ggc aca gat acg cag tat ttt | CASRPGTDTQYF |
| PT-4 | 39 | TRBV27*01 | TRBJ1-1*01 | TRBD1*01 | tgc agc agt gct gac tgg gac gcc gga gct gaa gct ttc ttt | CASSADWDREAEAFF |
| PT-4 | 21 | TRBV9*01 | TRBJ2-3*01 | TRBD2*01 | tgc agc agt gcc ggc ggg gac cca gat acg cag tat ttt | CASSAGDPDTQYF |
| PT-4 | 49 | TRBV27*01 | TRBJ1-2*01 | TRBD1*01 | tgc agc agc tct ggc agg ggt act aat ggc tac acc ttc | CASSAGGTNYGYTF * |
| PT-4 | 51 | TRBV27*01 | TRBJ1-2*01 | TRBD1*01 | tgc agc agc tct ggc agg ggt act aac tat ggc tac acc ttc | CASSAGGTNYGYTF * |
| PT-4 | 29 | TRBV27*01 | TRBJ1-2*01 | TRBD1*01 | tgc agc agc tct ggc agg gtt act aac tat ggc tac acc ttc | CASSAGGTNYGYTF * |
| PT-4 | 62 | TRBV28*01 | TRBJ1-1*01 | TRBD2*01 | tgc agc agt gct gga ggc aac act gaa gct ttc ttt | CASSAGTGGNTEAFF |
| PT-4 | 20 | TRBV9*01 | TRBJ2-7*01 | TRBD1*01 | tgc agc agc agt ggt tac acc gag tac gag cag tac ttc | CASSASSGTTYEQYF |
| PT-4 | 42 | TRBV2*01 | TRBJ2-4*01 | TRBD2*02 | tgc agc agt gag tgg caa cac gga ggc aat tca ccc ctc cac ttt | CASSEWQGNSPLHF |
| PT-4 | 31 | TRBV28*01 | TRBJ2-7*01 | TRBD1*01 | tgc agc agt ttc gca gaa gcc tac gag cag tac ttc | CASSFAEAYEQYF |
| PT-4 | 31 | TRBV12-3*01 | TRBJ1-1*01 | TRBD1*01 | tgc agc agt ttc gag gga cgt aga tac gag cag tac ttc | CASSFETGRYEQYF |
| PT-4 | 26 | TRBV28*01 | TRBJ1-1*01 | TRBD1*01 | tgc agc agt ttt ggg cct aac act gaa gct ttc ttt | CASSFGGPNTEAFF |
| PT-4 | 32 | TRBV27*01 | TRBJ2-1*01 | TRBD1*01 | tgc agc agt ttt gga tta gcg aaa tac aat gag cag ttc ttc | CASSFGLAKYNEQFF |
| PT-4 | 35 | TRBV6-2*01 | TRBJ2-7*01 | TRBD2*01 | tgc agc agt ttc agt gtc gcc tac gag cag tac ttc | CASSFSVAYEQYF |
| PT-4 | 8 | TRBV28*01 | TRBJ1-1*01 | TRBD1*01 | tgc agc agt ttc tac agc acc aat acc ggg gag ctg ttt ttt | CASSFYSTNTGELFF |
| PT-4 | 12 | TRBV4-2*01 | TRBJ2-2*01 | TRBD2*02 | tgc agc agc cac gag cgg cgg aac acc ggg gag ctg ttt ttt | CASSHERERNTGELFF |
| PT-4 | 14 | TRBV6-5*01 | TRBJ1-1*01 | TRBD1*01 | tgc agc agt tac agg ggc gca gat acg cag tat ttt | CASSHRAADTQYF |
| PT-4 | 22 | TRBV27*01 | TRBJ1-1*01 | TRBD1*01 | tgc agc agt tta gcg agt agt aac act gaa gct ttc ttt | CASSLAGSNTEAFF |
| PT-4 | 66 | TRBV5-4*01 | TRBJ2-1*01 | TRBD2*02 | tgc agc agc tta gaa cta gga gac cag ggc gat gag cag tac ttc | CASSLELAGDEQYF |
| PT-4 | 54 | TRBV28*01 | TRBJ1-4*01 | TRBD1*01 | tgc agc agc tta gaa cag ggg ggc aat gaa aaa ctg ttt ttt | CASSLEQGGNEKLFF |
| PT-4 | 44 | TRBV11-2*01 | TRBJ2-5*01 | TRBD2*02 | tgc agc agc tta gaa tct gtg aac caa ggg acc cag tac ttt | CASSLESVNQETQYF |
| PT-4 | 13 | TRBV6-2*01 | TRBJ2-2*01 | TRBD1*01 | tgc agc agt ttg gaa acg ctg aac acc ggg gag ctg ttt ttt | CASSLETLNTGELFF |
| PT-4 | 38 | TRBV7-2*01 | TRBJ1-2*01 | TRBD1*01 | tgc agc agt tta ggg gct gct ggc acc tac ggc tac acc ttc | CASSLGAGTGELFF |
| PT-4 | 57 | TRBV6-5*01 | TRBJ2-7*01 | TRBD1*01 | tgc agc agt ttg ggg gct ccc tac gag cag tac ttc | CASSLGAPYEQYF |
| PT-4 | 3 | TRBV7-9*01 | TRBJ2-3*01 | TRBD1*01 | tgc agc agt tta gga aca ggc aca gat acg cag tat ttt | CASSLGTGTDTQYF |
| PT-4 | 40 | TRBV7-6*01 | TRBJ2-1*01 | TRBD2*01 | tgc agc agc ttg ggg act agc gat gag cag ttc ttc | CASSLGTSDEQFF |
| PT-4 | 63 | TRBV7-3*01 | TRBJ2-1*01 | TRBD2*01 | tgc agc agc tta gac ggg ggt tcc tac aat gag cag ttc | CASSLLDGGSYNEQFF |
| PT-4 | 36-1 | TRBV7-2*01 | TRBJ2-7*01 | TRBD1*01 | tgc agc agc ctt ccg ggg ggc agt agt tac gag cag tac ttc | CASSLPGGSSYEQYF |
| PT-4 | 68 | TRBV7-2*02 | TRBJ2-7*01 | TRBD1*01 | tgc agc agc tta caa cag ggt tgg tac gag cag tac ttc | CASSLQQGWYEQYF |
| PT-4 | 25 | TRBV7-2*01 | TRBJ2-1*01 | TRBD2*02 | tgt gcc agc agc tta agg ccc aat gag cag ttc ttc | CASSLRPNEQFF |

| | | | | | | |
|---|---|---|---|---|---|---|
| PT-5 | 4 | TRBV2*01 | TRBJ1-3*01 | TRBD1*01 | tgt gcc agc aga gat cgg aga aac acc ata tat ttt | CASRDRRNTYF |
| PT-5 | 18 | TRBV6-5*01 | TRBJ2-1*01 | TRBD2*02 | tgt gcc agc aga cta cgg gga gtc ccc tcg gat gag cag ttc ttc | CASRLLAGVPSDEQFF |
| PT-5 | 67 | TRBV19*01 | TRBJ1-5*01 | TRBD1*01 | tgt gcc agt agt gcg gac agg ggg ctt att cag ccc cag cat ttt | CASSADRGLIQPQHF |
| PT-5 | 62 | TRBV11-2*01 | TRBJ2-3*01 | TRBD2*01 | tgt gcc agc agc gca aca gga gga ttc aca gat acg cag tat ttt | CASSATGGFTDTQYF |
| PT-5 | 43 | TRBV7-9*01 | TRBJ2-1*01 | TRBD2*01 | tgt gcc agc agc gac gcg aag gag cag tac ttc | CASSDAKEQYF * |
| PT-5 | 60 | TRBV7-9*01 | TRBJ2-1*01 | TRBD2*01 | tgt gcc agc agc gac gcg aag gag cag tac ttc | CASSDAKEQYF * |
| PT-5 | 35 | TRBV10-2*01 | TRBJ2-7*01 | TRBD1*01 | tgc gcc agc agc cac cgt ccg ggg cac tac ttc | CASSDHGPGQYF |
| PT-5 | 49—1 | TRBV2*01 | TRBJ2-5*01 | TRBD1*01 | tgt gcc agc agt gaa gcg cat tgg gac agg caa gag acc cag ttt | CASSEAHWDRQETQYF |
| PT-5 | 37—2 | TRBV7-8*01 | TRBJ2-2*01 | TRBD1*01 | tgt gcc agc ago ttc ggg aca ggg aga ago ggg gag ctg ttt | CASSFGTGRSGELFF |
| PT-5 | 39 | TRBV7-9*01 | TRBJ2-6*01 | TRBD2*02 | tgt gcc agc agc ttt tca gga gac cct ggg gcc aac gtc ctg act ttc | CASSFSGDPGANVLTF |
| PT-5 | 59 | TRBV10-2*01 | TRBJ2-2*01 | TRBD2*02 | tgt gcc agc agc ggg agg tgg tac aat gag cag ttc ttc | CASSGRWYNEQFF |
| PT-5 | 40 | TRBV9*01 | TRBJ2-2*01 | TRBD2*01 | tgt gcc agc cat gct ggg ggg agc cgt ggc acc ggg gag ctg ttt ttt | CASSHAGGSRGTGELFF |
| PT-5 | 9 | TRBV2*01 | TRBJ1-1*01 | TRBD1*01 | tgt gcc agc agc att ggg acc ttg aac act gaa gct ttc ttt | CASSIGTLNTEAFF * |
| PT-5 | 21 | TRBV2*01 | TRBJ1-1*01 | TRBD1*01 | tgt gcc agc agc att ggg acc ttg aac act gaa gct ttc ttt | CASSIGTLNTEAFF * |
| PT-5 | 13 | TRBV28*01 | TRBJ2-3*01 | TRBD2*01 | tgt gcc agt ctg gcg gat acg cag tat ttt | CASSLADTQYF |
| PT-5 | 83 | TRBV27*01 | TRBJ2-3*01 | TRBD1*01 | tgt gcc agc agt ctt gac aag gat acg cag tat ttt | CASSLDKDTQYF |
| PT-5 | 82 | TRBV3-1*01 | TRBJ2-1*01 | TRBD1*01 | tgt gcc agc agc cta gac agt gcc tcc tac aat gag cag ttc ttc | CASSLDSASYNEQFF |
| PT-5 | 36 | TRBV7-9*01 | TRBJ2-6*01 | TRBD1*01 | tgt gcc agc agc tta gac agt atc tcc tac tct ggg gcc aac gtc ctg act ttc | CASSLDSISYSGANVLTF |
| PT-5 | 14 | TRBV7-3*01 | TRBJ2-1*01 | TRBD2*02 | tgt gcc agc agc tta gaa ggg tta aat gag cag ttc ttc | CASSLEGLNEQFF |
| PT-5 | 50 | TRBV5-8*01 | TRBJ2-2*01 | TRBD2*02 | tgt gcc agc agc ttg gaa cgg gag atg aac acc ggg gag ctg ttt ttt | CASSLEREMNTGELFF |
| PT-5 | 74 | TRBV7-9*01 | TRBJ2-7*01 | TRBD1*01 | tgt gcc agc agc tta gag tca gac tcg ccc tac gag cag tac ttc | CASSLESDSPYEQYF |
| PT-5 | 48 | TRBV7-9*01 | TRBJ2-2*01 | TRBD2*01 | tgt gcc agc agc tta gga cta gcg ggc tac acc ggg gag ctg ttt ttt | CASSLGLAGYTGELFF |
| PT-5 | 10—1 | TRBV28*01 | TRBJ2-4*01 | TRBD1*01 | tgt gcc agc agt tta cag gga aac att cag tac ttc | CASSLLQGNIQYF |
| PT-5 | 27 | TRBV28*01 | TRBJ1-5*01 | TRBD1*01 | tgt gcc agc agt cta ccg aca ggg gaa cag ccc cag cat ttt | CASSLPTGEGPQHF |
| PT-5 | 80 | TRBV28*01 | TRBJ2-7*01 | TRBD2*02 | tgt gcc agc agt tta tct agc ggg aga tac gag cag tac ttc | CASSLSSGRYEQYF * |
| PT-5 | 20—2 | TRBV28*01 | TRBJ2-7*01 | TRBD2*02 | tgt gcc agc agt tta tct agc ggg aga tac gag cag tac ttc | CASSLSSGRYEQYF * |
| PT-5 | 24 | TRBV7-3*01 | TRBJ2-1*01 | TRBD2*01 | tgt gcc agc agc ccc gga cta gac ccc tac cat gag cag ttc ttc | CASSPGLDPYHEQFF |
| PT-5 | 12 | TRBV7-3*01 | TRBJ2-1*01 | TRBD2*01 | tgt gcc agc agc ccc gga cta gac ccc tac aat gag cag ttc ttc | CASSPGLDPYNEQFF * |
| PT-5 | 66 | TRBV7-3*01 | TRBJ2-1*01 | TRBD2*01 | tgt gcc agc agc ccc gga cta gac ccc tac aat gag cag ttc ttc | CASSPGLDPYNEQFF * |
| PT-5 | 11—1 | TRBV7-3*01 | TRBJ2-1*01 | TRBD2*01 | tgt gcc agc agc ccc gga cta gac ccc tac aat gag cag ttc ttc | CASSPGLDPYNEQFF * |
| PT-5 | 78 | TRBV7-8*01 | TRBJ2-1*01 | TRBD2*02 | tgt gcc agc agc ccc tta gcg gga ggg cct cag aat gag cag ttc ttc | CASSPLAGGPQNEQFF * |
| PT-5 | 25 | TRBV11-2*01 | TRBJ2-5*01 | TRBD2*01 | tgt gcc agc agc cca caa ccg gga cta gga gga tac acc cag gag tac ttc | CASSPQPGLGAETQYF |
| PT-5 | 51 | TRBV27*01 | TRBJ1-5*01 | TRBD1*01 | tgt gcc agc agt ccc caa agc tac agg gtt gac cag ccc cag cat ttt | CASSPQSYRVDQPQHF |
| PT-5 | 28 | TRBV4-2*01 | TRBJ2-3*01 | TRBD2*01 | tgt gcc agc agc caa gat gcc ggg gac aca gat acg cag tat ttt | CASSQDGGDTDTQYF * |
| PT-5 | 57 | TRBV4-2*01 | TRBJ2-3*01 | TRBD2*01 | tgt gcc agc agc caa gat gcc ggg gac aca gat acg cag tat ttt | CASSQDGGDTDTQYF * |
| PT-5 | 68 | TRBV4-1*01 | TRBJ1-1*01 | TRBD1*01 | tgc gcc agc agc caa gat cag ggg ata ata gaa gct ttc ttt | CASSQDGIIEAFF |
| PT-5 | 19 | TRBV4-1*01 | TRBJ1-1*01 | TRBD2*02 | tgc gcc agc agc caa gag tcg ttg aac act gaa gct ttc ttt | CASSQESLNTEAFF * |
| PT-5 | 55 | TRBV4-1*01 | TRBJ1-1*01 | TRBD2*02 | tgc gcc agc agc caa gag tcg ttg aac act gaa gct ttc ttt | CASSQESLNTEAFF * |
| PT-5 | 88 | TRBV5-5*01 | TRBJ2-1*01 | TRBD1*01 | tgt gcc agc cga gag cgc tac aat gag cag ttc ttc | CASSRERYNEQFF |
| PT-5 | 79 | TRBV12-3*01 | TRBJ1-2*01 | TRBD1*01 | tgt gcc agc agt tca gct aac tat ggc tac acc ttc | CASSSANVGYTF |
| PT-5 | 81 | TRBV7-2*02 | TRBJ2-1*01 | | tgt gcc agc agt tct gtc ccg tac aat gag cag ttc ttc | CASSSVPYNEQFF |
| PT-5 | 76 | TRBV9*01 | TRBJ1-3*01 | TRBD2*01 | tgt gcc agt agc gta ggg ggg ttg gcc agc tct gga aac acc ata tat ttt | CASSVGGLAVSSGNTIYF |
| PT-5 | 69—1 | TRBV7*01 | TRBJ2-1*01 | TRBD2*01 | tgt gcc agc agt tgg gta gga gac tac caa gag acc cag tac ttc | CASSWVGDYQETQYF |
| PT-5 | 26 | TRBV6-2*01 | TRBJ1-1*01 | TRBD1*01 | tgt gcc agc agt tac ctt ggg gcc acc aat gaa gct ttc ttt | CASSYLGATNEAFF |
| PT-5 | 3 | TRBV6-5*01 | TRBJ2-1*01 | TRBD2*01 | tgt gcc agc agt tac tcg aag gga cta gcg gac tcc tac gag cag tac ttc | CASSYSKGLADSYEQYF |
| PT-5 | 29 | TRBV6-2*01 | TRBJ2-5*01 | TRBD1*01 | tgt gcc agc agt tac tcc tcg aca agc caa gag acc cag tac ttc | CASSYSSRTQETQYF |
| PT-5 | 71 | TRBV28*01 | TRBJ1-5*01 | TRBD1*01 | tgt gcc agc acc gcc cct cga ccc cag cat ttt | CASTAPRQPQHF |
| PT-5 | 8 | TRBV19*01 | TRBJ2-1*01 | TRBD2*01 | tgt gcc agt aca ggg tca ata ttc aat gag cag ttc ttc | CASTGSIFNEQFF |
| PT-5 | 77 | TRBV6-2*01 | TRBJ2-2*01 | TRBD1*01 | tgt gcc agc acc tta ggg cag acc ggg gag ctg ttt ttt | CASTLGQTGELFF |
| PT-5 | 15 | TRBV19*01 | TRBJ2-2*01 | TRBD2*02 | tgt gcc agc acc ggg cta gcg ggg gtc gag ggg gag ggg ctg ttt ttt | CASTNGLAGVEGELFF |
| PT-5 | 1 | TRBV27*01 | TRBJ2-2*01 | TRBD2*02 | tgt gcc agc tac gga agg gtt agc acc ggg gag ctg ttt ttt | CASYGRVSTGELFF * |
| PT-5 | 47 | TRBV27*01 | TRBJ2-2*01 | TRBD2*02 | tgt gcc agc tac gga agg gtt agc acc ggg gag ctg ttt ttt | CASYGRVSTGELFF * |
| PT-5 | 72 | TRBV10-3*01 | TRBJ1-5*01 | TRBD1*01 | tgt gcc agc aca ggg agt agc aat cag ccc cag cat ttt | CATGTGDSNQPQHF |
| PT-5 | 38—1 | TRBV2*01 | TRBJ2-5*01 | TRBD2*01 | tgt gcc acc ggg act agc ggg tac cgg gag acc cag tac ttc | CATGTSGYRETQYF |
| PT-5 | 34—2 | TRBV2*01 | TRBJ2-1*01 | TRBD2*02 | tgt gcc acg cac gag gct agc ggg aaa tgg gcc cag gag acc cag tac ttc | CATHEASGKWQETQYF |
| PT-5 | 54 | TRBV24-1*01 | TRBJ2-2*01 | TRBD1*01 | tgt gcc acc agt gat tct ccg gga cag gga tcc ggg gag ctg ttt ttt | CATSDSPGQGSGELFF |
| PT-5 | 44 | TRBV24-1*01 | TRBJ1-1*01 | TRBD2*01 | tgt gcc acc agt ccc gga act agc aga cta agc aat gag cag ttc ttc | CATSPGTSGRLSNEQFF |
| PT-5 | 87 | TRBV24-1*01 | TRBJ2-2*01 | TRBD2*02 | tgt gcc gta aga aag atc aac acc ggg gag ctg ttt ttt | CATVRKINTGELFF |

Fig. 2M

| | | | | | | | |
|---|---|---|---|---|---|---|---|
| PT-5 | 86 | TRBV30*01 | TRBJ2-1*01 | TRBD2*02 | tgt gcc tgg aag ggt gag ggt gct gag ttc ttc | CAWKGEGAEQFF |
| PT-5 | 22 | TRBV20-1*01 | TRBJ2-7*01 | TRBD2*01 | tgc agt gct aga agt ggg act agc gca ccc gag tac ttc | CSARSGTSAPYEQYF* |
| PT-5 | 75 | TRBV20-1*01 | TRBJ2-7*01 | TRBD2*01 | tgc agt gct aga agt ggg act agc gca ccc tac gag cag tac ttc | CSARSGTSAPYEQYF* |
| PT-5 | 17 | TRBV20-1*01 | TRBJ1-1*01 | TRBD1*01 | tgc agt gct aga act ggg ggg gct gaa gct ttc ttt | CSARTGGAEAFF** |
| PT-5 | 23 | TRBV20-1*01 | TRBJ1-1*01 | TRBD1*01 | tgc agt gct aga act ggg ggg gct gaa gct ttc ttt | CSARTGGAEAFF** |
| PT-5 | 52 | TRBV20-1*01 | TRBJ1-1*01 | TRBD1*01 | tgc agt gct aga act ggg ggg gct gaa gct ttc ttt | CSARTGGAEAFF** |
| PT-5 | 65 | TRBV20-1*01 | TRBJ1-6*01 | TRBD1*01 | tgc agt gct gct agc ccc ggg aca gat aat tca ccc ctc cac ttt | CSASPGTDNSPLHF |
| PT-5 | 42 | TRBV20-1*01 | TRBJ2-7*01 | TRBD1*01 | tgc agt gct agc agc cct cgc ccg cgt ggc gga tcc tac gag cag tac ttc | CSASRPRPGGSYEQYF |
| PT-5 | 93 | TRBV29-1*01 | TRBJ1-1*01 | TRBD2*01 | tgc agc gtt gaa gct agc ggg tgg ggg aag gat acg cag tat ttt | CSVEASGWGKDTQYF |
| PT-6 | 19 | TRBV6-1*01 | TRBJ2-4*01 | TRBD2*01 | tgt gcc agc tgt gac ggg act aga gag agt gac att cag tac ttc | CASCDGTRESDIQYF |
| PT-6 | 14 | TRBV6-1*01 | TRBJ1-2*01 | TRBD1*01 | tgc gcc agt gga ggg ttt gag aaa tat ggc tac acc ttc | CASGGFEKYGYTF |
| PT-6 | 31 | TRBV27*01 | TRBJ2-1*01 | TRBD2*02 | tgc agc agc cga cga ggg tac aat gag cag ttc ttc | CASRRGYNEQFF |
| PT-6 | 7 | TRBV6-1*01 | TRBJ1-5*01 | TRBD1*01 | tgt gcc agc agt gcg gcc gaa tcc aat gca tcc aat ccc cag cat ttt | CASSEAAESNQPQHF |
| PT-6 | 12 | TRBV6-1*01 | TRBJ2-3*01 | TRBD2*01 | tgt gcc agt gaa gcg gga ggg ctt gat acg cag tat ttt | CASSEGAGGLDTQYF |
| PT-6 | 26 | TRBV2*01 | TRBJ2-3*01 | TRBD1*01 | tgt gcc agt gaa aca ggg tct agc aca gat acg cag tat ttt | CASSETGSSTDTQYF |
| PT-6 | 4 | TRBV2*01 | TRBJ2-2*01 | TRBD1*01 | tgc agc agc agt gaa tgg aca ggg gat acc ggg gag ctg ttt ttt | CASSEWTGDTGELFF* |
| PT-6 | 27 | TRBV2*01 | TRBJ2-2*01 | TRBD1*01 | tgc agc agc agt gaa tgg aca ggg gat acc ggg gag ctg ttt ttt | CASSEWTGDTGELFF* |
| PT-6 | 9 | TRBV28*01 | TRBJ1-1*01 | TRBD1*01 | tgt gcc agc agt ttc cag gga tac act gaa gct ttc ttt | CASSFQQYTEAFF |
| PT-6 | 11 | TRBV12-3*01 | TRBJ1-6*02 | TRBD1*01 | tgt gcc agc agt ttt tgg ggc cct gac gat tca ccc ctc cac ttt | CASSFWGPDDSPLHF |
| PT-6 | 3 | TRBV10-1*01 | TRBJ2-1*01 | TRBD2*02 | tgc gcc agc agt ggc ggt agc ggg agt aca ttt ccc aat gag cag ttc ttc | CASSGGSGSTFPNEQFF |
| PT-6 | 10 | TRBV19*01 | TRBJ1-2*01 | TRBD1*01 | tgt gcc agt agc ata gac gcg gac agg gga ttg ggc ggt tac acc ttc | CASSIDADRGLGGYTF |
| PT-6 | 25 | TRBV19*01 | TRBJ2-1*01 | TRBD1*01 | tgt gcc agt agt atc gta caa acc aat gag cag ttc ttc | CASSIVQTNEQFF |
| PT-6 | 5 | TRBV19*01 | TRBJ1-1*01 | TRBD1*01 | tgc cca agt agt tta ggg aca gga atg aac act gaa gct ttc ttt | CASSLQTGEMNTEAFF |
| PT-6 | 11 | TRBV2*01 | TRBJ2-2*01 | TRBD2*02 | tgt gcc agc agc ctc gta gga gag gtg tca ctc ttc | CASSLVGEVSLF |
| PT-6 | 1 | TRBV28*01 | TRBJ2-2*01 | TRBD1*01 | tgt gcc agt agt tta tat ggg gag ctg ttt ttt | CASSLYGGELFF |
| PT-6 | 10 | TRBV25-1*01 | TRBJ2-2*01 | TRBD1*01 | tgt gcc agc agt ccc gga cag ttc gac acc ggg gag ctg ttt ttt | CASSPGQFDTGELFF |
| PT-6 | 41 | TRBV4-3*01 | TRBJ2-1*01 | TRBD2*01 | tgc agc agc caa gat tta act agc ggg gat gag cag ttc ttc | CASSQDLTSGDEQFF |
| PT-6 | 24 | TRBV4-3*01 | TRBJ1-1*01 | TRBD2*01 | tcc agc agc caa gat agg ggg cgg gtc gga tgg act gaa gct ttc ttt | CASSQDRRGVGWTEAFF |
| PT-6 | 28 | TRBV14*01 | TRBJ2-7*01 | TRBD1*01 | tgc agc agc caa gat gta atg gac gag cag tac ttc | CASSQDYVMDEGYF |
| PT-6 | 3 | TRBV12-3*01 | TRBJ1-2*01 | TRBD1*01 | tgt gcc agc agc agt tca gcg aac tat ggc tac acc ttc | CASSSANYGYTF |
| PT-6 | 8 | TRBV6-2*01 | TRBJ2-1*01 | TRBD1*01 | tgt gcc agc agt tgg ggt gac aat gag cag ttc ttc | CASSWGADNEQFF |
| PT-6 | 13 | TRBV6-2*01 | TRBJ2-7*01 | TRBD1*01 | tgt gcc agc agt tac ggg cta gcg ggc tcc tac gag cag tac ttc | CASSYGLAGSYEQYF |
| PT-6 | 16 | TRBV6-2*01 | TRBJ2-3*01 | TRBD2*01 | tgc agc agc agt tac tcg gac agc caa gat tac act agc ggg gat acg cag tat ttt | CASSYSSDRVSDTQYF* |
| PT-6 | 19 | TRBV6-2*01 | TRBJ2-3*01 | TRBD2*01 | tgc agc agc agt tac tcg gac agg gta tca gat acg cag tat ttt | CASSYSSDRVSDTQYF* |
| PT-6 | 15 | TRBV6-2*01 | TRBJ2-3*01 | TRBD2*01 | tgc agc agc agt tac tcg gac agg gta tca gat acg cag tat ttt | CASSYSSDRVSDTQYF* |
| PT-6 | 23 | TRBV6-2*01 | TRBJ2-7*01 | TRBD2*01 | tgc agc agc agt tac tcg aca aac tcc tac gag cag tac ttc | CASSYSTNSYEQYF |
| PT-6 | 30 | TRBV6-2*01 | TRBJ2-7*01 | TRBD1*01 | tgt gcc agc agt tac tcg act agc gcc tac gag cag tac ttc | CASSYSTSAYEQYF |
| PT-6 | 34 | TRBV19*01 | TRBJ2-1*01 | TRBD2*02 | tgt gcc agt agt acg gcg gga gcc ttt acc tac aat gag cag ttc ttc | CASTAGAFTYNEQFF |
| PT-6 | 43 | TRBV6-2*01 | TRBJ2-7*01 | TRBD1*01 | tgt gcc agc agc gct cag gga cag atc atc tcc tac gag cag tac ttc | CASTAGQGQIISYEQYF |
| PT-6 | 1 | TRBV15*01 | TRBJ2-3*01 | TRBD1*01 | tgc acc agc aga gat atg cta aca gat acg cag tat ttt | CATSRDMLTDTQYF* |
| PT-6 | 38 | TRBV15*01 | TRBJ2-3*01 | TRBD2*01 | tgc acc agc aga gat atg cta aca gat acg cag tat ttt | CATSRDMLTDTQYF* |
| PT-6 | 15 | TRBV15*01 | TRBJ1-3*01 | TRBD2*01 | tgc acc agc acc att cct ggg gaa gcc ata tat ttt | CATSIPGEAIYF** |
| PT-6 | 36 | TRBV15*01 | TRBJ1-3*01 | TRBD1*01 | tgc acc agc tca att cct ggg gaa gcc ata tat ttt | CATSIPGEAIYF** |
| PT-6 | 28 | TRBV15*01 | TRBJ1-3*01 | TRBD1*01 | tgc acc agc tca att cct ggg gaa gcc ata tat ttt | CATSIPGEAIYF** |
| PT-6 | 27 | TRBV15*01 | TRBJ2-7*01 | TRBD1*01 | tgc acc agc acc aca gga cag ggc tac gag cag tac ttc | CATSTGQGYEQYF |
| PT-6 | 2 | TRBV27*01 | TRBJ2-7*01 | TRBD2*02 | tgt gcc acc tgg gga cag gaa gcg gct gcc ggc tcc tac gag cag tac ttc | CATWGGAAGSYEQYF |
| PT-6 | 21 | TRBV20-1*01 | TRBJ1-6*02 | TRBD1*01 | tgc agt gcc gga cag gaa agc tca acc ctc cac ttt | CSAGQGESSPLHF |
| PT-6 | 42 | TRBV20-1*01 | TRBJ2-1*01 | TRBD1*01 | tgc agt gcc ccg gga cag ccg tac aat gag cag ttc ttc | CSAPGQPYNEQFF |
| PT-6 | 30 | TRBV20-1*01 | TRBJ2-1*01 | TRBD1*01 | tgc agt gcc caa gga ctg tat cct aat gag cag ttc ttc | CSAQGLYPNEQFF |
| PT-6 | 16 | TRBV20-1*01 | TRBJ2-7*01 | TRBD2*01 | tgc agt gct aga gag gat tac gag cag tac ttc | CSAREDYEQYF |
| PT-6 | 17 | TRBV20-1*01 | TRBJ2-5*01 | TRBD1*01 | tgc agt gct aga gga gga gac gaa gag acc cag tac ttc | CSARGDEETQYF |
| PT-6 | 5 | TRBV29-1*01 | TRBJ1-5*01 | TRBD1*01 | tgc agt gct agc ttt gag aca gag ctc aat cag ccc cag cat ttt | CSASFETELNQPQHF |
| PT-6 | 7 | TRBV20-1*01 | TRBJ2-1*01 | TRBD1*01 | tgc agt gct agc tct cta gcg ggc aat gag cag ttc ttc | CSASSLAGNEQFF* |
| PT-6 | 39 | TRBV20-1*01 | TRBJ2-1*01 | TRBD2*01 | tgc agt gct agc tct cta gcg ggc aat gag cag ttc ttc | CSASSLAGNEQFF* |
| PT-6 | 32 | TRBV20-1*01 | TRBJ2-1*01 | TRBD2*01 | tgc agt gct agc tct cta gcg ggc aat gag cag ttc ttc | CSASSLAGNEQFF* |

RECEPTOR GENE FOR PEPTIDE CANCER ANTIGEN-SPECIFIC T CELL

CROSS REFERENCE TO RELATED APPLICATIONS

The present application is a divisional of U.S. patent application Ser. No. 14/129,695, filed on Dec. 27, 2013, the text of which is incorporated by reference, which is a National Stage entry under 35 U. S. C. 371 of PCT/JP 12/065707, filed on Jun. 20, 2012 and claims priority to Japanese Patent Application No. 2011-143273, filed on Jun. 28, 2011.

TECHNICAL FIELD

The present invention relates to a polynucleotide contained in the gene for a cancer antigen-specific T-cell receptor, and the peptide encoded by the polynucleotide, and to cancer tests, e.g., diagnosis, prognosis, or treatment monitoring using the same, cancer therapy, and the like.

BACKGROUND ART

Cancer treatments include extirpation of cancer by surgical operation, radiotherapy, treatment with anti-cancer medication, and immunotherapy. Among these treatments, immunotherapy in particular has drawn attention in recent years because it is a treatment more selective and specific against cancer with least side effects. Inter alia, attempts have been extensively made to treat cancer and leukemia by targeting WT1 protein, which is abundantly present in many types of cancer cells and leukemia cells. In order to study the mechanism of the WT1-targeted anti-cancer therapy and to further increase the effect of the therapy, it is necessary to identify the nucleotide sequences of the T-cell receptor (TCR) genes of WT1-specific cytotoxic T-cells (CTL) and the amino acid sequences of the receptor peptides encoded by the nucleotide sequences. However, up to the present date, there is little information about the sequences of those receptor genes and the receptor peptides, and uses thereof although a number of researches have been conducted (see, e.g., patent document 1 and non-patent documents 1-5).

PRIOR ART DOCUMENTS

Patent Documents

Patent Document 1: WO 2008/108257 A1

Non Patent Documents

Non Patent Document 1: Valmori D. et al., J. Immunol. 168: 4231-4240, 2002
Non Patent Document 2: Dietrich P Y. et al., Cancer Res. 61: 2047-2054, 2001
Non Patent Document 3: Coulie P G. et al., Proc. Natl. Acad. Sci. U.S.A. 98: 10290-10295, 2001
Non Patent Document 4: Godelaine D. et al. J. Immunol. 171: 4893-4897, 2003
Non Patent Document 5: Mandruzzato S. et al., J. Immunol. 169: 4017-4024, 2002

SUMMARY OF THE INVENTION

Problems to be Solved by the Invention

An object of the present invention has been to reveal the amino acid sequences of T-cell receptors (TCRs) of WT1-specific cytotoxic T-cells (CTLs) for WT1 protein, and the nucleotide sequences of the genes encoding them, in particular, the amino acid and nucleotide sequences of the CDR3 region of them, as well as to use those pieces of information in cancer tests (diagnosis, prognosis, treatment monitoring, or the like) and in cancer therapy.

Means for Solving the Problems

To accomplish the above object, the inventors have conducted extensive research and determined, for the first time, the nucleotide and amino acid sequences of CDR3 of the Vβ chain of T-cell receptors (TCRs) of WT1-specific cytotoxic T-cells (CTLs) from healthy individuals and HLA-A*0201-positive patients, and has thereby completed the present invention. In particular, the inventors have identified, for the first time, the base sequences of genes for T-cell receptors (TCRs) of WT1-specific cytotoxic T-cells recognizing WT1 cancer antigen peptide (126th-134th amino acids of WT1 protein; RMFPNAPYL (SEQ ID No.: 1543)).

Thus, the present invention provides the following:
(1) A polynucleotide having a nucleotide sequence encoding CDR3 of a Vβ chain of a T-cell receptor (TCR) of a WT1-specific cytotoxic T-cell (CTL), wherein said polynucleotide has DNA having any of the CDR3 nucleotide sequences shown in SEQ ID Nos.: 1-756, RNA complementary to the DNA, or a complementary sequence thereof;
(2) The polynucleotide according to (1), wherein said polynucleotide consists of a DNA consisting of any of the CDR3 nucleotide sequences shown in SEQ ID Nos.: 1-756, or an RNA complementary thereto, or a complementary sequence thereof;
(3) A peptide having an amino acid sequence of CDR3 of a Vβ chain of a T-cell receptor (TCR) of a WT1-specific cytotoxic T-cell (CTL), wherein said peptide has any of the amino acid sequences of CDR3 shown in SEQ ID Nos.: 757-1512;
(4) The peptide according to (3) consisting of any of the amino acid sequences of CDR3 shown in SEQ ID Nos.: 757-1512;
(5) Use of the polynucleotide of (1) or (2), or the peptide of (3) or (4) as a cancer marker;
(6) A method for diagnosing cancer in an HLA-A*0201-positive patient, which comprises assessing the clonality of a WT1-specific CTL having any of the polynucleotides of (1) or (2), or any of the peptides of (3) or (4) in a sample obtained from the patient before therapy, wherein in case that a WT1-specific CTL having a multiplicity of clonality is present, a higher possibility of developing cancer in the patient before therapy is determined when the types of a WT1-specific CTL with a multiplicity of clonality are more abundant, or when the clonality of a WT1-specific CTL with a multiplicity of clonality is higher;
(7) The method according to (6), wherein a higher possibility of developing cancer in the patient before therapy is determined when the clonality of a WT1-specific CTL having any of the CDR3 polynucleotides or any of the CDR3 peptides and having the clonality of 3 or more is higher, or when the types of a WT1-specific CTL having the clonality of 3 or more are more abundant;
(8) A method for testing for sensitivity of an HLA-A*0201-positive patient to WT1 peptide immunotherapy, which comprises assessing the number of types and the clonality of WT1-specific CTLs having any of the polynucleotides of (1) or (2) or any of the peptides of (3) or (4) in a sample obtained from the patient before therapy, wherein the patient is determined to have sensitivity to WT1 peptide immunotherapy when the types of WT1-specific CTLs with a multiplicity of clonality are more abundant in the patient than in a subject non-responsive to the immunotherapy;

(9) The method according to (8), wherein a patient is determined to have higher sensitivity to WT1 peptide immunotherapy when the types of WT1-specific CTL clones with a multiplicity of clonality are more abundant, or the clonality is larger in the patient before therapy;

(10) A method for monitoring WT1 peptide immunotherapy in an HLA-A*2402-positive patient, which comprises assessing the clonality of WT1-specific CTL clones having any of the polynucleotides of (1) or (2) or any of the peptides of (3) or (4) in a sample obtained from the patient before and after the immunotherapy, wherein the patient is determined to have responded to WT1 peptide immunotherapy when the clonality of any of the WT1-specific CTL clones increases after the immunotherapy compared to before the immunotherapy;

(11) The method according to (10), wherein a patient is determined to have higher responsiveness to WT1 peptide immunotherapy when the larger becomes the increase rate in the clonality, or the more abundant become the types of clones with increased clonality after the WT1 peptide immunotherapy;

(12) An antibody against the peptide of (3) or (4);

(13) A chip comprising the polynucleotide of (1) or (2), the peptide of (3) or (4), or the antibody of (12);

(14) A primer for amplifying a CDR3 polypeptide, which has a sequence selected from the sequences shown in SEQ ID Nos.: 1513-1538;

(15) A kit for diagnosing cancer, a kit for testing for sensitivity of a patient to WT1 peptide immunotherapy, or a kit for monitoring WT1 peptide immunotherapy, comprising means for detecting a WT1-specific CTL having the polynucleotide of (1) or (2) or the peptide of (3) or (4);

(16) A device for cancer diagnosis, a device for testing for sensitivity of a patient to WT1 peptide immunotherapy, or a device for monitoring WT1 peptide immunotherapy, comprising means for detecting a WT1-specific CTL having the polynucleotide of (1) or (2) or the peptide of (3) or (4);

(17) The kit according to (15), comprising the chip of (13) or the primer of (14);

(18) The device according to (16), wherein the chip of (13) or the primer of (14) is used in the device;

(19) A lymphocyte of an HLA-A*0201-positive cancer patient, into which a T-cell receptor gene comprising a sequence of the polynucleotide of (1) or (2) is introduced.

The present invention also provides cancer therapy using lymphocytes from HLA-A*0201-positive patients, wherein a T-cell receptor gene containing a CDR3 polynucleotide is introduced into the lymphocytes.

Further, the present invention provides an antibody raised against a CDR3 polypeptide and use thereof.

Effect of the Invention

By virtue of the present invention, the nucleotide sequences contained in the gene for the Vβ chain of T-cell receptors (TCRs) of WT1-specific cytotoxic T-cells (CTLs), and the amino acid sequences of peptides encoded by them, in particular, the nucleotide and amino acid sequences of CDR3 have been revealed, and extensive cancer tests (diagnosis, prognosis, treatment monitoring, or the like), effective cancer therapies, and the like are enabled using these polynucleotides and peptides.

BRIEF DESCRIPTION OF DRAWINGS

FIG. 1A shows the nucleotide and amino acid sequences of CDR3 of the Vβ chain of T-cell receptors (TCRs), the number of clone (clonality) thereof and the like of WT1-specific cytotoxic T-cells (CTLs) from healthy individuals and HLA-A*0201-positive solid cancer patients, which sequences have been identified in the present invention (DNA disclosed as SEQ ID NOS: 1-68 and peptides disclosed as SEQ ID NOS: 757-824, respectively, in order of appearance). In the figure, "clone #" indicates the clone numbers, the numbers to the left of the dot indicate the family numbers of Vβ chains, and the numbers to the right of the dot indicate the reference numbers. The column "name" indicates the subjects from which the clone derived, HD1, HD2, HD3, HD4, and HD5 indicate healthy individuals, respectively, and PT1, PT2, PT3, PT4, PT5 and PT6 indicate solid cancer patients and indicate the patients with glioblastoma, primitive neuroectodermal tumor, glioblastoma, ovarian cancer, cecal cancer, and glioblastoma, respectively. V name, J name, and D name indicate the details of the V region, J region, and D region, respectively. The nucleotide sequences are indicated by portion which derives from V region, N1 region, D region, (P)N2 region, or J region. The column to the right of the nucleotide sequence indicates what kind of region the sequence which constitutes the nucleotide sequence was derived from. The amino acid sequence encoded by each nucleotide sequence is indicated by 1 letter code known to those skilled in the art. Two columns to the right of the amino acid sequence indicate clonality in each healthy individual and clonality in each cancer patient. The rightmost column indicates the total of clonality of each clone.

FIG. 1B shows the nucleotide and amino acid sequences of CDR3 of the Vβ chain of T-cell receptors (TCRs), the number of clone (clonality) thereof and the like of WT1-specific cytotoxic T-cells (CTLs) from healthy individuals and HLA-A*0201-positive solid cancer patients, which sequences have been identified in the present invention (DNA disclosed as SEQ ID NOS: 69-141 and peptides disclosed as SEQ ID NOS: 825-897, respectively, in order of appearance). In the figure, "clone #" indicates the clone numbers, the numbers to the left of the dot indicate the family numbers of Vβ chains, and the numbers to the right of the dot indicate the reference numbers. The column "name" indicates the subjects from which the clone derived, HD1, HD2, HD3, HD4, and HD5 indicate healthy individuals, respectively, and PT1, PT2, PT3, PT4, PT5 and PT6 indicate solid cancer patients and indicate the patients with glioblastoma, primitive neuroectodermal tumor, glioblastoma, ovarian cancer, cecal cancer, and glioblastoma, respectively. V name, J name, and D name indicate the details of the V region, J region, and D region, respectively. The nucleotide sequences are indicated by portion which derives from V region, N1 region, D region, (P)N2 region, or J region. The column to the right of the nucleotide sequence indicates what kind of region the sequence which constitutes the nucleotide sequence was derived from. The amino acid sequence encoded by each nucleotide sequence is indicated by 1 letter code known to those skilled in the art. Two columns to the right of the amino acid sequence indicate clonality in each healthy individual and clonality in each cancer patient. The rightmost column indicates the total of clonality of each clone.

FIG. 1C shows the nucleotide and amino acid sequences of CDR3 of the Vβ chain of T-cell receptors (TCRs), the number of clone (clonality) thereof and the like of WT1-specific cytotoxic T-cells (CTLs) from healthy individuals and HLA-A*0201-positive solid cancer patients, which sequences have been identified in the present invention (DNA disclosed as SEQ ID NOS: 142-214 and peptides disclosed as SEQ ID NOS: 898-970, respectively, in order of appearance). In the figure, "clone #" indicates the clone numbers, the numbers to the left of the dot indicate the family numbers of Vβ chains, and the numbers to the right of the dot indicate the reference numbers. The column "name" indicates the subjects from which the clone derived, HD1, HD2, HD3, HD4, and HD5 indicate healthy individuals, respectively, and PT1, PT2, PT3, PT4, PT5 and PT6 indicate solid cancer patients and indicate the patients with glioblastoma, primitive neuroectodermal tumor, glioblastoma, ovarian cancer, cecal cancer, and glioblastoma, respectively. V name, J name, and D name indicate the details of the V region, J region, and D region, respectively. The nucleotide sequences are indicated by portion which derives from V region, N1 region, D region, (P)N2 region, or J region. The column to the right of the nucleotide sequence indicates what kind of region the sequence which constitutes the nucleotide sequence was derived from. The amino acid sequence encoded by each nucleotide sequence is indicated by 1 letter code known to those skilled in the art. Two columns to the right of the amino acid sequence indicate clonality in each healthy individual and clonality in each cancer patient. The rightmost column indicates the total of clonality of each clone.

FIG. 1D shows the nucleotide and amino acid sequences of CDR3 of the Vβ chain of T-cell receptors (TCRs), the number of clone (clonality) thereof and the like of WT1-specific cytotoxic T-cells (CTLs) from healthy individuals and HLA-A*0201-positive solid cancer patients, which sequences have been identified in the present invention (DNA disclosed as SEQ ID NOS: 215-287 and peptides disclosed as SEQ ID NOS: 971-1043, respectively, in order of appearance). In the figure, "clone #" indicates the clone numbers, the numbers to the left of the dot indicate the family numbers of Vβ chains, and the numbers to the right of the dot indicate the reference numbers. The column "name" indicates the subjects from which the clone derived, HD1, HD2, HD3, HD4, and HD5 indicate healthy individuals, respectively, and PT1, PT2, PT3, PT4, PT5 and PT6 indicate solid cancer patients and indicate the patients with glioblastoma, primitive neuroectodermal tumor, glioblastoma, ovarian cancer, cecal cancer, and glioblastoma, respectively. V name, J name, and D name indicate the details of the V region, J region, and D region, respectively. The nucleotide sequences are indicated by portion which derives from V region, N1 region, D region, (P)N2 region, or J region. The column to the right of the nucleotide sequence indicates what kind of region the sequence which constitutes the nucleotide sequence was derived from. The amino acid sequence encoded by each nucleotide sequence is indicated by 1 letter code known to those skilled in the art. Two columns to the right of the amino acid sequence indicate clonality in each healthy individual and clonality in each cancer patient. The rightmost column indicates the total of clonality of each clone.

FIG. 1E shows the nucleotide and amino acid sequences of CDR3 of the Vβ chain of T-cell receptors (TCRs), the number of clone (clonality) thereof and the like of WT1-specific cytotoxic T-cells (CTLs) from healthy individuals and HLA-A*0201-positive solid cancer patients, which sequences have been identified in the present invention (DNA disclosed as SEQ ID NOS: 288-360 and peptides disclosed as SEQ ID NOS: 1044-1116, respectively, in order of appearance). In the figure, "clone #" indicates the clone numbers, the numbers to the left of the dot indicate the family numbers of Vβ chains, and the numbers to the right of the dot indicate the reference numbers. The column "name" indicates the subjects from which the clone derived, HD1, HD2, HD3, HD4, and HD5 indicate healthy individuals, respectively, and PT1, PT2, PT3, PT4, PT5 and PT6 indicate solid cancer patients and indicate the patients with glioblastoma, primitive neuroectodermal tumor, glioblastoma, ovarian cancer, cecal cancer, and glioblastoma, respectively. V name, J name, and D name indicate the details of the V region, J region, and D region, respectively. The nucleotide sequences are indicated by portion which derives from V region, N1 region, D region, (P)N2 region, or J region. The column to the right of the nucleotide sequence indicates what kind of region the sequence which constitutes the nucleotide sequence was derived from. The amino acid sequence encoded by each nucleotide sequence is indicated by 1 letter code known to those skilled in the art. Two columns to the right of the amino acid sequence indicate clonality in each healthy individual and clonality in each cancer patient. The rightmost column indicates the total of clonality of each clone.

FIG. 1F shows the nucleotide and amino acid sequences of CDR3 of the Vβ chain of T-cell receptors (TCRs), the number of clone (clonality) thereof and the like of WT1-specific cytotoxic T-cells (CTLs) from healthy individuals and HLA-A*0201-positive solid cancer patients, which sequences have been identified in the present invention (DNA disclosed as SEQ ID NOS: 361-433 and peptides disclosed as SEQ ID NOS: 1117-1189, respectively, in order of appearance). In the figure, "clone #" indicates the clone numbers, the numbers to the left of the dot indicate the family numbers of Vβ chains, and the numbers to the right of the dot indicate the reference numbers. The column "name" indicates the subjects from which the clone derived, HD1, HD2, HD3, HD4, and HD5 indicate healthy individuals, respectively, and PT1, PT2, PT3, PT4, PT5 and PT6 indicate solid cancer patients and indicate the patients with glioblastoma, primitive neuroectodermal tumor, glioblastoma, ovarian cancer, cecal cancer, and glioblastoma, respectively. V name, J name, and D name indicate the details of the V region, J region, and D region, respectively. The nucleotide sequences are indicated by portion which derives from V region, N1 region, D region, (P)N2 region, or J region. The column to the right of the nucleotide sequence indicates what kind of region the sequence which constitutes the nucleotide sequence was derived from. The amino acid sequence encoded by each nucleotide sequence is indicated by 1 letter code known to those skilled in the art. Two columns to the right of the amino acid sequence indicate clonality in each healthy individual and clonality in each cancer patient. The rightmost column indicates the total of clonality of each clone.

FIG. 1G shows the nucleotide and amino acid sequences of CDR3 of the Vβ chain of T-cell receptors (TCRs), the number of clone (clonality) thereof and the like of WT1-specific cytotoxic T-cells (CTLs) from healthy individuals and HLA-A*0201-positive solid cancer patients, which sequences have been identified in the present invention (DNA disclosed as SEQ ID NOS 434-506: and peptides disclosed as SEQ ID NOS: 1190-1262, respectively, in order of appearance). In the figure, "clone #" indicates the clone numbers, the numbers to the left of the dot indicate the family numbers of Vβ chains, and the numbers to the right of the dot indicate the reference numbers. The column "name" indicates the subjects from which the clone derived, HD1, HD2, HD3, HD4, and HD5 indicate healthy individuals, respectively, and PT1, PT2, PT3, PT4, PT5 and PT6 indicate solid cancer patients and indicate the patients with glioblastoma, primitive neuroectodermal tumor, glioblastoma, ovarian cancer, cecal cancer, and glioblastoma, respectively. V name, J name, and D name indicate the details of the V region, J region, and D region, respectively. The nucleotide sequences are indicated by portion which derives from V region, N1 region, D region, (P)N2 region, or J region. The column to the right of the nucleotide sequence indicates what kind of region the sequence which constitutes the nucleotide sequence was derived from. The amino acid sequence encoded by each nucleotide sequence is indicated by 1 letter code known to those skilled in the art. Two columns to the right of the amino acid sequence indicate clonality in each healthy individual and clonality in each cancer patient. The rightmost column indicates the total of clonality of each clone.

FIG. 1H shows the nucleotide and amino acid sequences of CDR3 of the Vβ chain of T-cell receptors (TCRs), the number of clone (clonality) thereof and the like of WT1-specific cytotoxic T-cells (CTLs) from healthy individuals and HLA-A*0201-positive solid cancer patients, which sequences have been identified in the present invention (DNA disclosed as SEQ ID NOS: 507-579 and peptides disclosed as SEQ ID NOS: 1263-1335, respectively, in order of appearance). In the figure, "clone #" indicates the clone numbers, the numbers to the left of the dot indicate the family numbers of Vβ chains, and the numbers to the right of the dot indicate the reference numbers. The column "name" indicates the subjects from which the clone derived, HD1, HD2, HD3, HD4, and HD5 indicate healthy individuals, respectively, and PT1, PT2, PT3, PT4, PT5 and PT6 indicate solid cancer patients and indicate the patients with glioblastoma, primitive neuroectodermal tumor, glioblastoma, ovarian cancer, cecal cancer, and glioblastoma, respectively. V name, J name, and D name indicate the details of the V region, J region, and D region, respectively. The nucleotide sequences are indicated by portion which derives from V region, N1 region, D region, (P)N2 region, or J region. The column to the right of the nucleotide sequence indicates what kind of region the sequence which constitutes the nucleotide sequence was derived from. The amino acid sequence encoded by each nucleotide sequence is indicated by 1 letter code known to those skilled in the art. Two columns to the right of the amino acid sequence indicate clonality in each healthy individual and clonality in each cancer patient. The rightmost column indicates the total of clonality of each clone.

FIG. 1I shows the nucleotide and amino acid sequences of CDR3 of the Vβ chain of T-cell receptors (TCRs), the number of clone (clonality) thereof and the like of WT1-specific cytotoxic T-cells (CTLs) from healthy individuals and HLA-A*0201-positive solid cancer patients, which sequences have been identified in the present invention (DNA disclosed as SEQ ID NOS: 580-636 and peptides disclosed as SEQ ID NOS: 1336-1392, respectively, in order of appearance). In the figure, "clone #" indicates the clone numbers, the numbers to the left of the dot indicate the family numbers of Vβ chains, and the numbers to the right of the dot indicate the reference numbers. The column "name" indicates the subjects from which the clone derived, HD1, HD2, HD3, HD4, and HD5 indicate healthy individuals, respectively, and PT1, PT2, PT3, PT4, PT5 and PT6 indicate solid cancer patients and indicate the patients with glioblastoma, primitive neuroectodermal tumor, glioblastoma, ovarian cancer, cecal cancer, and glioblastoma, respectively. V name, J name, and D name indicate the details of the V region, J region, and D region, respectively. The nucleotide sequences are indicated by portion which derives from V region, N1 region, D region, (P)N2 region, or J region. The column to the right of the nucleotide sequence indicates what kind of region the sequence which constitutes the nucleotide sequence was derived from. The amino acid sequence encoded by each nucleotide sequence is indicated by 1 letter code known to those skilled in the art. Two columns to the right of the amino acid sequence indicate clonality in each healthy individual and clonality in each cancer patient. The rightmost column indicates the total of clonality of each clone.

FIG. 2A summarizes the nucleotide and amino acid sequences of CDR3 of the Vβ chain of T-cell receptors (TCRs) of the WT1-specific cytotoxic T-cells (CTLs) obtained from healthy individuals and HLA-A*0201-positive solid cancer patients (DNA disclosed as SEQ ID NOS: 1545-1601 and peptides disclosed as SEQ ID NOS: 2295-2351, respectively, in order of appearance). In the figure, the leftmost column "name" indicates a healthy individual or a cancer patient and the meaning of each symbol is the same as that of FIG. 1A. "Cell #" indicates the numbers of cells obtained from each individual. TRBV, TRBJ and TRBD have the same meaning as that of V name, J name, and D name of FIG. 1A, respectively. In the indication of the nucleotide sequence, the dots are omitted (which are not omitted in FIG. 1A). "*" or "**" to the right of the amino acid sequence indicates that two or more of the same sequences are arranged.

FIG. 2B summarizes the nucleotide and amino acid sequences of CDR3 of the Vβ chain of T-cell receptors (TCRs) of the WT1-specific cytotoxic T-cells (CTLs) obtained from healthy individuals and HLA-A*0201-positive solid cancer patients (DNA disclosed as SEQ ID NOS: 1602-1659 and peptides disclosed as SEQ ID NOS: 2352-2409, respectively, in order of appearance). In the figure, the leftmost column "name" indicates a healthy individual or a cancer patient and the meaning of each symbol is the same as that of FIG. 1A. "Cell #" indicates the numbers of cells obtained from each individual. TRBV, TRBJ and TRBD have the same meaning as that of V name, J name, and D name of FIG. 1A, respectively. In the indication of the nucleotide sequence, the dots are omitted (which are not omitted in FIG. 1A). "*" or "**" to the right of the amino acid sequence indicates that two or more of the same sequences are arranged.

FIG. 2C summarizes the nucleotide and amino acid sequences of CDR3 of the Vβ chain of T-cell receptors (TCRs) of the WT1-specific cytotoxic T-cells (CTLs) obtained from healthy individuals and HLA-A*0201-positive solid cancer patients (DNA disclosed as SEQ ID NOS: 1660-1717 and peptides disclosed as SEQ ID NOS: 2410-2467, respectively, in order of appearance). In the figure, the leftmost column "name" indicates a healthy individual or a cancer patient and the meaning of each symbol is the same as that of FIG. 1A. "Cell #" indicates the numbers of cells obtained from each individual. TRBV, TRBJ and TRBD have the same meaning as that of V name, J name, and D name of FIG. 1A, respectively. In the indication of the nucleotide sequence, the dots are omitted (which are not omitted in FIG. 1A). "*" or "**" to the right of the amino acid sequence indicates that two or more of the same sequences are arranged.

FIG. 2D summarizes the nucleotide and amino acid sequences of CDR3 of the Vβ chain of T-cell receptors (TCRs) of the WT1-specific cytotoxic T-cells (CTLs) obtained from healthy individuals and HLA-A*0201-positive solid cancer patients (DNA disclosed as SEQ ID NOS: 1718-1775 and peptides disclosed as SEQ ID NOS: 2468-2525, respectively, in order of appearance). In the figure, the leftmost column "name" indicates a healthy individual or a cancer patient and the meaning of each symbol is the same as that of FIG. 1A. "Cell #" indicates the numbers of cells obtained from each individual. TRBV, TRBJ and TRBD have the same meaning as that of V name, J name, and D name of FIG. 1A, respectively. In the indication of the nucleotide sequence, the dots are omitted (which are not omitted in FIG. 1A). "*" or "**" to the right of the amino acid sequence indicates that two or more of the same sequences are arranged.

FIG. 2E summarizes the nucleotide and amino acid sequences of CDR3 of the Vβ chain of T-cell receptors (TCRs) of the WT1-specific cytotoxic T-cells (CTLs) obtained from healthy individuals and HLA-A*0201-positive solid cancer patients (DNA disclosed as SEQ ID NOS: 1776-1833 and peptides disclosed as SEQ ID NOS: 2526-2583, respectively, in order of appearance). In the figure, the leftmost column "name" indicates a healthy individual or a cancer patient and the meaning of each symbol is the same as that of FIG. 1A. "Cell #" indicates the numbers of cells obtained from each individual. TRBV, TRBJ and TRBD have the same meaning as that of V name, J name, and D name of FIG. 1A, respectively. In the indication of the nucleotide sequence, the dots are omitted (which are not omitted in FIG. 1A). "*" or "**" to the right of the amino acid sequence indicates that two or more of the same sequences are arranged.

FIG. 2F summarizes the nucleotide and amino acid sequences of CDR3 of the Vβ chain of T-cell receptors (TCRs) of the WT1-specific cytotoxic T-cells (CTLs) obtained from healthy individuals and HLA-A*0201-positive solid cancer patients (DNA disclosed as SEQ ID NOS: 1834-1891 and peptides disclosed as SEQ ID NOS: 2584-2641, respectively, in order of appearance). In the figure, the leftmost column "name" indicates a healthy individual or a cancer patient and the meaning of each symbol is the same as that of FIG. 1A. "Cell #" indicates the numbers of cells obtained from each individual. TRBV, TRBJ and TRBD have the same meaning as that of V name, J name, and D name of FIG. 1A, respectively. In the indication of the nucleotide sequence, the dots are omitted (which are not omitted in FIG. 1A). "*" or "**" to the right of the amino acid sequence indicates that two or more of the same sequences are arranged.

FIG. 2G summarizes the nucleotide and amino acid sequences of CDR3 of the Vβ chain of T-cell receptors (TCRs) of the WT1-specific cytotoxic T-cells (CTLs) obtained from healthy individuals and HLA-A*0201-positive solid cancer patients (DNA disclosed as SEQ ID NOS: 1892-1949 and peptides disclosed as SEQ ID NOS: 2642-2699, respectively, in order of appearance). In the figure, the leftmost column "name" indicates a healthy individual or a cancer patient and the meaning of each symbol is the same as that of FIG. 1A. "Cell #" indicates the numbers of cells obtained from each individual. TRBV, TRBJ and TRBD have the same meaning as that of V name, J name, and D name of FIG. 1A, respectively. In the indication of the nucleotide sequence, the dots are omitted (which are not omitted in FIG. 1A). "*" or "**" to the right of the amino acid sequence indicates that two or more of the same sequences are arranged.

FIG. 2H summarizes the nucleotide and amino acid sequences of CDR3 of the Vβ chain of T-cell receptors (TCRs) of the WT1-specific cytotoxic T-cells (CTLs) obtained from healthy individuals and HLA-A*0201-positive solid cancer patients (DNA disclosed as SEQ ID NOS: 1950-2007 and peptides disclosed as SEQ ID NOS: 2700-2757, respectively, in order of appearance). In the figure, the leftmost column "name" indicates a healthy individual or a cancer patient and the meaning of each symbol is the same as that of FIG. 1A. "Cell #" indicates the numbers of cells obtained from each individual. TRBV, TRBJ and TRBD have the same meaning as that of V name, J name, and D name of FIG. 1A, respectively. In the indication of the nucleotide sequence, the dots are omitted (which are not omitted in FIG. 1A). "*" or "**" to the right of the amino acid sequence indicates that two or more of the same sequences are arranged.

FIG. 2I summarizes the nucleotide and amino acid sequences of CDR3 of the Vβ chain of T-cell receptors (TCRs) of the WT1-specific cytotoxic T-cells (CTLs) obtained from healthy individuals and HLA-A*0201-positive solid cancer patients (DNA disclosed as SEQ ID NOS 2008-2065: and peptides disclosed as SEQ ID NOS: 2758-2815, respectively, in order of appearance). In the figure, the leftmost column "name" indicates a healthy individual or a cancer patient and the meaning of each symbol is the same as that of FIG. 1A. "Cell #" indicates the numbers of cells obtained from each individual. TRBV, TRBJ and TRBD have the same meaning as that of V name, J name, and D name of FIG. 1A, respectively. In the indication of the nucleotide sequence, the dots are omitted (which are not omitted in FIG. 1A). "*" or "**" to the right of the amino acid sequence indicates that two or more of the same sequences are arranged.

FIG. 2J summarizes the nucleotide and amino acid sequences of CDR3 of the Vβ chain of T-cell receptors (TCRs) of the WT1-specific cytotoxic T-cells (CTLs) obtained from healthy individuals and HLA-A*0201-positive solid cancer patients (DNA disclosed as SEQ ID NOS: 2066-2123 and peptides disclosed as SEQ ID NOS: 2816-2873, respectively, in order of appearance). In the figure, the leftmost column "name" indicates a healthy individual or a cancer patient and the meaning of each symbol is the same as that of FIG. 1A. "Cell #" indicates the numbers of cells obtained from each individual. TRBV, TRBJ and TRBD have the same meaning as that of V name, J name, and D name of FIG. 1A, respectively. In the indication of the nucleotide sequence, the dots are omitted (which are not omitted in FIG. 1A). "*" or "**" to the right of the amino acid sequence indicates that two or more of the same sequences are arranged.

FIG. 2K summarizes the nucleotide and amino acid sequences of CDR3 of the Vβ chain of T-cell receptors (TCRs) of the WT1-specific cytotoxic T-cells (CTLs) obtained from healthy individuals and HLA-A*0201-positive solid cancer patients (DNA disclosed as SEQ ID NOS: 2124-2181 and peptides disclosed as SEQ ID NOS: 2874-2931, respectively, in order of appearance). In the figure, the leftmost column "name" indicates a healthy individual or a cancer patient and the meaning of each symbol is the same as that of FIG. 1A. "Cell #" indicates the numbers of cells obtained from each individual. TRBV, TRBJ and TRBD have the same meaning as that of V name, J name, and D name of FIG. 1A, respectively. In the indication of the nucleotide sequence, the dots are omitted (which are not omitted in FIG. 1A). "*" or "**" to the right of the amino acid sequence indicates that two or more of the same sequences are arranged.

FIG. 2L summarizes the nucleotide and amino acid sequences of CDR3 of the Vβ chain of T-cell receptors (TCRs) of the WT1-specific cytotoxic T-cells (CTLs) obtained from healthy individuals and HLA-A*0201-positive solid cancer patients (DNA disclosed as SEQ ID NOS:

Figure 1A:
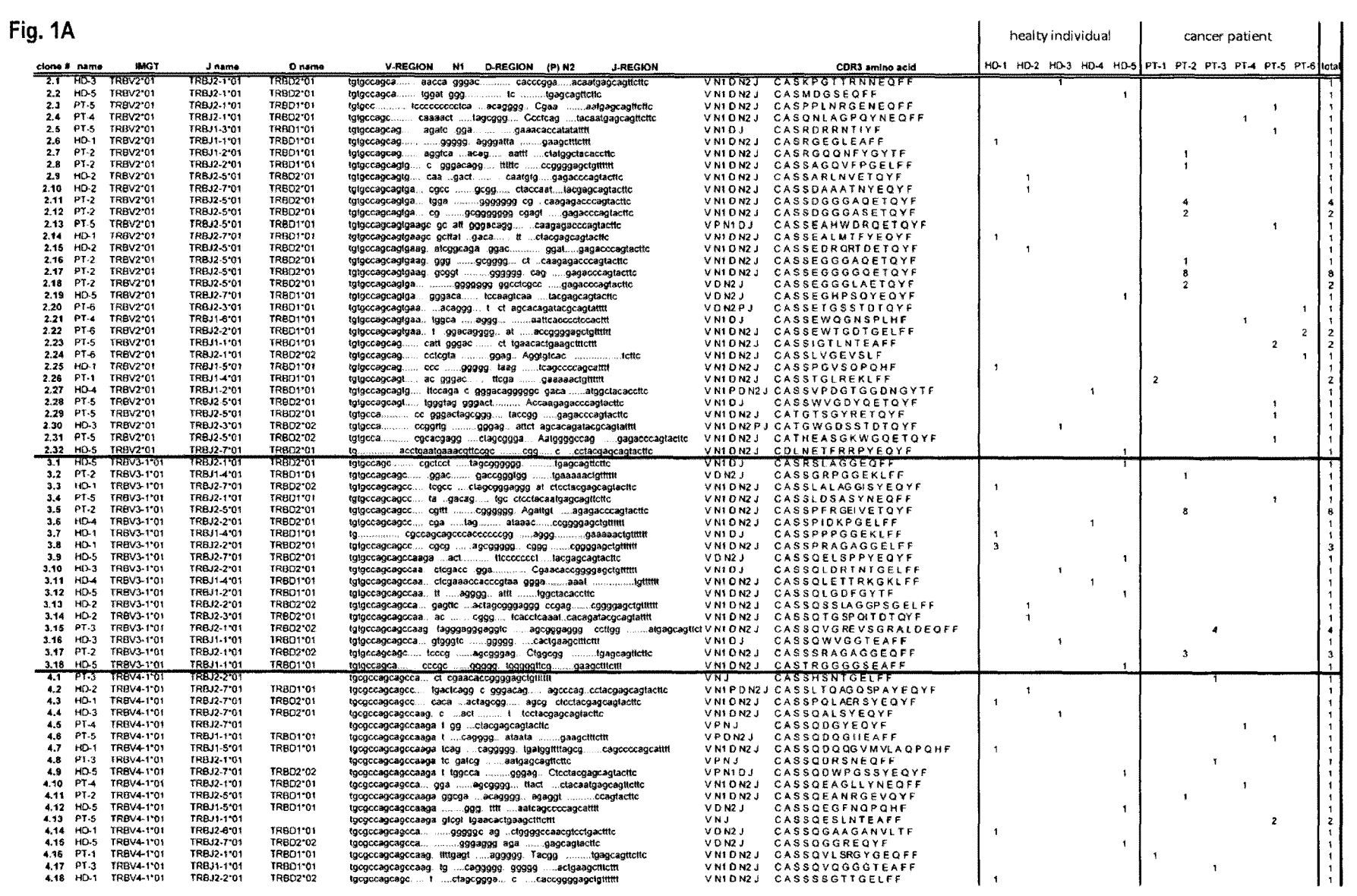
Figure 1B:
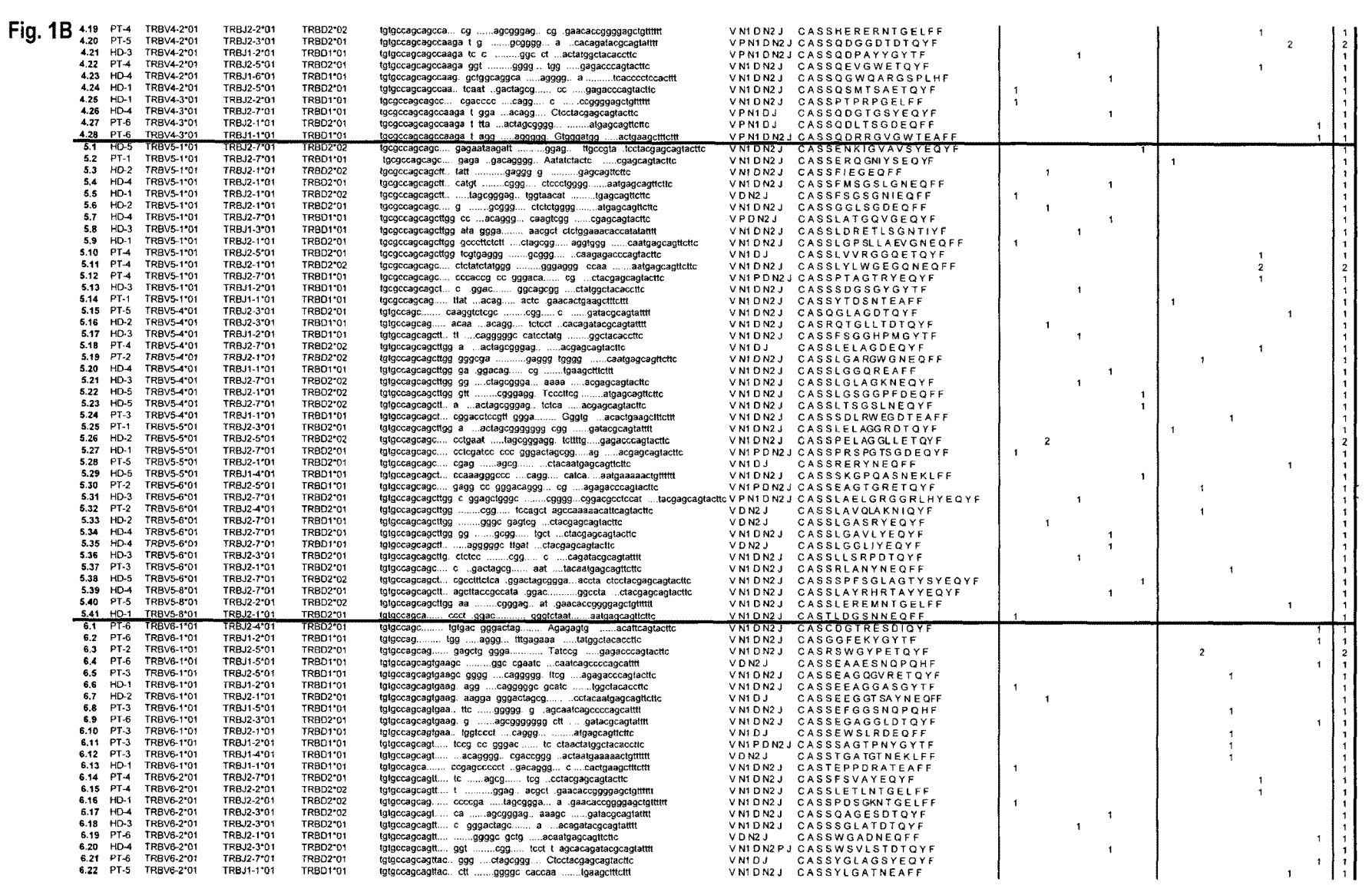
Figure 1C:
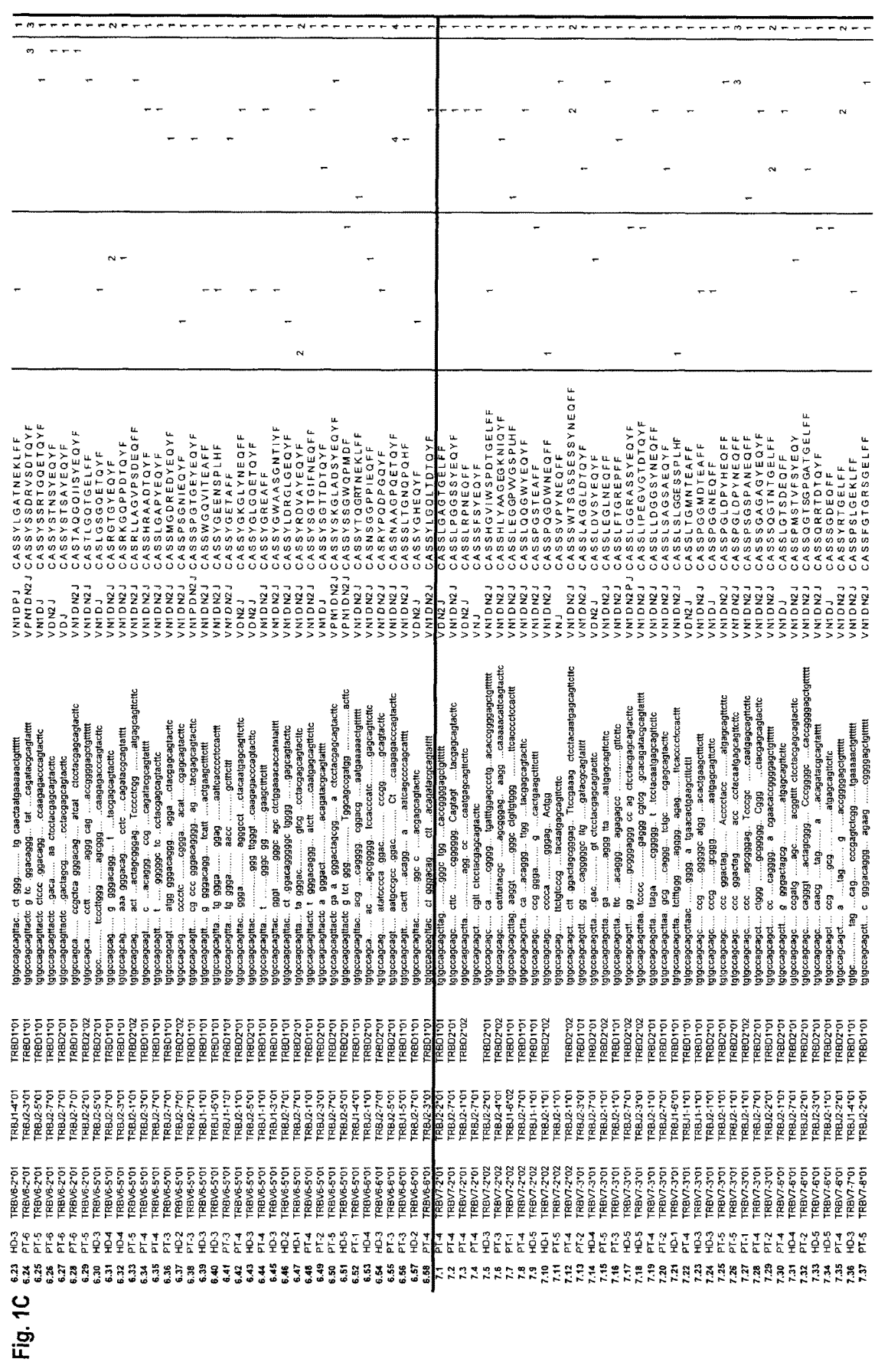
Figure 1D:
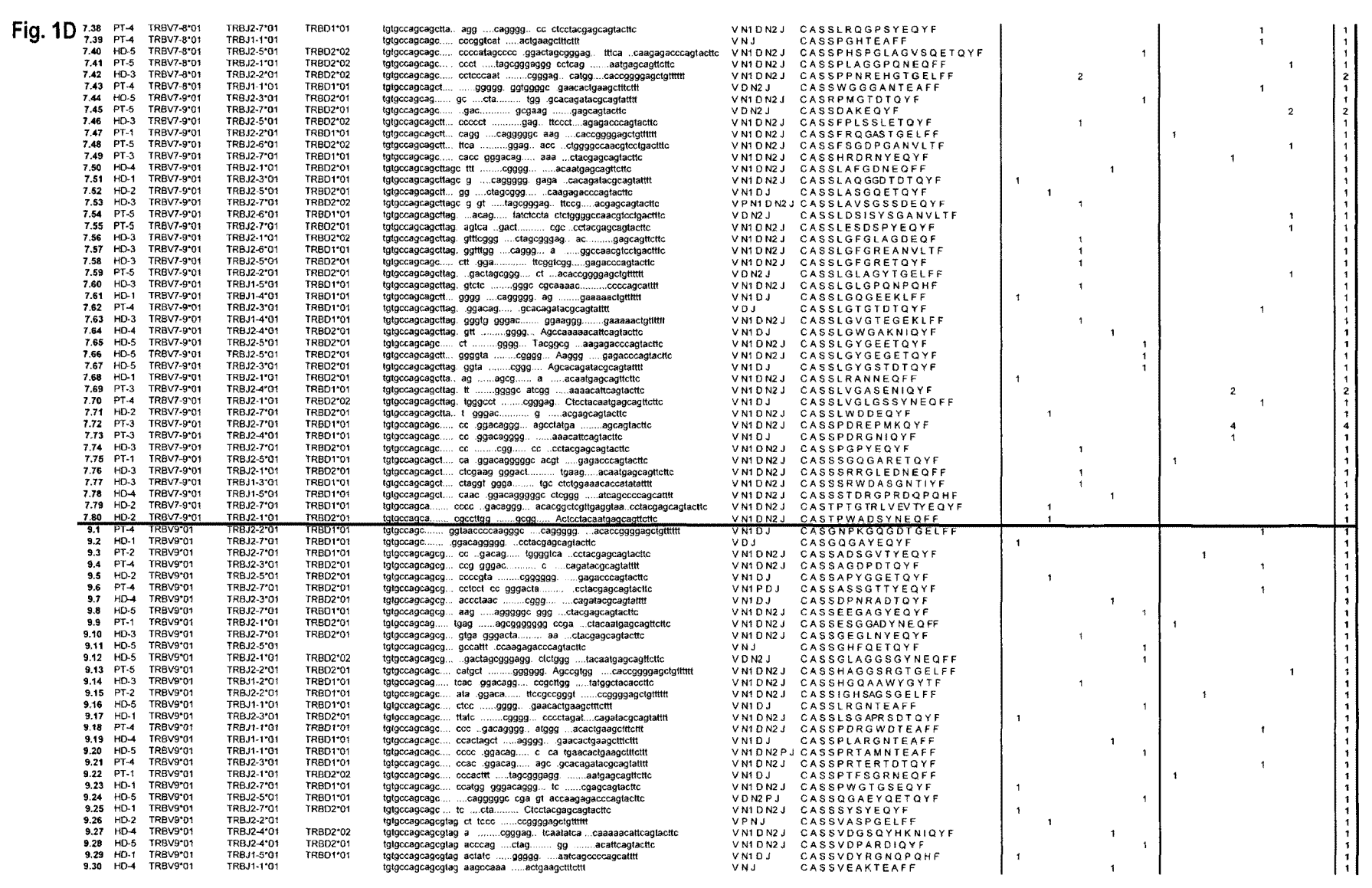
Figure 1E:
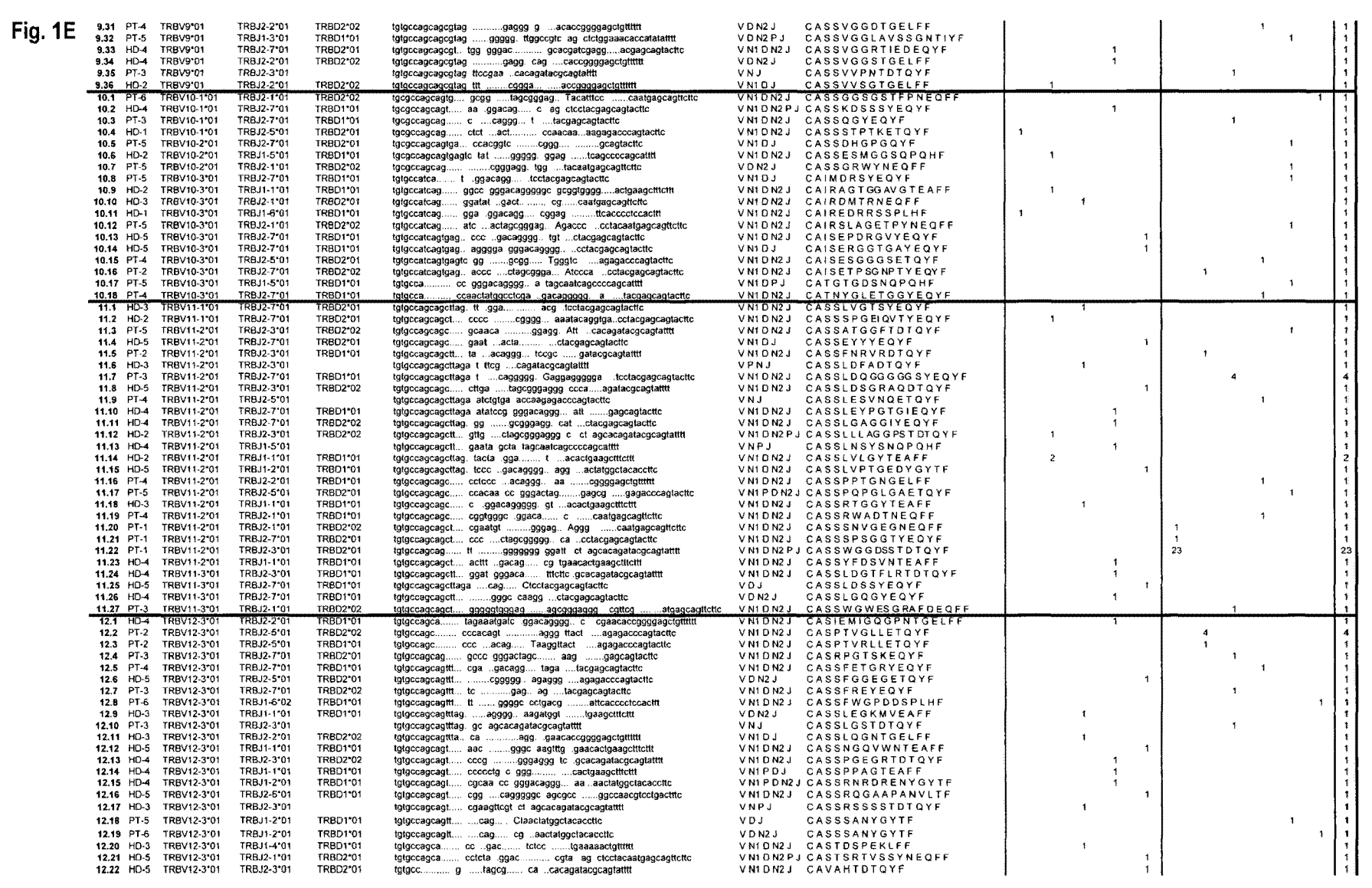
Figure 1F:
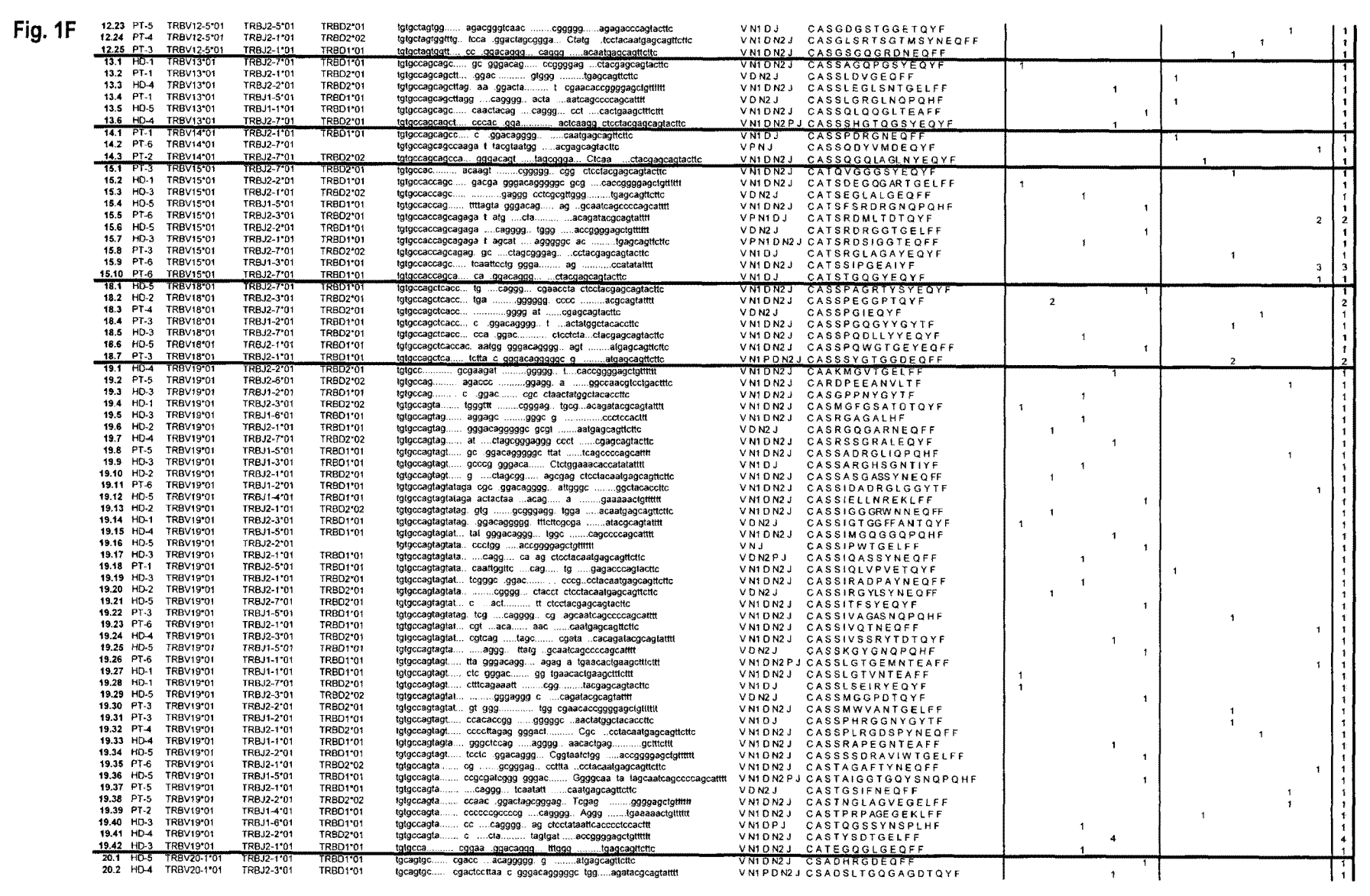
Figure 1G:
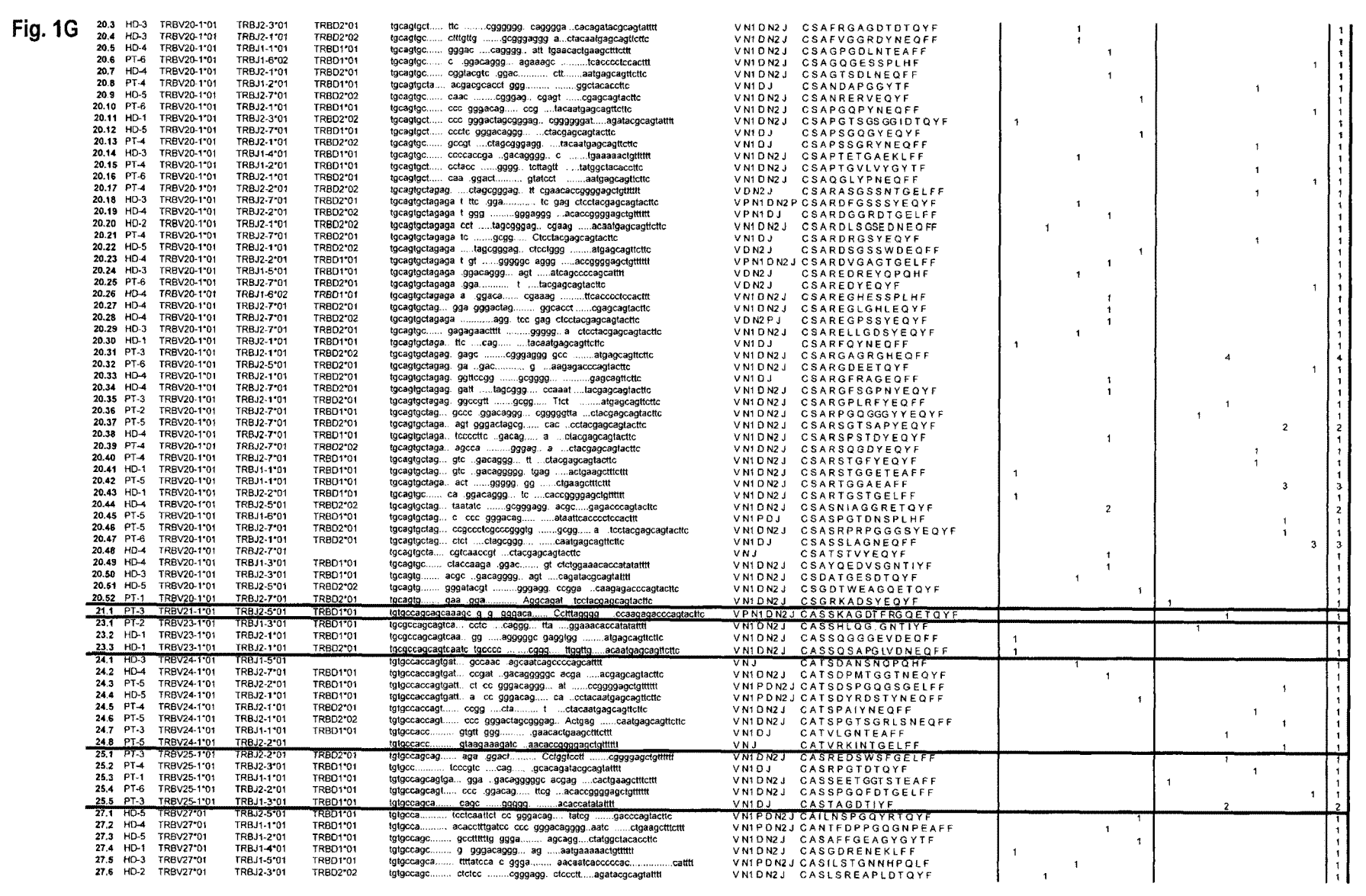
Figure 1H:
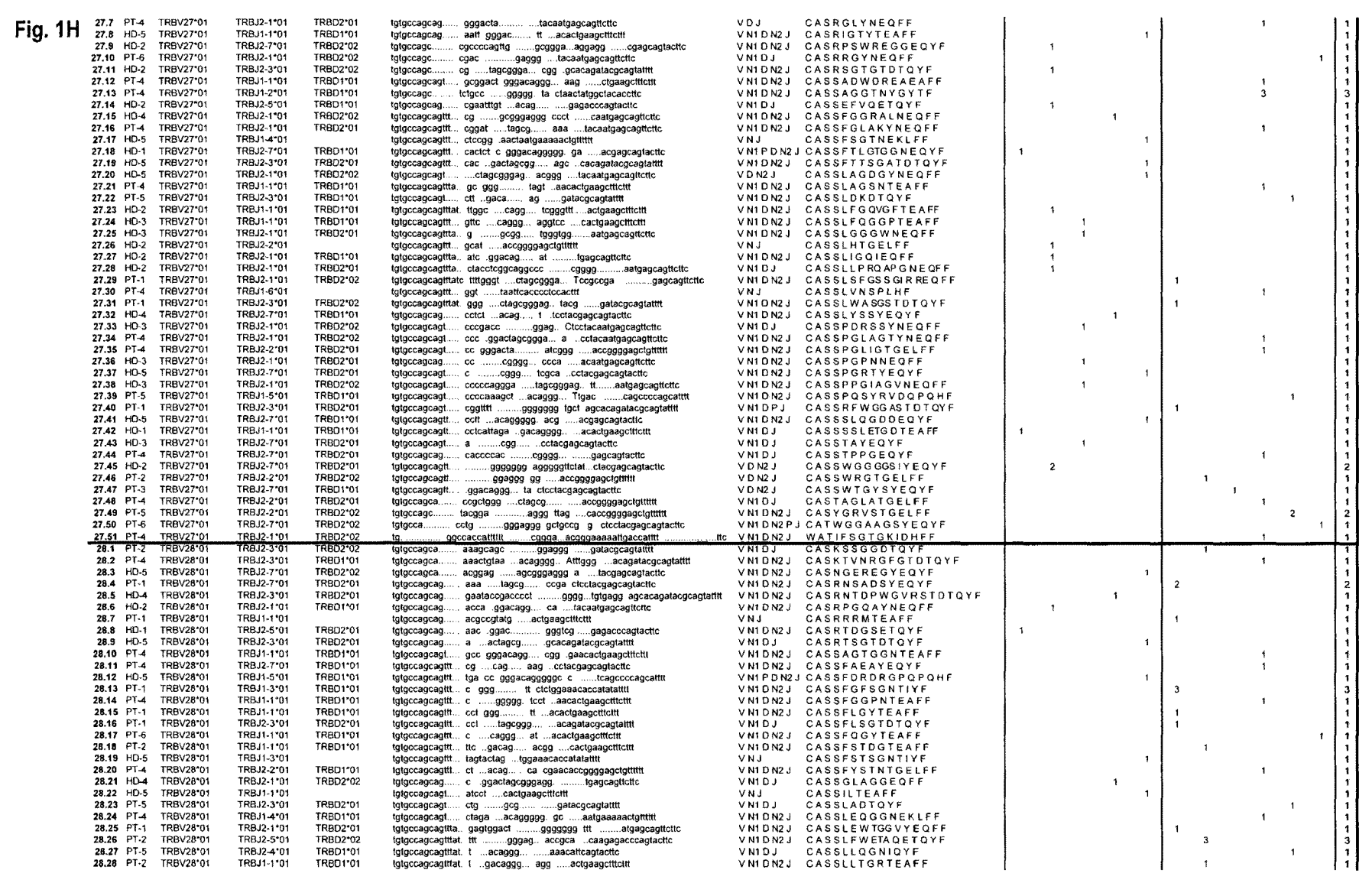

2182-2239 and peptides disclosed as SEQ ID NOS: 2932-2989, respectively, in order of appearance). In the figure, the leftmost column "name" indicates a healthy individual or a cancer patient and the meaning of each symbol is the same as that of FIG. 1A. "Cell #" indicates the numbers of cells obtained from each individual. TRBV, TRBJ and TRBD have the same meaning as that of V name, J name, and D name of FIG. 1A, respectively. In the indication of the nucleotide sequence, the dots are omitted (which are not omitted in FIG. 1A). "*" or "**" to the right of the amino acid sequence indicates that two or more of the same sequences are arranged.

Figure 2K:
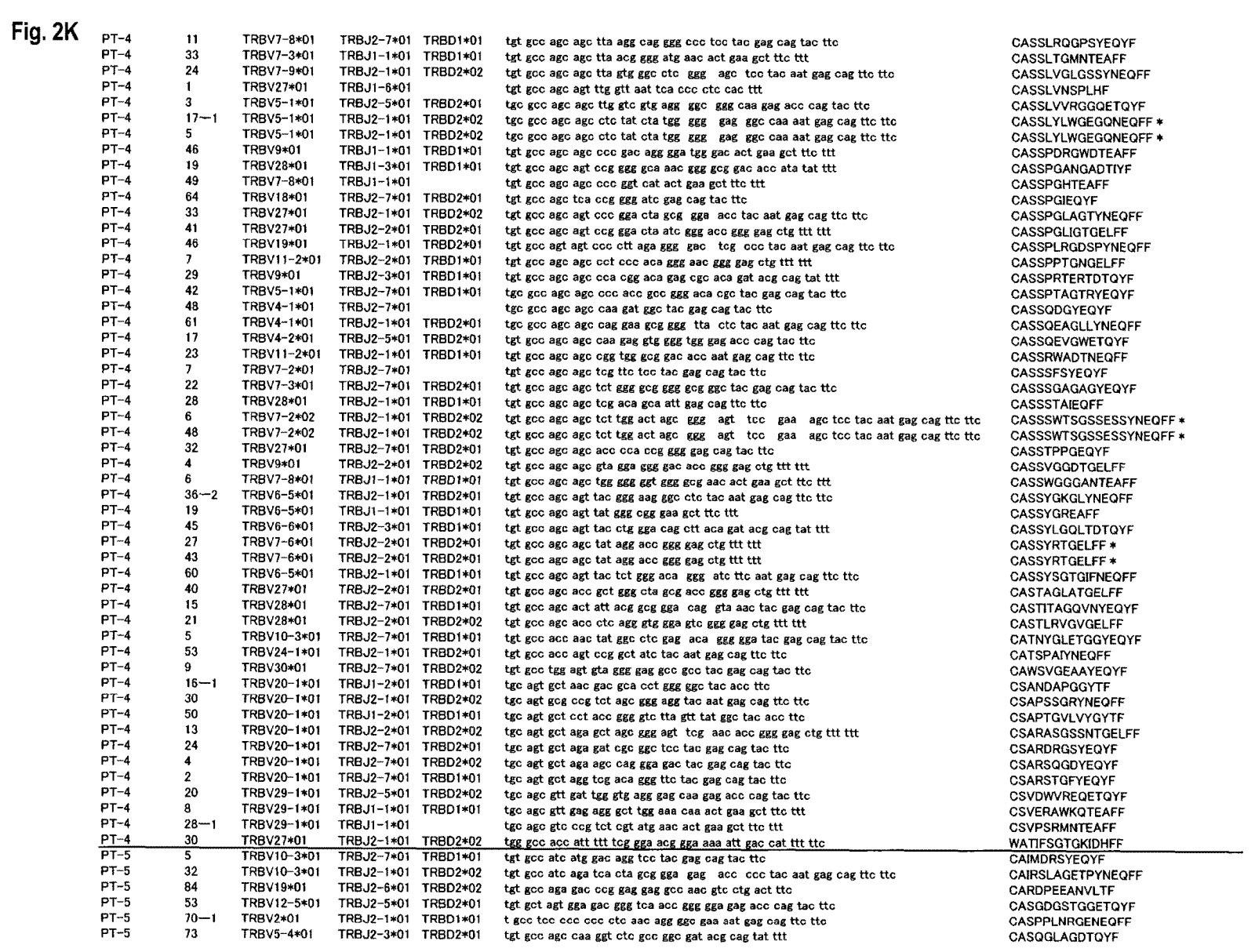

FIG. 2M summarizes the nucleotide and amino acid sequences of CDR3 of the Vβ chain of T-cell receptors (TCRs) of the WT1-specific cytotoxic T-cells (CTLs) obtained from healthy individuals and HLA-A*0201-positive solid cancer patients (DNA disclosed as SEQ ID NOS: 2240-2294 and peptides disclosed as SEQ ID NOS: 2990-3044, respectively, in order of appearance). In the figure, the leftmost column "name" indicates a healthy individual or a cancer patient and the meaning of each symbol is the same as that of FIG. 1A. "Cell #" indicates the numbers of cells obtained from each individual. TRBV, TRBJ and TRBD have the same meaning as that of V name, J name, and D name of FIG. 1A, respectively. In the indication of the nucleotide sequence, the dots are omitted (which are not omitted in FIG. 1A). "*" or "**" to the right of the amino acid sequence indicates that two or more of the same sequences are arranged.

MODE FOR CARRYING OUT THE INVENTION

The inventors have stained the peripheral lymphocytes from cancer patients with WT1 tetramer that consists of WT1 peptide/HLA-A*0201 complexes, and has separated WT1 tetramer-positive cells one by one using a FACS; cDNAs have been generated from each separated cell, and the nucleotide sequences encoding CDR3 contained in the Vβ chain of T-cell receptors (hereinafter may be referred to as "TCR") of WT1-specific cytotoxic T-cells, hereinafter may be referred to as "WT1-specific CTL", have been determined by applying PCR method (FIGS. 1-1 to 1-9 and FIGS. 2-1 to 2-13; SEQ ID Nos.: 1-756). From these results, the amino acid sequences of the CDR3 have been also determined (FIGS. 1-1 to 1-9 and FIGS. 2-1 to 2-13; SEQ ID Nos.: 757-1512). These sequences have been determined for the first time in the present invention.

Thus, in one aspect, the present invention provides a polynucleotide having the nucleotide sequence encoding CDR3 of the Vβ chain of T-cell receptors (TCRs) of WT1-specific cytotoxic T-cells (CTLs) obtained from healthy individuals and HLA-A*0201-positive patients, wherein the polynucleotide has DNA having any of the CDR3 nucleotide sequences shown in SEQ ID Nos.: 1-756, RNA complementary to the DNA, or a complementary sequence thereof. As used herein, these DNA and RNA molecules and the complementary polynucleotides thereof are collectively referred to as "CDR3 polynucleotides." For example, the CDR3 polynucleotides include, in addition to the DNAs comprising the nucleotide sequences shown in SEQ ID Nos.: 1-756, DNAs comprising these sequences. Also, for example, the CDR3 polynucleotides include, in addition to the RNAs complementary to the DNAs comprising the nucleotide sequences shown in SEQ ID Nos.: 1-756, RNAs comprising these sequences. Further, for example, the CDR3 polynucleotides include polynucleotides having the sequences of the DNAs or RNAs, and polynucleotides complementary to the RNAs. The "CDR polynucleotides" include those having degenerate sequences encoding "CDR3 peptides."

In another aspect, the present invention provides peptides having the amino acid sequences of CDR3 of the Vβ chain of T-cell receptors (TCRs) of WT1-specific cytotoxic T-cells (CTLs), which CDR3 amino acid sequences being shown in any of SEQ ID Nos.: 757-1512. As used herein, these peptides are collectively referred to as "CDR3 peptides." For example, the CDR3 peptides include, in addition to a peptide comprising any of the CDR3 amino acid sequences shown in SEQ ID Nos.: 757-1512, peptides comprising these CDR3 amino acid sequences (such as, for example, Vβ chain peptides or a portion thereof). In addition, a peptide consisting or comprising the amino acid sequence shown in SEQ ID Nos.: 757-1512 in which one or a few, preferably one to three, one or two, or one amino acid is substituted, added, or deleted is included in the "CDR3 peptides." However, these peptides are required to have equivalent functions to the original peptide. These CDR3 peptides are encoded by the above-mentioned CDR3 polynucleotides.

The CDR3 regions are the most diverse portions and are the most responsible parts for the specificity of antigen recognition. Thus, the sequences of the CDR3 polynucleotides and CDR3 peptides of the present invention are considered peculiar to WT1-specific CTL in HLA-A*0201-positive patients. Therefore, provided that the polynucleotide encoding the CDR3 region of the gene for the TCR Vβ chain of a certain T-cell or the peptide corresponding to the CDR3 region have the sequence of the polynucleotide or peptide of the present invention, the T-cell is considered as specific for WT1. Accordingly, the CDR3 polynucleotides and CDR3 peptides of the present invention may find use as markers for a wide variety of cancers, use in applications such as diagnosis of cancer, diagnosis of the susceptibility of patients to WT1 peptide immunotherapy, and tests for the responsiveness in the patients to WT1 peptide immunotherapy.

The CDR3 polynucleotides and CDR3 peptides of the present invention may be present in the lymphocytes of patients with any type of cancer as long as the cancer is generated from cells containing WT1. WT1 is known as a cancer antigen in a variety of cancers and hematological malignancies. Thus, the CDR3 polynucleotides and CDR3 peptides of the present invention, as well as the methods of the present invention described below, regardless of whether solid cancer or hematological cancer, may be applied to almost all the types of cancers including, but not limited to, for example, hematologic malignancies, such as acute myelocytic leukemia, acute lymphocytic leukemia, malignant lymphoma, multiple myeloma, chronic myelocytic leukemia, myelodysplastic syndrome, and recurrence after the transplantation of hematopoietic stem cells of the same type; solid cancers, such as tongue cancer, gingival cancer, mouth floor cancer, pharyngeal cancer, larynx cancer, salivary gland cancer, and thyroid cancer; thoracic cancers, such as breast cancer, lung cancer, and thymic cancer; gastrointestinal cancers, such as colon cancer, small intestine cancer, gastric cancer, pancreatic cancer, liver cancer, bile duct cancer, gastrointestinal endocrine tumor, and gastrointestinal carcinoid; cancers of urinary and genital tract, such as renal cancer, urothelial cancer, germinoma, Wilms' tumor, prostate cancer, uterine body cancer, cervical cancer, uterine sarcoma, and ovarian malignancy; musculoskeletal malignancies, such as primary malignancy of bone (e.g., osteosarcoma and Ewing's sarcoma) and soft tissue sarcoma; and other cancers, such as skin cancer, neuroblastoma, malignant glioma (glioblastoma), primary malignant lymphoma of the central nervous system, medulloblastoma, and PNET.

When producing CDR3 polynucleotides or CDR3 peptides, conventional genetic engineering techniques and/or chemical synthetic procedures may be used. For example, CDR3 polynucleotides may be isolated from cells or chemically synthesized. CDR3 polynucleotides may also be amplified using a known method, such as PCR. Also, for example, a CDR3 polynucleotide (optionally amplified to an appropriate level using a known method) may be integrated into a suitable vector and introduced into suitable cells, or may be introduced into suitable cells by biolistic bombardment or electroporation. Then the cells into which the CDR3 polynucleotide is introduced are cultured for expression, thereby obtaining the CDR3 polynucleotide or peptide. Available vectors and cells, conditions for gene transfer, culture conditions, and methods for isolating genes and peptides are known to those skilled in the art and appropriately selected for use. Chemical synthesis may be used to produce CDR3 polynucleotides or CDR3 peptides. Methods for such chemical synthesis are known, and the methods for chemical synthesis of genes include solid-phase DNA synthesis using amidite, and the 1-4 phosphonate method; the methods for chemical synthesis of peptides include the Fmoc method.

Thus, in a further aspect, the present invention provides a method for diagnosing cancer in an HLA-A*0201-positive patient, the method including assessing the clonality of WT1-specific CTL having any of the CDR3 polynucleotides or CDR3 peptides in a sample obtained from the patient before therapy, wherein in case that a WT1-specific CTL having a multiplicity of clonality is present, a higher possibility of developing cancer in the patient before therapy is determined when the types of a WT1-specific CTL with a multiplicity of clonality are more abundant, or when the clonality of a WT1-specific CTL with a multiplicity of clonality is higher. As used herein, the term "clonality" refers to the frequency of detection of cells having an identical nucleotide or amino acid sequence. To examine clonality, it is general to use a cell sorter that allows identification of individual cells. The "patients" include both humans suspected to have cancer and those suffering from cancer. When the method is performed, the types of a WT1-specific CTL with a multiplicity of clonality or the clonality of a WT1-specific CTL with a multiplicity of clonality may be compared with that of humans not suffering from cancer.

The inventors have found that it is possible to determine whether a patient develops cancer or not by examining the clonality of WT1-specific CTL having any of the CDR3 polynucleotides or CDR3 peptides in the patient. As can be seen from FIGS. 1-1 to 1-9 and 2-1 to 2-13, in the healthy individuals (HD1 to HD5), the clonality of WT1-specific CTL having any of the CDR3 polynucleotides or CDR3 peptides is 1 for almost all the clones, 2 or 3 for rare clones, and 4 for rarer clone (only 1 clone); however, by contrast, all the cancer patients before therapy (PT1 to PT6) have a multiplicity of clonality of the WT1-specific CTLs having any of the CDR3 polynucleotides or CDR3 peptides without exception. The number of the clonality is larger and the types of such cells are more abundant than those of the healthy individuals. The increases in clonality and in types of cells having a multiplicity of clonality in patients before therapy indicate a possibility that defense and attack against cancer cells has already been launched in the patients.

In view of these results, the possibility of cancer in a patient may be determined if a multiplicity of clonality is found in the WT1-specific CTL having any of the CDR3 polynucleotides or CDR3 peptides when examining a sample from a subject. Further, it is possible to determine that the larger the clonality of WT1-specific CTL having any of the CDR3 polynucleotides or CDR3 peptides, or the more abundant the types of WT1-specific CTLs having a multiplicity of clonality, the higher the possibility of developing cancer is in the subject before therapy. Also, in the determination method, it is possible to determine that the higher the possibility of developing cancer in the patient before therapy is when the clonality of WT1-specific CTL having any of the CDR3 polynucleotides or CDR3 peptides and having the clonality of 3 or more is larger, or the types of WT1-specific CTL having the clonality of 3 or more are more abundant.

In a further aspect, the present invention provides a method for testing for the sensitivity of an HLA-A*0201-positive patient to WT1 peptide immunotherapy, the method including assessing the clonality and the number of types of WT1-specific CTL clones having any of the polynucleotides of claim 1 or any of the peptides of claim in a sample obtained from the patient before therapy, wherein the patient is determined to have the sensitivity to WT1 peptide immunotherapy when the types of WT1-specific CTL clones with a multiplicity of clonality are more abundant in the patient than in non-responsive subjects.

WT1-specific CTLs having any of the CDR3 polynucleotides or CDR3 peptides act against cancer cells in the patients. In this process, the clones that already have a multiplicity of clonality before therapy are considered to further increase the clonality or maintain their clonality by WT1 peptide immunotherapy. It is also considered that WT1 immunotherapy is more likely to be successful when there are clones of as many types as possible, which gives increased number and types of effective WT1-specific CTL clones as a whole. More strictly speaking, the sensitivity of a patient to WT1 peptide immunotherapy may be determined as being high when the types of WT1-specific CTL clones with a multiplicity of clonality are more abundant in the patient than in non-responsive subjects.

An increase in the clonality of a certain clone indicates that the WT1 peptide immunotherapy showed its effect for a certain period of time. Even if the clonality of certain clones may increase temporarily and then decrease, the clonality of other WT1-specific CTLs would increase to complement the effect. Considering the effect on cancer cells, a larger increase in the clonality is more desired. Therefore, the larger becomes the increase in the clonality or the more abundant become the types of clones with increased clonality after the WT1 peptide immunotherapy, the responsiveness to the WT1 peptide immunotherapy is considered to have been high.

In a further aspect, the present invention provides a method for monitoring WT1 peptide immunotherapy in an HLA-A*0201-positive patient, the method including assessing the clonality of WT1-specific CTL clones having any of the polynucleotides of claim 1 or any of the peptides of claim 2 in a sample obtained from the patient before and after the therapy, wherein the patient is determined to have responded to WT1 peptide immunotherapy when the clonality of any of the WT1-specific CTL clones increases after the therapy compared to before the therapy.

The presence of clones that increases their clonality due to WT1 peptide immunotherapy indicates the responsiveness to the WT1 peptide immunotherapy. In other words, the increase in the clonality suggests that the WT1 peptide immunotherapy showed its effect for a certain period of time. These increases in clonality may be transient or sustained. If the clonality of certain clones may increase only temporarily and then decrease, the clonality of other WT1-specific CTLs would increase to complement the effect. Considering the effect on cancer cells, a larger increase in the clonality is more desired. Therefore, the larger becomes the increase in the clonality or the more abundant become the types of clones with increased clonality after the WT1 peptide immunotherapy, the patient may be determined to have higher responsiveness to the WT1 peptide immunotherapy. The number and properties of cancer cells may be examined using an appropriate method depending on the type and site of the cancer.

In the above-described method for monitoring therapy, although the clonality is compared before and after WT1 peptide immunotherapy, the time period between before and after the therapy may be of any length. For example, it may be a few days, one week, two, three, or four weeks, or two or three months or more.

In the methods of the present invention described above, the means and methods for assessing clonality and determining the types of clones (i.e., determining the amino acid sequences of CDR3 peptides or the nucleotide sequences encoding the same) are known in the art, and those skilled in the art may conveniently carry out these operations. For example, as shown in Examples in the specification, a known sorting apparatus, such as the FACSAria system, and a method for gene amplification, such as PCR (using, for example, a primer set selected from the sequences listed in Table 1), may be used. In order to analyze the CDR3 polynucleotides or CDR peptides of the present invention in a stricter or more definite manner, one has only to confirm whether the nucleotide sequences of CDR3 (international ImMunoGeneTics information system, IMGT®) and the J and D regions in the Vβ chain gene are shown in FIGS. 1-1 to 1-9 and 2-1 to 2-13. Such confirmation is well within the ordinary skill of the art.

WT1 peptide immunotherapy is also known. For example, it may be performed on HLA-A*0201-positive patients by administering HLA-A*0201-restricted WT1 peptide (for example, $WT1_{126}$: amino acid sequence: RMF-PNAPYL (SEQ ID No: 1543) or $WT1_{187}$: amino acid sequence: SLGEQQYSV (SEQ ID No: 1544)) via, for example, a transdermal route. In general, a single dose is in the order of μg/kg body weight to mg/kg body weight, and it may be administered at an interval of one week to a few weeks.

In a further aspect, the present invention provides a chip comprising the CDR3 polynucleotides or the polynucleotides complementary thereto; a chip comprising the CDR3 peptides; or a chip comprising antibodies against the CDR3 peptides. The chips may be in the form of microchips, microarrays, and the like. The production of the chips may be conducted according to conventional methods; for example, antibodies raised against the CDR3 polynucleotides or CDR3 peptides may be immobilized on a glass substrate. The species of the CDR3 polynucleotides or the polynucleotides complementary thereto, the CDR3 peptides, or the antibodies against the CDR3 peptides that is immobilized on the chip may be one to all; preferably, all the species are immobilized for exhaustive analysis. For example, all the polynucleotides comprising the nucleotide sequences complementary to the nucleotide sequences shown in SEQ ID Nos.: 1-756 may be immobilized on the chip; alternatively, for example, antibodies that specifically recognize and bind to all the peptides comprising the amino acid sequences shown in SEQ ID Nos.: 757-1512 may be immobilized on the chip. The CDR3 polynucleotides or the polynucleotides complementary thereto, the CDR3 peptides, or the antibodies against the CDR3 peptides may be placed at any position on the chip.

The chips may be used for, for example, diagnosis of cancer as described above. The samples may be affected tissues, body fluids such as blood and lymphatic fluid, or mucosal membranes. Preferably, the samples are peripheral blood. For example, when CDR3 polynucleotides are to be analyzed, the nucleic acids are extracted from the cells according to conventional methods, and a chip onto which all the species of polynucleotides comprising the nucleotide sequences complementary to the nucleotide sequences shown in SEQ ID Nos.: 1-756 are immobilized may be used to examine the species and quantity of the hybridized DNA present in the sample. Also, for example, when CDR3 peptides are to be analyzed, a chip onto which antibodies that specifically recognize and bind to all the species of peptides comprising the amino acid sequences shown in SEQ ID Nos.: 757-1512 are immobilized may be used to examine the species and quantity of the specifically bound peptides present in the sample.

In this regard, the present invention provides an antibody that specifically recognizes and binds to a CDR3 peptide. Preferably, such an antibody specifically recognizes and binds to any of the amino acid sequences shown in SEQ ID Nos.: 757-1512. Methods for preparing such an antibody are known to those skilled in the art.

Typically, DNAs in the sample or DNA sequences placed on the chip are labeled so that the presence or absence, or the amount of hybridization is indicated. For example, the presence or absence, or the species of CDR3 peptides in a sample may be identified by arraying antibodies for each of the CDR3 peptides of SEQ ID Nos.: 757-1512 on a chip and testing for their specific binding to the CDR3 peptides present in the sample. Typically, the peptides in the sample or the antibodies on the chip are labeled so that the presence or absence of the specific binding can be determined. Labels capable of indicating the presence or absence and the amount of hybridization or specific binding are known and include, for example, fluorescent labels, radioactive labels, enzyme labels, and chromophore labels. One skilled in the art may conveniently select suitable labels. The chips described above may be used to analyze a plurality of samples at the same time.

The CDR3 polynucleotides and CDR peptides of the present invention may be analyzed and identified using a known method, such as Southern blotting, Northern blotting, colony hybridization, and ELISA, as well as using the chips described above.

As described above, the CDR3 DNAs of the present invention have been identified using the primers shown in Examples, particularly, the primer sets shown in Table 1. Therefore, the present invention provides primers for amplifying CDR polynucleotides, which primers having the sequences selected from the sequences shown in SEQ ID Nos.: 1513-1538. For example, a primer set comprising the primers shown in SEQ ID Nos.: 1513-1538 may be used for amplification of a CDR3 polynucleotide.

The present invention also provides a kit for diagnosing cancer including means for detecting a WT1-specific CTL having a CDR3 polynucleotide or CDR3 peptide; a kit for testing for the sensitivity of a patient to WT1 peptide immunotherapy; or a kit for monitoring WT1 peptide immunotherapy. The present invention further provides a device for cancer diagnosis including means for detecting a WT1-specific CTL having a CDR3 polynucleotide or CDR3 peptide; a device for testing for the sensitivity of a cancer patient to WT1 peptide immunotherapy; or a device for monitoring WT1 peptide immunotherapy. A part for amplifying genes, such as a primer set, as described above, a chip as described above, or means for analyzing the information obtained from the chip may be used in the kit as a component or in the device.

In still another aspect, the present invention relates to a lymphocyte from an HLA-A*0201-positive patient, which lymphocyte incorporating a T-cell receptor gene containing a sequence of a CDR3 polynucleotide. HLA-A*0201-positive individuals include humans not suffering from cancer and cancer patients. A HLA-A*0201-positive individual may be, for example, a healthy individual, a donor for bone-marrow transplant or a cancer patient. Preferably, such a lymphocyte is a peripheral blood lymphocyte into which the gene for the Vβ chain of TCR of WT1-specific CTLs comprising a CDR3 polynucleotide of the present invention, and a gene for the Vα chain of TCR of WT1-specific CTLs. In preparation of such a peripheral blood lymphocyte, a single species of the gene for the Vβ chain of TCR of WT1-specific CTLs may be used to obtain a plurality of types of peripheral blood lymphocytes, which are in turn introduced into patients. However, in view of improving the therapeutic effect, it is preferred to use a plurality of species of the gene for the Vβ chain of TCR of WT1-specific CTLs to obtain a plurality of types of peripheral blood lymphocytes, which are in turn introduced into patients. Alternatively, it is also preferred to select the nucleotide sequences of a suitable gene to be introduced depending on individual circumstances, because the therapeutically effective nucleotide sequences in the gene may differ depending on patients and cancer types. In addition, as used herein, the term "treatment" of cancer includes not only procedure of tumor such as inhibition of cancer progression, reduction of cancer, disappearance of cancer, and the like, but also prevention of cancer recurrence.

Methods for preparing a gene to be introduced and for introducing the gene into peripheral blood lymphocytes are known in the art. For example, a gene to be introduced may be integrated into a suitable vector and then introduced into suitable cells, or may be introduced into suitable cells by biolistic bombardment or electroporation. Other conditions for gene transfer and for cell culture may be appropriately selected by those skilled in the art.

The lymphocytes into which a gene has been introduced as described above may be cultured ex vivo to obtain a large amount of WT1-specific CTLs. Then, the WT1-specific CTLs obtained may be introduced into a cancer patient to kill tumor cells expressing WT1, thereby performing cancer therapy. When such a cancer therapy is performed, it is preferred that a gene is introduced as described above into peripheral blood lymphocytes obtained from a cancer patient who should be treated and the obtained WT1-specific CTLs are introduced into the same cancer patient.

The cancer therapy described above may be combined with other cancer therapies including anti-cancer agents and radiotherapy. The cancer therapy described above has a wide range of applications. They are exemplified above, but are not limited thereto.

In still another aspect, the present invention provides an antibody against a CDR3 peptide and a method of use thereof. Methods for preparing such an antibody are known in the art. Such an antibody may be used to detect or identify a lymphocyte having the amino acid sequence of the CDR3 peptide of the present invention or an amino acid sequence containing the above sequence in its Vβ chain in the subject sample. For example, antibodies against peptides comprising the amino acid sequences of any of SEQ ID Nos.: 757-1512 may be used to detect or identify cancer-specific lymphocytes. These antibodies may also be used to carry out the methods of the present invention, for example, the method for diagnosing cancer.

Such an antibody may also be contacted with lymphocytes having the amino acid sequence of CDR3 of the present invention to activate them. The lymphocytes thus activated may be used to treat cancer. Preferably, lymphocytes obtained from a cancer patient are activated and, if necessary, proliferated, and the cancer therapy is conducted by returning the lymphocytes to the patient. Such an antibody may also be used to enrich the WT1-specific T-cells of interest. For example, such an antibody may be used to enrich the WT1-specific T-cells in a cancer patient, thereby assisting the cancer therapy.

In a further aspect, the present invention provides a method for identifying the position and size of a solid cancer, the method including: administering the peripheral blood lymphocytes of the present invention described above after being labeled with a detectable label, and then examining the location and quantity of the label. The label may be a known label, such as radioactive label, e.g. Tecnecium-99, and fluorescent label. Methods for labeling cells are also known. Detection of labels and quantification of signals are also known in the art; they can be performed using a radiation counter, by fluorescence assay, or by obtaining a tissue sample by biopsy.

The present invention is illustrated in greater detail below with reference to Examples, but it should be understood that the present invention is not construed as being limited thereto.

Example 1

A. Experimental Methods and Materials Used (1) Cell Samples

Peripheral blood samples were obtained from five healthy volunteers (HD1 to HD5) and six HLA-A*0201-positive solid cancer patients (PT1 to PT6). HLA alleles of healthy individuals and cancer patients are HD1:0201/2402, HD2:0201/0206, HD3:0201/2602, HD4:0201/3303, HD5:0201/2402, PT1:0201/2402, PT2:0201/2402, PT3:0201/2402, PT4:0201/2402, PT5:0201/2402, PT6:0201/2402. The obtained peripheral blood samples were subjected to Ficoll-Hypaque (Pharmacia, Uppsala, Sweden) density gradient centrifugation and peripheral blood mononuclear cells (PBMCs) were separated and stored frozen at −170° C. until use.

(2) Flow Cytometric Analysis and Sorting

Initially, $2 \times 10^6$ PBMCs per sample were stained with PE-conjugated HLA-A*0201-WT1 126-134 tetramers (MBL, Tokyo, Japan) in FACS buffer (PBS containing 2% fetal bovine serum) at 37° C. for 30 minutes. Subsequently, they were stained with monoclonal antibodies labeled with five different fluorescent dyes as described below for 25 minutes on ice in dark: FITC-labeled anti-CD4, CD14, CD16, CD19, and CD56, anti-CD3-PerCP, anti-CD8-APC-Cy7 (BD Bioscience, San Jose, Calif.), anti-CD45RA-APC, and anti-CCR7-PE-Cy7 (BD Pharmingen, San Diego, Calif.). The stained cells were washed twice in FACS buffer. Sorting was performed using the FACSAria™ system (BD Biosciences) and data analysis was performed using the FACSDiva™ software (BD Biosciences). As a result, single HLA-A*0201-WT1$_{126-134}$ tetramer$^+$CD3$^+$CD8$^+$ cells were obtained from the fraction of CD4$^-$CD14$^-$CD16$^-$CD19$^-$CD56$^-$ cells and were defined as WT1-Tet$^+$ cells.

(3) cDNA Synthesis of the TCR-β Chain from the Sorted Single Cells

The single WT1-Tet+ cells obtained as described above were sorted directly in a PCR tube containing a reaction mixture (reaction volume 20 μl), cDNA synthesis was carried out by incubation at 50° C. for 90 minutes, and then the samples were incubated at 95° C. for 5 minutes for terminating the reaction. The compositions of RT reaction solutions are shown in Table 1.

TABLE 1

| Component | Final concentration |
|---|---|
| RT buffer (containing Triton ™ X-100) | 1x |
| Cb-RT primer caccagtgtggccttttg (SEQ ID No: 1513) | 200 nM |
| dNTP | 0.5 mM |
| Rnase inhibitor (Invitrogen) | 0.875 U/μl |
| SuperScript ® III (Invitrogen) | 4.5 U/μl |
| gelatin | 100 μg/ml |
| tRNA | 100 μg/ml |

(4) PCR Reaction

Ten μl of a synthesized cDNA product obtained by the above procedure was added to 40 μl of a reaction mixture in order to perform 1st PCR reaction. The procedure of PCR was as follows: a pre-PCR heating step at 95° C. for 9 minutes, followed by 40 cycles of a denaturing step at 95° C. for 45 seconds, an annealing step at 57° C. for 45 seconds, and an extension step at 72° C. for 50 seconds. The compositions of 1st PCR reaction solutions are shown in Table 2.

TABLE 2

| Component | Final concentration |
|---|---|
| PCR buffer (not containing Mg) | 1x |
| MgCl$_2$ | 2 mM |
| dNTP | 0.25 mM |
| Platinum ® Taq DNA polymerase (Invitrogen) | 0.02 U/μl |
| Cb-RT primer (reverse) | 5 nM |
| Vb PCR-1~3 primer mix (forward) | 5 nM of each primer |

* Vb PCR-1 mix contained S1 mix, S2 mix and S7 mix. Vb PCR-2 mix contained S3 mix, S4 mix and S8 mix. Vb PCR-3 mix contained S5 mix and S6 mix.

Next, the above PCR products were subjected to 2nd PCR (screening PCR). The above PCR products were placed in separate 8 tubes, respectively, and a reaction mixture was added to each of the tubes. The procedure of PCR was as follows: a pre-PCR heating step at 95° C. for 9 minutes, followed by 35 cycles of a denaturing step at 94° C. for 45 seconds, an annealing step at 57° C. for 45 seconds, and an extension step at 72° C. for 40 seconds. The compositions of 2nd PCR reaction solutions are shown in Table 3.

TABLE 3

| Component | Final concentration |
|---|---|
| PCR buffer (not containing Mg) | 1x |
| MgCl$_2$ | 2.5 mM |
| dNTP | 0.2 mM |
| Platinum ® Taq DNA polymerase (Invitrogen) | 0.0125 U/μl |

TABLE 3-continued

| Component | Final concentration |
|---|---|
| universal Cb primer ggaacacgttttttcaggtcct (SEQ ID No: 1514) (reverse) | 150 nM |
| S mix primer (forward)** | 150 nM |

**Each of S1 mix primer~S8 mix primer was added to each of eight tubes.

Each of S mix primer contained primers shown in Table 4.

TABLE 4

| | | |
|---|---|---|
| S1 mix primer | Vb1/5 | acagcaagtgac<tag>ctgagatgctc (SEQ. ID No: 1515~1517) |
| | Vb11 | gatcactctggaatgttctcaaacc (SEQ ID No: 1518) |
| | Vb12 | ccaagacacaaggtcacagagaca (SEQ. ID No: 1519) |
| S2 mix primer | Vb2 | gagtgccgttccctggactttcag (SEQ ID No: 1520) |
| | Vb3 | gtaacccagagctcgagatatcta (SEQ ID No: 1521) |
| | Vb22 | ggtcacacagatgggacaggaagt (SEQ ID No: 1522) |
| S3 mix primer | Vb4 | tccagtgtcaagtcgatagccaagtc (SEQ ID No: 1523) |
| | Vb6.a | atgtaact<ct>tcaggtgtgatccaa (SEQ ID No: 1524~1525) |
| | Vb14 | gtgacccagaacccaagatacctc (SEQ ID No: 1526) |
| S4 mix primer | Vb6.b | gtgtgatccaatttcaggtcatac (SEQ ID No: 1527) |
| | Vb8 | ggtgacagagatgggacaagaagt (SEQ ID No: 1528) |
| | Vb21 | cagtctcccagatataagattatagag (SEQ ID No: 1529) |
| S5 mix primer | Vb17 | cactcagtccccaaagtacctgtt (SEQ ID No: 1530) |
| | Vb20 | gtcagatctcagactattcatcaatgg (SEQ ID No: 1531) |
| | Vb7 | tacgcagacaccaa<ga>acacctggtca (SEQ ID No: 1532~1533) |
| | Vb9 | cccagactccaaaatacctggtca (SEQ ID No: 1534) |
| | Vb18 | tgcagaacccaagcacctggtca (SEQ ID No: 1535) |
| S6 mix primer | Vb10 | aaggtcacccagagacctagactt (SEQ ID No: 1536) |
| | Vb16 | atagaagctggagttactcagttc (SEQ ID No: 1537) |
| | Vb19 | acaaagatggattgtaccccgaa (SEQ ID No: 1538) |
| S7 mix primer | Vb13 | gtgtcactcagacccccaaaattcc (SEQ ID No: 1539) |
| | Vb15 | gttacccagaccccaaggaatagg (SEQ ID No: 1540) |
| S8 mix primer | Vb23 | ctgatcaaagaaaagagggaaacagcc (SEQ ID No: 1541) |
| | Vb24 | caagataccaggttacccagtttg (SEQ ID No: 1542) |

In the table 4, "< >" means that one nucleotide is selected from listed nucleotides. For example, in case " . . . <ct> . . . " is represented, this means that there are two sequences, i.e., " . . . c . . . " and " . . . t . . . ".

To verify positive reactions in the 8 screening PCRs, 5 μl of each screening PCR product was subjected to 2% agarose gel electrophoresis, followed by further PCR. This PCR was performed by 3rd PCR reaction using each of the Vβ-specific forward primers contained in the S mix primer sets that were confirmed as positive and the samples obtained as described above as templates. The procedure of PCR was as follows: a pre-PCR heating step at 95° C. for 9 minutes, followed by 35 cycles of a denaturing step at 94° C. for 45 seconds, an annealing step at 57° C. for 45 seconds, and an extension step at 72° C. for 40 seconds. The compositions of 2nd PCR reaction solutions are shown in Table 5. The reaction products were applied to 2% agarose gel electrophoresis to verify the positive reaction. The experiment was performed according to the same procedure as above using a cell-free system as a negative control.

TABLE 5

| Component | Final concentration |
|---|---|
| PCR buffer (not containing Mg) | 1x |
| MgCl$_2$ | 2.5 mM |
| dNTP | 0.2 mM |
| Platinum ® Taq DNA polymerase (Invitrogen) | 0.0125 U/µl |
| universal Cb primer (reverse) | 150 nM |
| Vb mix primer (forward)*** | 200 nM |

***For example, when the positive reaction had verified in the reaction system using the above S1 mix primer, 3rd PCR reaction was performed using each of Vb1/5, Vb11 and Vb12 which were components of S1 mix primer.

(5) Determination and Analysis of the Sequences of the Complementality-Determining Region 3 (CDR3) of TCR-β

The 3rd PCT products were applied to 2% agarose gel electrophoresis to verify the positive reaction. Amplified fragments of the TCR-β gene were purified using the k QIAquick™ PCR Purification kit (Qiagen, Valencia, Calif.). Corresponding Vb primers were used for sequencing. The ABI PRIAM BigDye® Terminator v 3.1 Cycle Sequencing kit (Applied Biosystems, Foster City, Calif., USA) was used for sequencing, and the ABI PRISM® 3100 Genetic Analyzer (Applied Biosystems) was used for analysis. The sequence data on CDR3 were analyzed by comparing the sequences with those available from the website of the IMGT® human TCR gene database (imgt (dot) cines (dot) fr/IMGT_vquest/vquestlivret=0&Option=humanTcRfor).

B. Results

In the present invention, the base sequences of 636 genes for the TCR β chain in peripheral blood mononuclear cell from five HLA-A*0201-positive healthy individuals (HD1 to HD5) and six HLA-A*0201-positive cancer patients (PT1 to PT6) could be determined, and the amino acid sequences encoded by the genes could be determined. The sequences of the gene for the Vβ chain, the J region sequences, D region sequences, N region sequences, CDR3 nucleotide sequences, and CDR3 amino acid sequences of WT1-specific CTLs derived from healthy individuals (HD1 to HD5) and cancer patients (PT1 to PT6) are shown in FIGS. 1-1 to 1-9. The clonality of WT1-specific CTLs of each individual is shown in FIGS. 2-1 to 2-13. The CDR3 nucleotide sequences are shown in SEQ ID Nos.: 1-636, and the CDR3 amino acid sequences are shown in SEQ ID Nos.: 757-1392 according to the ID NO numbering in FIGS. 1A to 1I.

In addition, according to the above-described procedure, CDR3 nucleotide sequence and CDR3 amino acid sequence were determined from peripheral blood samples of one HLA-A*0201-positive thyroid cancer patient (PT7) and one HLA-A*0201-positive healthy individual (HD6). CDR3 nucleotide sequences obtained from PT7 and HD6 are shown in SEQ ID Nos.: 637-756 and CDR3 amino acid sequences obtained from PT7 and HD6 are shown in SEQ ID Nos.: 1393-1512.

As can be seen from FIGS. 2-1 to 2-13, in the healthy individuals (HD1 to HD5), the clonality of WT1-specific CTL having any of the CDR3 polynucleotides or CDR3 peptides is 1 for almost all the clones, 2 or 3 for rare clones, and 4 for rarer clone (only 1 clone); however, all the cancer patients before therapy (AMLs and MDSs) have a multiplicity of clonality of the WT1-specific CTLs having any of the CDR3 polynucleotides or CDR3 peptides without exception. The number of the clonality tended to be larger and the types of such cells tended to be more abundant in the cancer patients than in the healthy individuals. Specifically, PT1: 4 types (clonality of 30 in total); PT2: 10 types (clonality of 38 in total); PT3: 8 types (clonality of 26 in total); PT4: 4 types (clonality of 9 in total); PT5: 9 types (clonality of 20 in total); and PT6: 5 types (clonality of 13 in total). On the other hand, in healthy individuals HD1 to HD5, the types of clones with a multiplicity of clonality in each individual are 1 to 5 types and the clonality in total was 2 to 10.

Hereinbefore, the present invention was described for the case where HLA-A allele was A*0201; however, the present application can be applicable for the case where HLA-A allele is A*0206.

INDUSTRIAL APPLICABILITY

The present invention provides pharmaceutical compositions useful for anti-cancer therapy, cancer test kits or reagents, reagents for cancer research, and the like. Therefore, the present invention may find use in the fields of pharmaceuticals for cancer therapy, of cancer test kits or reagents, and of cancer research.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10648036B2). An electronic copy of the "Sequence Listing" will also be available from the USPTO upon request and payment of the fee set forth in 37 CFR 1.19(b)(3).

The invention claimed is:
1. A method of assaying a clonality of WT1-specific cytotoxic T-cells (CTLs), the method comprising:
   (a) obtaining a sample from an HLA-A*0201-positive subject, wherein the sample is a tissue affected with a cancer which is generated from cells containing WT1, a body fluid, or a mucosal membrane;
   (b) sorting a single WT1-specific CTL in the sample;
   (c) amplifying a polynucleotide from the single WT1-specific CTL, the polynucleotide comprising:

(i) a nucleotide sequence selected from the group consisting of SEQ ID NOs: 1-756,
(ii) a complementary RNA sequence of the nucleotide sequence (i), or
(iii) a complementary DNA sequence of the nucleotide sequence (i);

or hybridizing a polynucleotide in the single WT1-specific CTL with at least one polynucleotide comprising:
(i) a nucleotide sequence selected from the group consisting of SEQ ID NOs: 1-756,
(ii) a complementary RNA sequence of the nucleotide sequence (i), or
(iii) a complementary DNA sequence of the nucleotide sequence (i); and (d) measuring the clonality of WT1-specific CTLs that comprise an identical nucleotide sequence selected from the group consisting of SEQ ID NOs: 1-756, thereby characterizing the WT1-specific CTLs as having a multiplicity of clonality if the clonality is greater than 1, and/or measuring the number of types of WT1-specific CTLs having the multiplicity of clonality.

2. The method of claim 1, wherein the at least one polynucleotide in the hybridizing is immobilized on a chip.

3. The method of claim 1, wherein (c) comprises amplifying a polynucleotide from the single WT1-specific CTL.

4. The method of claim 1, wherein (c) comprises hybridizing a polynucleotide in the single WT1-specific CTL.

5. The method of claim 1, wherein (d) comprises measuring the clonality of WT1-specific CTLs that comprise an identical nucleotide sequence selected from the group consisting of SEQ ID NOs: 1-756.

6. The method of claim 1, wherein (d) comprises measuring the number of types of WT1-specific CTLs having the multiplicity of clonality.

7. A method for assaying a clonality of WT1-specific CTLs, comprising:
(a) obtaining a sample from an HLA-A*0201-positive subject, wherein the sample is a tissue affected with a cancer which is generated from cells containing WT1, a body fluid, or a mucosal membrane;
(b) sorting a single WT1-specific CTL in the sample;
(c) contacting a peptide from a single WT1-specific CTL with an antibody against a peptide comprising an amino acid sequence selected from the group consisting of SEQ ID NOs: 757-1512; and
(d) measuring the clonality of WT1-specific CTLs that comprise an identical amino acid sequence selected from the group consisting of SEQ ID NOs: 757-1512, thereby characterizing the WT1-specific CTLs as having a multiplicity of clonality if the clonality is greater than 1;

and/or measuring the number of types of WT1-specific CTLs that have a multiplicity of clonality.

8. The method of claim 7, wherein the antibody in the contacting is immobilized on a chip.

* * * * *